(12) United States Patent
He et al.

(10) Patent No.: US 10,513,535 B2
(45) Date of Patent: Dec. 24, 2019

(54) SELF-REPLICATION OF NUCLEIC ACID ORIGAMI TILES

(71) Applicant: New York University, New York, NY (US)

(72) Inventors: Xiaojin He, New York City, NY (US); Ruojie Sha, Basking Ridge, NJ (US); Yongli Mi, Kowloon (HK); Paul Chaikin, New York, NY (US); Nadrian C. Seeman, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 586 days.

(21) Appl. No.: 14/923,361

(22) Filed: Oct. 26, 2015

(65) Prior Publication Data

US 2016/0215317 A1    Jul. 28, 2016

Related U.S. Application Data

(60) Provisional application No. 62/068,070, filed on Oct. 24, 2014.

(51) Int. Cl.
| | |
|---|---|
| *C12P 19/34* | (2006.01) |
| *C07H 21/04* | (2006.01) |
| *C12Q 1/6816* | (2018.01) |
| *C12N 15/11* | (2006.01) |

(52) U.S. Cl.
CPC ............. *C07H 21/04* (2013.01); *C12N 15/11* (2013.01); *C12Q 1/6816* (2013.01)

(58) Field of Classification Search
None
See application file for complete search history.

(56) References Cited

PUBLICATIONS

Wang et al. (Nature 478.7368 (2011): 225-228) (Year: 2011).*
Wang et al. (Nature 478.7368 (2011): 225-228) supplementary materials (Year: 2011).*
Van Anders et al.( Nature chemistry 4.2 (2012): 79-80) (Year: 2012).*
Gerrard et al.( Acs Nano 6.10 (2012): 9221-9228). (Year: 2012).*
Lin et al.(Nano letters 7.2 (2007): 507-512.) (Year: 2007).*
Lin et al.(Nano letters 7.2 (2007): 507-512.) supplementary materials (Year: 2007).*
Kohlmeyer et al. (Angewandte Chemie International Edition 52.35 (2013): 9234-9237) (Year: 2013).*
Xiao et al. ( Angewandte Chemie 124.47 (2012): 12023-12027). (Year: 2012).*
Schulman et al.(Proceedings of the national academy of sciences (2012); 6 pages). (Year: 2012).*
Barish et al. (Proceedings of the National Academy of Sciences 106.15 (2009): 6054-6059.) (Year: 2009).*
Barish 2009 supp methods (Year: 2009).*
Cho et al., Controlled release of an anti-cancer drug from DNA structured nano-films, Nature, pp. 1-7 (2014).
Rothemund, Folding DNA to create nanoscale shapes and patterns, Nature, 440(16):297-302 (2006).
Adleman, Molecular computation of solutions to combinatorial problems, Science, 266(5187):1021-1024 (1994).
Lincoln et al., Self-sustained replication of an RNA enzyme, Science, 323:1229-1232 (2009).
Ouyang et al., Rolling circle amplification-based DNA origami nanostructrures for intracellular delivery of immunostimulatory drugs, Small, 9(18):3082-3087 (2013).
Zhao et al., DNA origami delivery system for cancer therapy with tunable release properties, American Chemical Society, 6(10):8684-8691 (2012).
Wang et al., Self-replication of information-bearing nanoscale patterns, Nature, 478:225-229 (2011).

* cited by examiner

*Primary Examiner* — Tracy Vivlemore
*Assistant Examiner* — Sahana S Kaup
(74) *Attorney, Agent, or Firm* — Browdy and Neimark, PLLC

(57) ABSTRACT

The present invention provides a method for self-replication of multimers of nucleic acid origami tiles by exponentially amplifying the multimer from initial seeds of monomeric units of nucleic acid origami tiles and also provides for the selective exponential amplification of a designated multimer, such as with specific properties or characteristics, over one or more competing multimers in the presence of a mixture of monomers for each of the possible multimers. The selection of the designated multimer based on an environmental change allows the designated multimer to outgrow all competing multimers.

17 Claims, 22 Drawing Sheets

Specification includes a Sequence Listing.

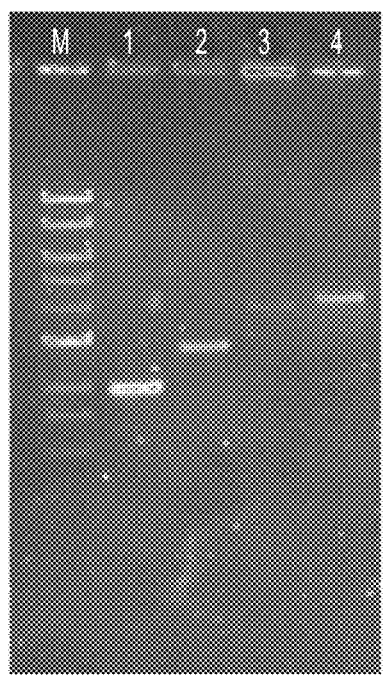 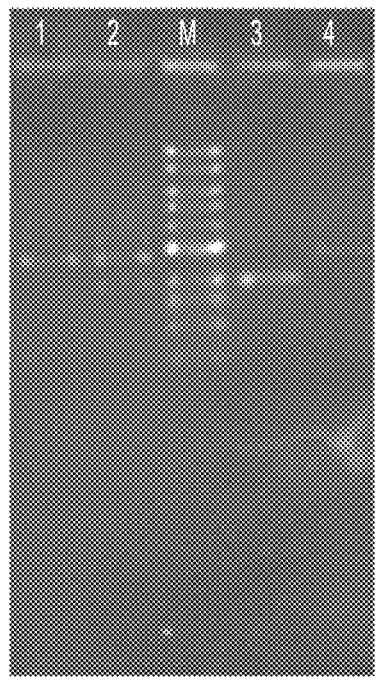
FIG. 9A    FIG. 9B
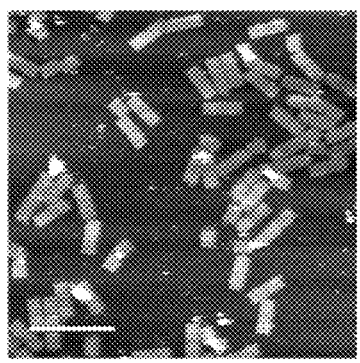 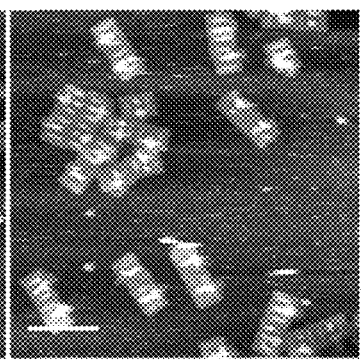
FIG. 10A    FIG. 10B
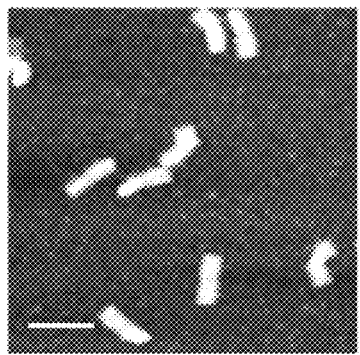 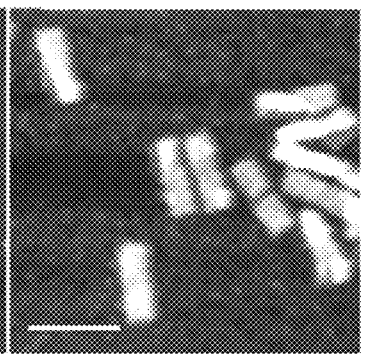
FIG. 10C    FIG. 10D

SELF-REPLICATION OF NUCLEIC ACID ORIGAMI TILES

GOVERNMENT LICENSE RIGHTS

This research was primarily supported by the DOE-BES under grant DE-SC0007991 with further support under GM-29554 from NIGMS, grants CMMI-1120890, CCF-1117210 and EFRI-1332411 from the NSF, MURI W911NF-11-1-0024 from ARO, grants N000141110729 and N000140911118 from ONR, NASA NNX08AK04G, and Award No. CMMI-0957834. The U.S. Government has a paid-up license in this invention and the right in limited circumstances to require the patent owner to license others on reasonable terms as provided for by the terms of the above grants.

BACKGROUND OF THE INVENTION

Field of the Invention

The present invention relates to the field of nucleic acid nanotechnology, particularly in the area of nucleic acid origami tiles and self-replication.

Description of the Related Art

Self-replication and evolution by selective pressures are inherent phenomena in life, but few artificial systems exhibit these phenomena. There has been renewed interest in developing self-replicating systems at the submicron scale to gain insights into diverse problems ranging from the origin of life to information, computation and materials science (Lincoln et al., 2009; Wintner et al., 1994; Schulman et al., 2007; Lin et al., 1008; Lee et al., 1997; Eckardt et al., 2002; Wang et al., 2011; Leunissen et al., 2009; Ellington et al., 1990; and Tuerk et al., 1990). Materials that multiply and can be selected to evolve with specific properties are expected to provide a new paradigm for design from the nanoscopic to the microscopic.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a method for self-replication of multimers of nucleic acid origami tiles by exponentially amplifying the multimer from initial seeds of monomeric units of nucleic acid origami tiles.

The present method also provides for the selective exponential amplification of a designated multimer (e.g., with specific properties or characteristics) over one or more competing multimers in the presence of a mixture of monomers for each of the possible multimers. The selection of the designated multimer based on an environmental change allows the designated multimer to outgrow all competing multimers.

BRIEF DESCRIPTION OF THE DRAWINGS

FIG. 1A—Seed and later generation tiles design, (Seed and first-generation tile (A-tile) design, comprising three domains: (1) DNA hairpin structures to create a topographic feature that can be detected by AFM (seed and second-generation tiles labeled with 'T' and first generation tiles labeled with 'A'); (2) vertical sticky ends, which pair with the successive-generation tiles; (3) both 'T' and 'A' have the same horizontal sticky ends as linkers (dotted with $^{CNV}K$ and dashed) to connect other tiles in the same generation, right side sticky ends complementary to left side. FIG. 1B—Photo-cross-linking with $^{CNV}K$ Photo-cross-linking reagent in a DNA duplex. FIG. 1C—Self-replication cycling of the dimer seed system, including 'TT' seed formation with special horizontal complementary sticky ends, recognition and hybridization of daughter tiles to seeds with vertical bonds, formation of new-generation dimers using horizontal bonds and the $^{CNV}K$ photo-cross-linking reaction and separation of the two successive generations by heating the system to ~46° C. The left-side cycles include seed tiles and the right-side cycles do not.

FIG. 2A—Schematic illustrations and AFM images of a (i) DNA dimer seed 'TT', (ii) a first generation tile (A-tile) and (iii) a double-layer complex of seed and two first-generation tiles. FIG. 2B—The amplification of dimers (including seeds and later-generations) increased exponentially before leveling off as the supply of substrates was exhausted. Curves with square (and solid line), circles and triangles represent self-replication cycling containing seeds, first-generation and second-generation tiles with ratios of 1:1024:1022, 1:32:30 and 1:16:14, respectively. The curve with squares and a dashed line is the theoretical curve for exponential growth. The dimer amplification factor was calculated at the end of each cycle. FIG. 2C—AFM images of self-replication cycles for the dimer system: (i) cycle 0, (ii) cycle 8 and (iii) zoomed-in image of dimers 'TT' and 'AA' in cycle 8. The initial ratio of seed, first-generation tile and second-generation tile is 1:32:30. Scale bars in (i) and (ii) are 500 nm. The scale bar in (iii) is 100 nm.

FIG. 3A—A self-replication amplification curve that was obtained by six successive replications, allowing approximately 14-fold amplification before transferring 8% of the mixture to the next replication tube, which contained a fresh supply of later-generation monomers. FIG. 3B—A non-denaturing agarose gel demonstrating and quantifying the amplification of dimers in replication cycles 8-12, after a transfer experiment. Lane 1 contains a 1 kb DNA marker. Lanes 2 and 3 contain first-generation tile 'A' and dimer seed 'TT', respectively. Lanes 4-8 contain the mixtures from replication cycles 8 to 12. The intensity of the band representing dimer tiles increases as cycling occurs. The gel was run at ~48° C. Plots of dimer amplification versus cycle (cycles 8 to 12) obtained from nondenaturing gel and AFM imaging show that the two curves almost overlap, indicating that the AFM quantification is consistent with the gel quantification (data not shown). FIG. 3C—AFM images of the mixtures in cycles 17-20 (scale bars: 500 nm).

FIG. 4A—Design of first-generation and second-generation tiles ('H' and 'I') modified with near infrared (NIR) dyes (IR dyes). IR Dye 800 molecules (dotted circles) and IR Dye 700 molecules (hatched circles) were attached to a monomer 'I' and a monomer 'H', respectively. (i) For first-generation tiles, four of the dyes are located in the vertical direction and four others are on helper strands in the horizontal direction. CNV-containing strands are shown as dotted lines. (ii) Four IR dyes are all attached to solid line helper strands in the vertical direction for seeds or second-generation tiles. FIG. 4B—AFM images of the two competing species seeds 'II' and HH'. FIG. 4C—Replication selection using different wavelength lasers as environmental factors is indicated schematically. Using the 685-nm laser diode, the species 'II' significantly replicated to produce copies of 'II'. The species 'HH' amplifies faster when the wavelength is changed to 785 nm. FIG. 4D—Yields of daughter-generation formation under 685-nm or 785-nm laser irradiation. The ratio of template and monomer was 1:2 in all replication vessels. FIG. 4E—The proportion between species 'HH' and 'II' under various environmental conditions. All solid lines and all dashed lines represent fractional results of dimer 'HH' and dimer 'II', separately. Solid and dashed curves with square data points were measured without laser irradiation, showing the fraction of 'HH' or 'II' is ~50% and indicating the replication of both seeds. Solid and dashed curves with diamond data points represent the data obtained under 785-nm laser exposure. The fraction of dimer 'HH' reached above 94%. Dimer 'II' became the dominant species under 685-laser exposure (triangle dashed line), while species 'HH' decreased to less than 10% of all dimer tiles (triangle solid line). Solid and dashed curves with circle data points show the dominant group can be switched after environmental conditions change (laser wavelength changed from 685 nm to 785 nm after the first 2 cycles). FIG. 4F—AFM images of purified dimers (from the replication mixtures), 'HH' and 'II', under 685-nm laser irradiation. FIG. 4G—AFM images of purified dimers (from the replication mixtures), 'HH' and 'II', under 785-nm laser irradiation. Scale bars in FIGS. 4F and 4G are 500 nm.

Figure 5A:
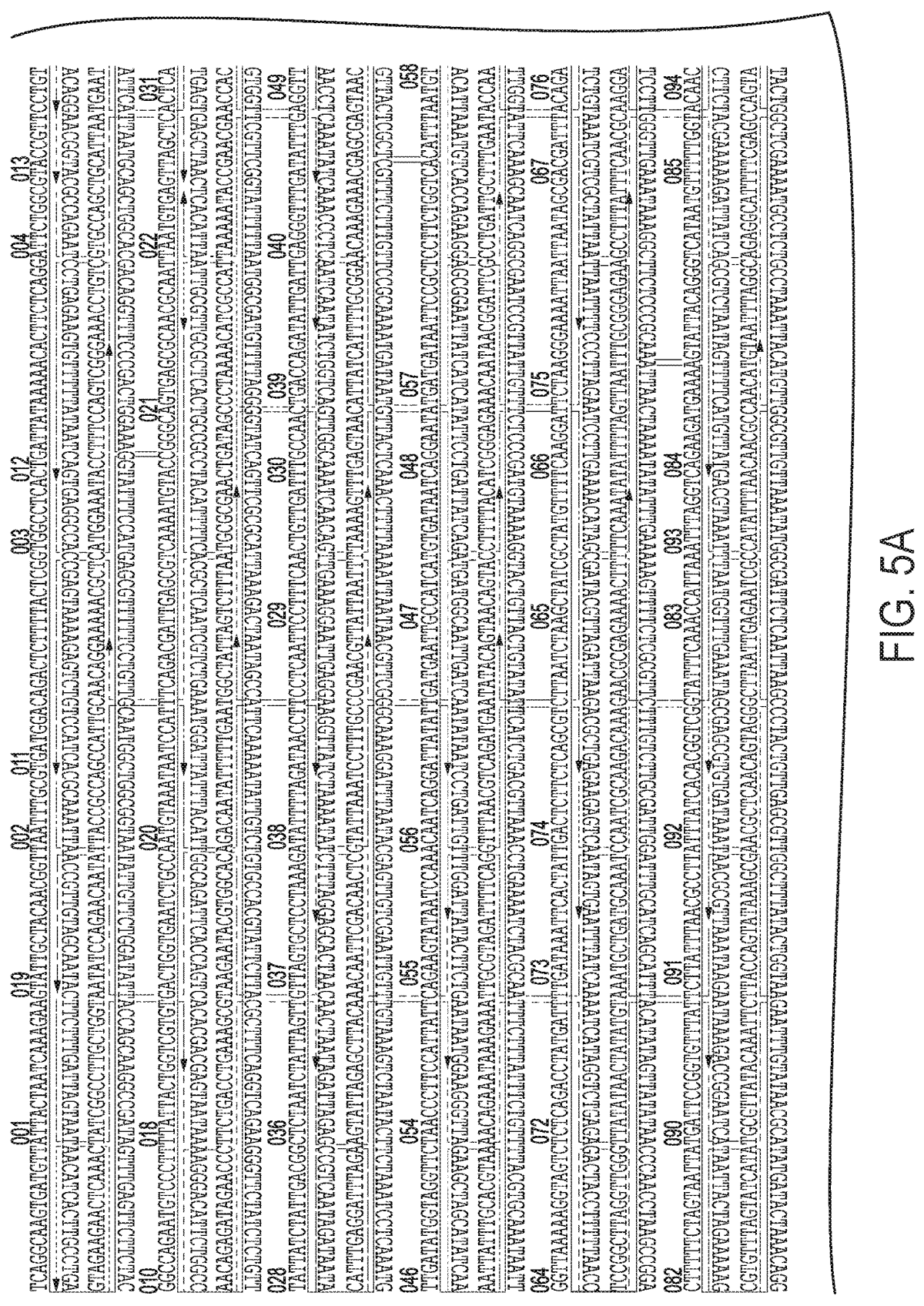
Figure 5B:
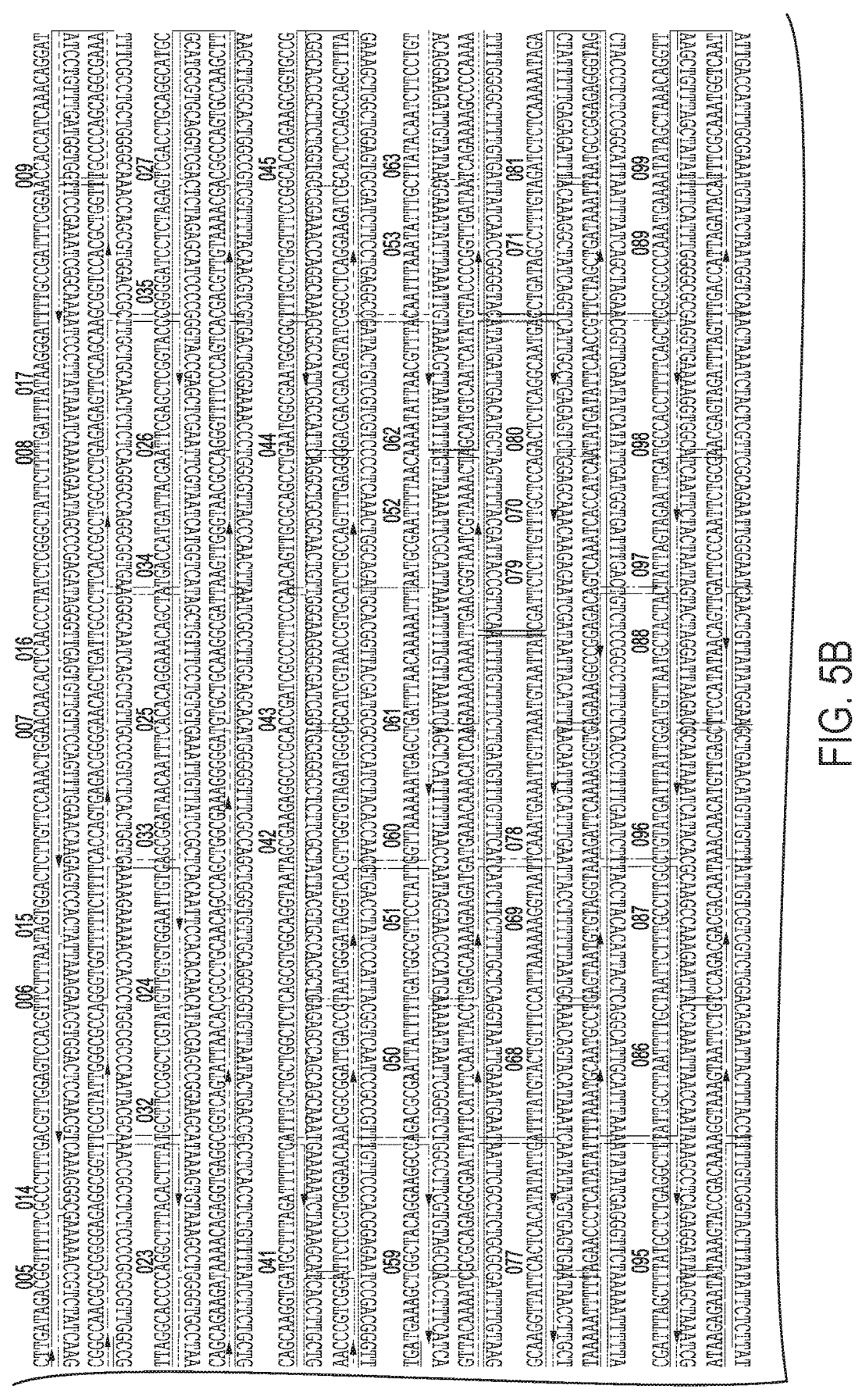
Figure 5C:
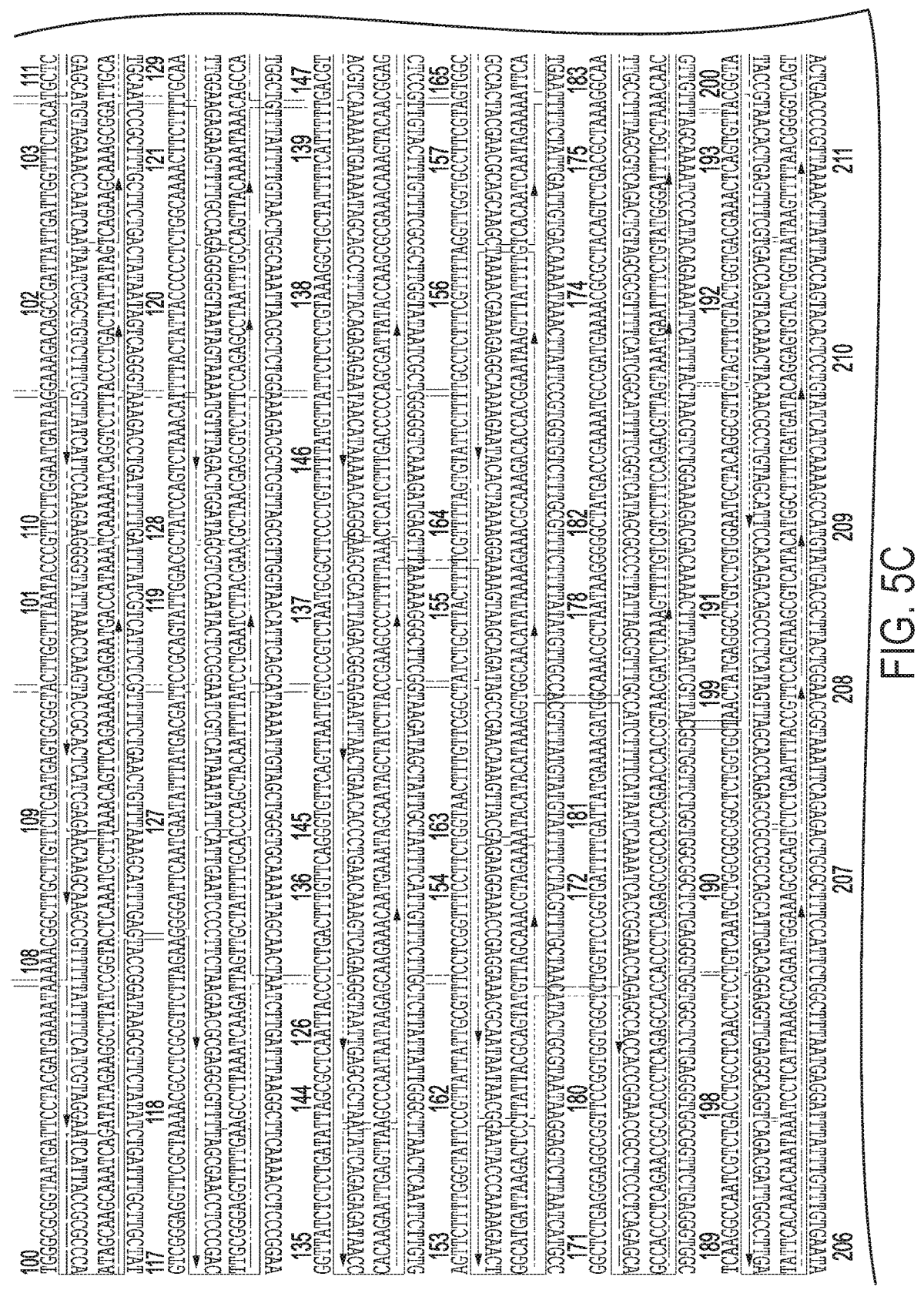
Figure 5D:
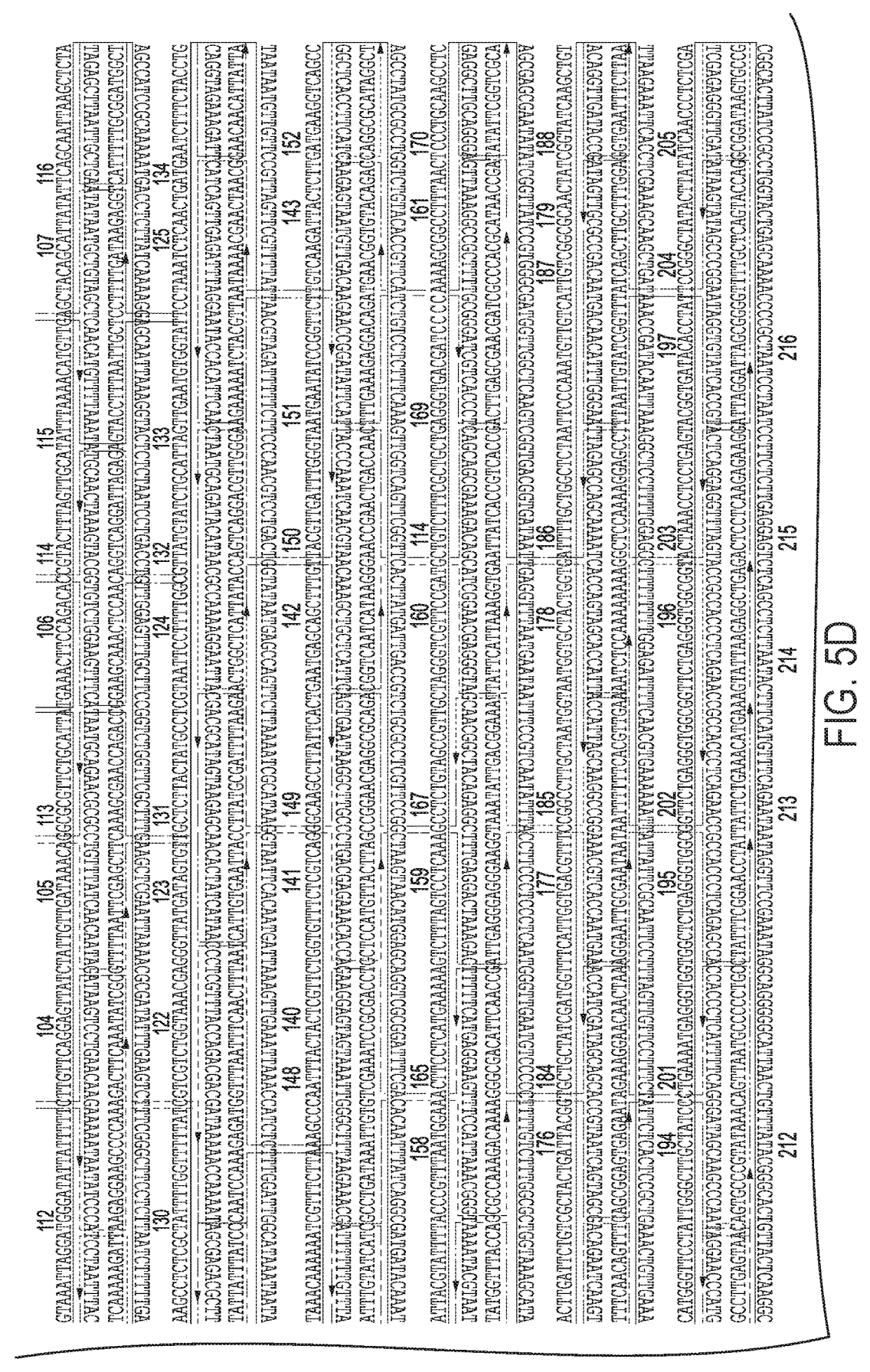

FIGS. 5A-5D show overlapping quadrants of the rectangular DNA origami base structure in its entirety without any modification (SEQ ID NOs:1-216; FIG. 5A upper left quadrant; FIG. 5B upper right quadrant; FIG. 5C lower left quadrant; and FIG. 5D lower right quadrant) that overlay together at the overlapping portions to form the entire rectangular DNA origami base structure.

FIG. 8A—image of origami with 'T' pattern (tapping mode in buffer). FIG. 8B—image of origami with the 'A' pattern (tapping in buffer). (Scale bars in FIGS. 8A and 8B: 250 nm.) FIG. 8C—image of the vertical dimer of the origami tile 'T' and 'A' by vertical sticky-end pairing (tapping in air at 4° C., scale bar in FIG. 8C: 500 nm).

FIGS. 9A and 9B are nondenaturing agarose gel showing formation of complex of dimer DNA origami seed/first-generation tiles and daughter generation. FIG. 9A—Assembly of dimer DNA origami seed and two first-generation tiles (M: 1000 nt pair marker; Lane 1: DNA first-generation tile 'A'; Lane 2: dimer DNA origami seed 'TT'). Lane 3 and Lane 4 show the cohesion of dimer DNA origami seed and two first-generation tiles after and before photo-cross-linking reaction, respectively. The gel was run at 10° C. FIG. 9B—Separation of seed and daughter tiles (Lane M: 1000 nt pairs DNA marker; Lane 3: DNA first-generation tile 'A'; Lane 4: dimer DNA origami seed 'TT'). The band representing the complex of DNA seed and first-generation tile disappears, leading to successful separation. Lane 1 presents separation of seed and photo-cross-linked daughter. There is no lower band (monomer), which indicates the successful formation of daughter generation by template photo-cross-linking reaction. Lane 2 was loaded with the complex of seed and first-generation tile without UV irradiation. The lower band represents the monomer tile 'A', showing no cross-linking between adjacent monomer to form daughter generation 'AA'. The gel was run at ~48° C.

FIGS. 10A-10D show AFM images of the dimer origami tiles. FIG. 10A—dimer seed with 'TT' pattern. FIG. 10B—Extra relatively high resolution images of dimer seed 'TT'. There is one line on each side of the 'T' pattern, which corresponds to topography of vertical sticky ends. FIGS. 10C and 10D—vertical dimer of seed 'TT' and first-generation tiles 'A' by vertical sticky-end pairing. Two first-generation tiles were bound to one seed. Scale bar in FIG. 10A is 500 nm. Scale bars in FIGS. 10B-10D are 250 nm.

FIG. 14A—AFM images of each 2 self-replication cycles under 685-nm laser irradiation, showing the fraction of species 'II' increase as cycling. FIG. 14B—AFM images of each 2 self-replication cycles under 785-nm laser irradiation, showing the fraction of species 'HH' increase as cycling. FIG. 14C—AFM images of each 2 self-replication cycles with laser switch (laser was changed from 685 nm to 785 nm after two replication cycles), indicating that the minor species 'HH' became dominant when the environment was switched. FIG. 14D—AFM images of each 2 self-replication cycles without laser irradiation, showing that the fraction of 'HH' or 'II' maintains 50% and indicating the replication of both seeds. The scale bars are 500 nm.

DETAILED DESCRIPTION OF THE INVENTION

Figure 1A:
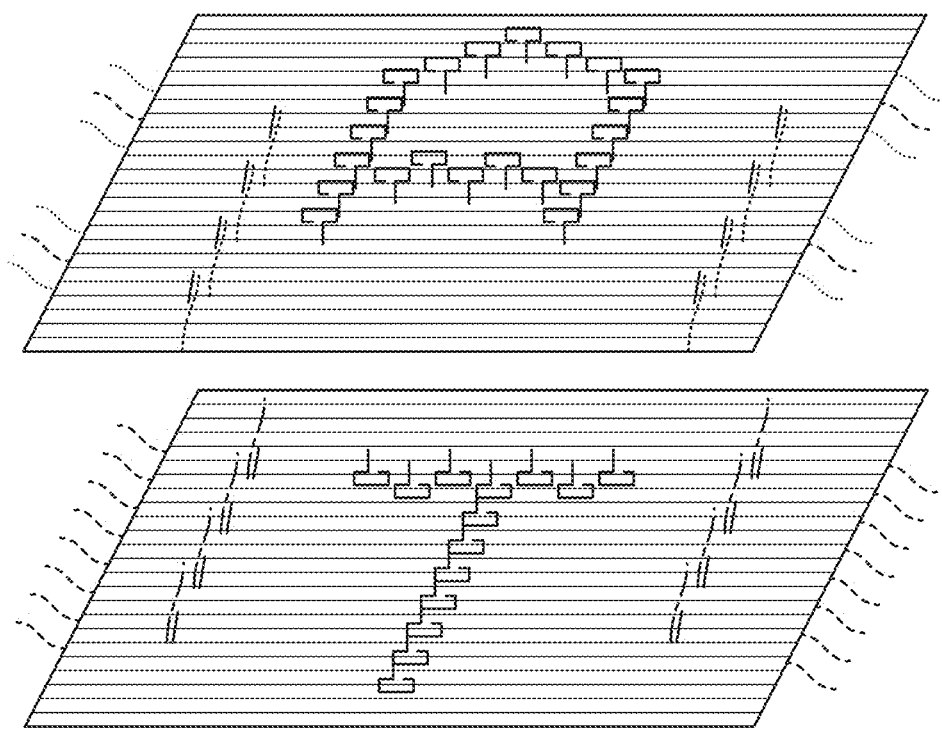
FIGS. 1A-1C schematically illustrate DNA origami tile design and self-replication cycling.

The present invention is directed to the self-replication of nucleic acid origami tiles that have flat surfaces with single-stranded nucleic acid protruding both from the edges (horizontally) and in one direction roughly perpendicular to one of the flat surfaces itself. Given a mother seed of multiple tiles (multimer), a replica can be made of that seed by complementary pairing with the perpendicular strands. The arrangement of individual multiple daughter tiles (first generation tiles and planar like the seed) is covalently fused (e.g., by photo-crosslinking of the horizontal strands that pair with each other) when they assemble in order on the seed. The mother and daughter structures can be separated by mild heating, so that there are now twice as many seeds in the solution. Both mother and daughter can then serve as seeds for the next generation. There is no apparent limit to the amplification, given sufficient daughter tiles. In addition, the daughter tiles from a pool of different mother seeds can be selected for amplification or not. As a non-limiting working example of selection, different dyes have been attached to various daughters. When the solution is illuminated with laser light so that one of the dyes absorbs, that daughter tile is locally heated, so that it cannot be replicated. The daughter that contains a different dye and that does not absorb replicates, and the species with those daughters outstrips the other product (competing multimer), so that after numerous generations, its population is hugely greater than the absorbing species. In this manner, the present invention can be used to amplify and select a given multimer that has specific characteristics or properties from among a population of different multimers.

The experiments in the Example hereinbelow present a preferred embodiment of the present invention in which two dimensional rectangular DNA origami tiles replicate a seed pattern, doubling the copies in each cycle in an exponential fashion. The replication process is driven by diurnal-like cycles of temperature and UV illumination, leading to an amplification of more than 7 million in 24 cycles. This system is also used to demonstrate that two similarly-growing sub-populations with incorporated dyes have growth rates that can be controlled by applying specific environmental stimuli. Appropriately colored light heats the system only in the vicinity of the dyes, enabling the non-absorbing progeny to replicate preferentially, and thereby to take over the system. This addressable selectivity of different constituents in the same solution should be adapted readily to the selection and evolution of multi-component nanoscopic-microscopic self-replicating materials.

The present method for self-replication of nucleic acid origami tiles, includes:

(i) providing a set of monomers of seed, first generation daughter and second generation daughter nucleic acid origami tiles, each monomer having a plurality of horizontal edges and a plurality of faces, with a plurality of sticky cohesive ends protruding from one or more horizontal edges of the tiles and from a one or more faces of the tiles;

(ii) forming a multimer from monomers of seed nucleic acid origami tiles by cohesion of complementary horizontal sticky cohesive ends between edges of adjacent monomers;

(iii) mixing the resulting multimer of seed tiles with monomers of first generation daughter (1G) tiles to allow the monomers to anneal to each other by horizontal sticky end cohesion between edges of adjacent 1G monomeric tiles and to the multimer of seed tiles by sticky end cohesion between sticky cohesive ends protruding from the faces of adjacent seed and 1G tiles to form a stacked multimer of seed and 1G tiles;

(iv) covalently linking 1G tiles in sticky end cohesion with each other in the stacked multimer;

(v) heating to denature the horizontal sticky end cohesion between monomers of seed tiles and the vertical sticky end cohesion between monomers of seed tiles and 1G tiles to separate the heat resistant covalently linked 1G tiles as a multimer of 1G tiles;

(vi) mixing the multimer of covalently linked 1G tiles with monomers of second generation daughter (2G) tiles to allow the monomers to anneal to each other by horizontal sticky end cohesion between edges of adjacent 2G monomeric tiles and to the multimer of covalently linked 1G tiles by sticky end cohesion between sticky cohesive ends protruding from the faces of adjacent 1G and 2G tiles to form a stacked multimer of 1G and 2G tiles;

(vii) covalently linking 2G tiles in sticky end cohesion with each other in the stacked multimer;

(viii) heating to denature the vertical sticky end cohesion between the multimer of 1G tiles and the multimer of 2G tiles in the stacked multimer to separate the multimers of covalently linked 1G tiles and covalently linked 2G tiles;

(ix) incubating the separated multimers with monomers of 1G tiles and 2G tiles to allow the monomers of 1G and 2G tiles to anneal respectively to other 1G and 2G monomers by horizontal sticky end cohesion between edges of adjacent monomers tiles and to a multimer of covalently linked 1G or 2G tiles by vertical sticky end cohesion between sticky cohesive ends protruding from the faces of adjacent 1G and 2G tiles to form stacked multimers of 1G and 2G tiles;

(x) for 1G and 2G tiles not already covalently linked, covalently linking 1G tiles in horizontal sticky end cohesion to each other and covalently link 2G tiles in horizontal sticky end cohesion to each other in the stacked multimers;

(xi) heating to denature the vertical sticky end cohesion between multimers of covalently linked 1G tiles and multimers of covalently linked 2G tiles;

(xii) repeating/cycling steps (ix)-(xi) one or more times to self-replicate and amplify multimers of nucleic acid origami tiles.

Origami tiles composed of nucleic acids are well known in the art since the publication of Rothemund (2006). As used herein, a nucleic acid origami tile is formed into a particular pattern (e.g., polygons and polygonal lattices) using a scaffold strand (most typically, but not necessarily, a large scaffold strand such as a M13 single-stranded form (~7250 nucleotide genome)) by 'staple strands', e.g., 200-250 'staple strands' with the M13 genomic DNA as the scaffold strand. Preferably, the origami tile is a DNA origami tile. The nucleic acid origami tile can be designed and the sequences generated by, for example, a software program caDNAno 1 (Douglas et al., 2009).

While the nucleic acid origami tile may be two or three dimensional, it is preferred that the nucleic acid origami tile is "substantially" two dimensional, i.e., where the third dimension is very small or negligible compared to the other two dimensions, such as one having a planar appearance (length and breadth but no depth). Top and bottom surfaces of the plane are also referred to herein as "faces" or "sides" ending at the "edges", which are the outer boundaries of the planar structure. Accordingly, a substantially two dimensional origami tile has two surfaces (a top and a bottom surface) with a plurality of "edges" that form the outer boundaries of the surfaces, e.g., four edges in a rectangular two dimensional origami tile. Preferably, the origami tile is rectangular.

The size of a nucleic acid origami tile mainly depends on the length of the scaffold strand used. Most often used and preferred is a scaffold strand in the 5-10 kb range, such as an M13 genomic DNA strand. It has been reported that a scaffold strand of 26 kb in length has been used successfully (Zhang et al., 2012).

The staple strands used together with the scaffold to form the origami tile into a particular pattern may have other features, like hairpins visible in the AFM or dyes like the ones used in the selection process disclosed below, or just stick ends, or perhaps nothing beyond the complementarity to the scaffold.

In the present invention, a nucleic acid origami tile is used as a single monomeric unit (monomer) for the purpose of forming multimers of nucleic acid origami tiles that can self-replicate. The joining/linking of monomers into a multimer is through sticky end cohesion, which involves single stranded nucleic acid ends (cohesive sticky ends) on a monomer that have sequence complementarity with the corresponding single stranded nucleic acid ends on another monomer so as to anneal the single stranded nucleic acid ends together by cohesion. The sticky ends on the monomers are single-stranded nucleic acid protruding both from the edges (horizontally; herein designated has horizontal sticky ends) and in one direction roughly perpendicular to one of the flat surfaces itself (herein designated as vertical sticky ends). When multimers are formed by horizontal sticky end cohesion between sticky ends on the edges of monomers and there is vertical sticky end cohesion between multimers, then this is termed "stacked multimers", where in the case of substantially two dimensional monomers and multimers, a stacked multimer is one where two monomers form two parallel planes, one stacked over the other.

There are a plurality of horizontal and vertical sticky cohesive ends on at least one edge and on one face of nucleic acid monomeric tile. As a preferred embodiment, there are eight horizontal sticky cohesive ends on one edge and eight vertical sticky cohesive ends on one face of the seed tile. In this same preferred embodiment, there are six horizontal sticky cohesive ends on one edge and eight vertical sticky cohesive ends on one face of the first generation (1G) and second generation (2G) tiles. Preferably, the design of the sticky cohesive ends allows the horizontal sticky cohesive ends of the seed to remain stably annealed at a high temperature such as at least 50° C. (e.g., the melting temperature Tm of the horizontal sticky cohesive ends on the seed tiles are at least 55° C.), whereas the vertical sticky cohesive ends have a Tm that is at least 15° C. lower. This allows, for instance, the horizontal sticky end cohesion between seed monomers to be stable at a temperature of 55° C. whereas the denaturation of the vertical sticky end cohesion between different generation of multimers (e.g., between seed and 1G, between 1G and 2G) is complete at 40° C. The sticky cohesive ends on daughter 1G and 2G tiles are also shorter than those ends on seed tiles so that daughter cannot form multimers of daughter tiles without the aid of templates in the temperature range of cycling in the present method, such as 4° C. to 50° C. It is only when monomers of daughter 1G tiles are immobilized on a multimer of seed tiles acting as template that adjacent monomers of daughter 1G tiles are subject to a greatly increased local concentration of daughter 1G tiles, thereby leading to formation of stable horizontal sticky end cohesion between adjacent monomers of daughter tiles.

The covalent linking of adjacent 1G or 2G monomers in a 1G or 2G multimer is preferably by photo-crosslinking. Such photo-crosslinking is well known and available in the art. Non-limiting examples includes photo-crosslinking with a nucleotide functionalized with 3-cyanovinylcarbazole (CNV), psoralen or cinnamate molecules. A nucleotide functionalized with such a molecule can react when exposed to ultraviolet light to form a covalent bond with the base on the opposing sticky cohesive end to which it was initially annealed by hydrogen bonding.

As will be appreciated by those of skill in the art from studying the embodiment in the Example shown in FIGS. 1a and 1c that, for purposes of being able to visualize successive generations by atomic force microscopy (AFM), the seed and later generation tiles are arbitrarily provided with differences in raised projections on the surface so as to be distinguishable using AFM. Furthermore, there are slight differences in the sequences of the sticky cohesive ends in order to allow monomers of the same generation to join to each other by horizontal sticky end cohesion and for monomers and multimers of different generations (e.g., seed with 1G, 1G with 2G) to join to each other by vertical sticky end cohesion to ultimately form the stacked multimers. Nevertheless, for practical purposes, it is the particular sequence and structure of the multimeric origami tile itself along with pendant molecules or moieties that are disposed on its surface (as opposed to the sequences of the sticky cohesive ends that are merely to facilitate the joining of monomers and multimers) that are considered to be replicated in the present self-replication process.

The present method of self-replication of a multimer of nucleic acid origami tiles can also be used to selectively amplify one or more different multimers from a pool of various monomers of different sets of seed, 1G and 2G daughter tiles so they outgrow their competitors (other competing multimers). For selective amplication, the monomers each have a sticky cohesive end, which is necessary for forming a multimer, labeled with a different dye (e.g., near-infrared) that produces light-activated local heat generation at a specific wavelength that is different from those of the dyes on competing monomers and multimers of the other sets of tiles. The tiles are irradiated at one or more different wavelengths to effect light-activated local heat generation in the vicinity of a particular dye or dyes, thereby suppressing sticky end cohesion of competing monomers labeled with dyes that are light-activated/absorbing at the one or more wavelengths to selectively amplify a multimer in which sticky end cohesion is not suppressed. Thus, the non-absorbing progeny replicates preferentially, and thereby takes over the system.

The term "nucleic acid" as used herein is any polymeric system containing a sequence of "nucleotides", where individual nucleotides are capable of forming highly specific paired interaction with other nucleotides, i.e., they form weak bonds with some nucleotides, vanishingly weak bonds with others, or they may even repel some other nucleotides. The interactions or bonds between nucleotides must be weak enough to be broken individually but strong enough that the cooperative action of a few neighbors forms a stable hybrid. A feature of the nucleotides is that they are capable of interacting with a nucleotide opposing them to form a specifically paired attraction. In natural DNA and RNA, hydrogen bonding forms this interaction. Non-limiting examples of nucleic acids include DNA, RNA, Peptide Nucleic Acid (PNA), and Locked Nucleic Action (LNA). A review of some nucleic acid variations, including derivatized/modified bases and other unusual bases, is presented in Freier et al. (1997).

It should also be appreciated that the term "nucleic acid" refers to both DNA and RNA and hybrids of the two. The structure need not resemble anything which can theoretically be made from nature. For example, one or more strands may contain PNA or other backbone molecules (Lukeman et al., 2004). A particular oligonucleotide or polynucleotide strand may employ bases other than the standard five, adenine, cytosine, guanine, thymine and uracil. Derivatized (e.g., methylated) and other unusual bases such as iso-guanine, iso-cytosine, amino-adenine, K, X, π, (Piccirilli et al., 1990), inosine and other derivatives of purine and pyrimidine may be used. A preferable feature in the selection of the bases is that they be capable of interacting with a base opposing them to form a specifically paired attraction. In natural DNA and RNA, hydrogen bonding forms this interaction. However, opposite ion charges, hydrophobic interactions and van der Waals forces may also be acceptable forms of interaction. These interactions expand the choices over naturally occurring bases to give a wider assortment of physical properties.

Within a particular strand, the heterocyclic base may be entirely missing from the sugar moiety. This may be particularly desirable where the strands bend, form a junction, or where one desires fewer forces holding the strands together.

A particular strand need not have a single contiguous ribose-phosphate or deoxyribose-phosphate backbone. It could be a peptide nucleic acid with a peptide backbone. One may employ a simple inorganic or organic moiety or polymeric spacer between segments of polynucleotide. Spacers such as polyethylene, polyvinyl polymers, polypropylene, polyethylene glycol, polystyrene, polypeptides (enzymes, antibodies, etc.) peptide nucleic acids (PNA), polysaccharides (starches, cellulose, etc.) silicones, silanes and copolymers, etc., may be employed. An example of such a hybrid structure is dodecadiol having phophoramidite at one end. This structure has been inserted covalently instead of four T nucleotides to form a hairpin loop in a fashion similar to the nucleotides it replaces. See Mitchel J. Doktycz, Ph.D. Thesis (1991), University of Illinois, Chicago.

In nature and in the field of molecular biology, double stranded DNA generally occurs in the B form. However, for the purposes of this invention, it may be desirable for DNA or other double stranded polynucleotide to exist in the A, C, D or Z form. Various bases, derivations and modifications may be used to stabilize the structure in the A, C, D or Z form as well.

A nanoparticle (e.g., gold (Au) or CdSe) and/or a pendant molecule can be attached to the surface of a monomeric tile. The pendant molecule can be small molecules, catalysts, enzymes, peptides and other proteins, i.e., ribosomes, (Niemeyer et al., 1994). Such attachment is not limited to direct attachment to the surface of the tile itself but may be through hairpins protruding from the surface of the tile or via attachment to oligonucleotides that bind to the surface of the tile or to hairpins or single stranded protrusions from the surface of the tile.

The self-replication of the nucleic acid origami tiles provides a way of producing multimers of the same monomeric unit or a combination of different monomeric units with greater ease by exponential amplification. Origami tiles have found utility in controlled release of drugs (Zhao et al., 2012; Cho et al., 2014), and there is a use for exponential amplification as a means of producing origami tiles carrying a drug.

Having now generally described the invention, the same will be more readily understood through reference to the following example which is provided by way of illustration and is not intended to be limiting of the present invention.

EXAMPLE

Materials and Methods
  DNA Strand Design, Synthesis, and Purification.
  The DNA origami was designed and the sequences were generated by program caDNAno 1 (Douglas et al., 2009). DNA sequences of sticky ends were generated using the program Uniquimer (Wei et al., 2007). Single-stranded M13mp18 DNA genome was purchased from Bayou Biolabs. 3-Cyanovinylcarbazole phosphoramidite ($^{CNV}K$) was purchased from Glen Research. IRDye 700 and IRDye 800 phosphoriamidites were purchased from LI-COR Biosciences. The DNA strands with modifications ($^{CNV}K$ or IR dyes) were synthesized on an Applied Biosystems 394 DNA synthesizer. Other DNA strands were purchased from Integrated DNA Technology, Inc. (idtdna.com). All the sticky-end-containing strands were purified using denaturing PAGE gel electrophoresis. The designed origami tiles are all based on using the genomic M13mp18 DNA (SEQ ID NO:344) as a scaffold to which 216 staple strands (Table 1; SEQ ID NO:1-216) anneal to form the origami base tile structure without any modifications (no hairpin structures and sticky ends). This origami base structure that is used for all the different types of origami tile structures used in this Example is shown in FIGS. 5A-5D. The origami base structure is shown split into four quadrants (FIGS. 5A-5D) with sufficient overlap between adjacent quadrants so that the entire origami structure can be determined and more easily visualized for clarity. The extra four "T" shown at both the 5' and 3' ends of staple strands 9, 10, 27, 28, 45, 46, 63, 64, 81, 82, 99, 100, 116, 117, 134, 135, 152, 153, 170, 171, 188, 189, 204 and 205 in Table 1 but not shown in FIGS. 5A-5D, are designed merely to prevent origami tiles from aggregating or binding to each other due to non-specific stacking interactions in the helical direction.

TABLE 1

Sequences of Regular Origami Staple Strands

| Number | Sequence | SEQ ID NO: |
|---|---|---|
| 1 | TTCTTTGATTAGTAATTATCGGCCTTGCTGGTACACGACC | SEQ ID NO: 1 |
| 2 | GCAAATTATTACCGCCAGCCATTGATGGATTA | SEQ ID NO: 2 |
| 3 | GAGGCCACCATGGAAATACCTTTCCAGTCGGG | SEQ ID NO: 3 |
| 4 | CCAGAATCCGTGCCAGCTGCATTAAGCTAACT | SEQ ID NO: 4 |

TABLE 1-continued

Sequences of Regular Origami Staple Strands

| Number | Sequence | SEQ ID NO: |
|---|---|---|
| 5 | GAAAAACCGCGGGGAGAGGCGGTTTAAAGTGT | SEQ ID NO: 5 |
| 6 | ATTAAAGAGGGTGGTTTTTCTTTTCACAATTC | SEQ ID NO: 6 |
| 7 | AGTGTTGTAACAGCTGATTGCCCTTAGCTGTT | SEQ ID NO: 7 |
| 8 | ATAAATCAAGAGAGTTGCAGCAAGGGGTACCG | SEQ ID NO: 8 |
| 9 | TTTTATCCTGTTTGATGGTGGCCCCAGCAGGCGAAATTTT | SEQ ID NO: 9 |
| 10 | TTTTGTAGAAGAACTCAAACAACATCACTTGCCTGATTTT | SEQ ID NO: 10 |
| 11 | AAAACGCTCGAGTAAAAGAGTCTGTCCATCAC | SEQ ID NO: 11 |
| 12 | AAACCTGTCTGAGAAGTGTTTTTATAATCAGT | SEQ ID NO: 12 |
| 13 | GCCAACGCGTCTATCAAGACAGGAACGGTACG | SEQ ID NO: 13 |
| 14 | GGGCGCCAACGTGGACTCCAACGTCAAAGGGC | SEQ ID NO: 14 |
| 15 | AGACGGGCTCCAGTTTGGAACAAGAGTCCACT | SEQ ID NO: 15 |
| 16 | TGGCCCTGAAAGAATAGCCCGAGATAGGGTTG | SEQ ID NO: 16 |
| 17 | GCTGGTTTGTTCCGAAATCGGCAAAATCCCTT | SEQ ID NO: 17 |
| 18 | AGTAATAATTCTGACCTGAAAGCGAACTAATA | SEQ ID NO: 18 |
| 19 | CACCAGTCAATATCCAGAACAATAACCGTTGTAGCAATAC | SEQ ID NO: 19 |
| 20 | TTTACATTAGACAATATTTTTGAAAGGTTATC | SEQ ID NO: 20 |
| 21 | CGCTCACTGCCCGCTACATTTTGAATGCGCGA | SEQ ID NO: 21 |
| 22 | CACATTAATTAAAAATACCGAACGAAATATCA | SEQ ID NO: 22 |
| 23 | AAAGCCTGTAAAACAGAGGTGAGGGAAAAATC | SEQ ID NO: 23 |
| 24 | CACACAACCGCCTGCAACAGCCAGCTGGCGAA | SEQ ID NO: 24 |
| 25 | TCCTGTGTGTGCTGCAAGGCGATTTGGGAAGG | SEQ ID NO: 25 |
| 26 | AGCTCGAAGGGTTTTCCCAGTCACAGCGCCAT | SEQ ID NO: 26 |
| 27 | TTTTGCATGCCTGCAGGTCGGGCCAGTGCCAAGCTTTTTT | SEQ ID NO: 27 |
| 28 | TTTTAACAGAGATAGAACCCAAGGGACATTCTGGCCTTTT | SEQ ID NO: 28 |
| 29 | AGTCTTTACGCTCAATCGTCTGAACAACAGGA | SEQ ID NO: 29 |
| 30 | ACTGATAGTTGGCAAATCAACAGTTTAAAAGT | SEQ ID NO: 30 |
| 31 | GCAGAAGAGGGTGCCTAATGAGTGATGAATCG | SEQ ID NO: 31 |
| 32 | ATTAACACATACGAGCCGGAAGCATGCGTATT | SEQ ID NO: 32 |
| 33 | AGGGGGATGAAATTGTTATCCGCTCACCAGTG | SEQ ID NO: 33 |
| 34 | TAACGCCATTCGTAATCATGGTCATCACCGCC | SEQ ID NO: 34 |
| 35 | AAAACGACACTCTAGAGGATCCCCCGGTCCAC | SEQ ID NO: 35 |
| 36 | GATTAGAGAGTATTAGACTTTACAAATAATGG | SEQ ID NO: 36 |
| 37 | GCACTAACTAAGAATACGTGGCACGGCAGATT | SEQ ID NO: 37 |
| 38 | TAAAATATGTATTAAATCCTTTGCATATAATC | SEQ ID NO: 38 |
| 39 | CTGGTCAGCCCTAAAACATCGCCATTGCGTTG | SEQ ID NO: 39 |
| 40 | AACCCTCAAACAAAGAAACGAGCGAGTAACAA | SEQ ID NO: 40 |
| 41 | TAAAGCATATTCTCCGTGGGAACAGGCCTTCC | SEQ ID NO: 41 |
| 42 | TCTTCGCTATTACGTGCCACGCTGTAATGGGA | SEQ ID NO: 42 |

TABLE 1-continued

Sequences of Regular Origami Staple Strands

| Number | Sequence | SEQ ID NO: |
|---|---|---|
| 43 | GCGATCGGGCATCGTAACCGTGCA | SEQ ID NO: 43 |
| 44 | TCGCCATTGACGACGACAGTATCGGTAAACGT | SEQ ID NO: 44 |
| 45 | TTTTCGGCACCGCTTCTGGTACTCCAGCCAGCTTTCTTTT | SEQ ID NO: 45 |
| 46 | TTTTCATTTGAGGATTTAGACCGTCAATAGATAATATTTT | SEQ ID NO: 46 |
| 47 | TATTAATTTGAAAGGAATTGAGGATGGCTATT | SEQ ID NO: 47 |
| 48 | TTGAGTAAATTCCTGATTATCAGACCTTTTAC | SEQ ID NO: 48 |
| 49 | CCCGTCGGCACCTTGCTGAACCTCAACCACCA | SEQ ID NO: 49 |
| 50 | ATTGACCGAGAGCCAGCAGCAAATCGGTCAGT | SEQ ID NO: 50 |
| 51 | TAGGTCACAATAGGAACGCCATCATGAGCAAA | SEQ ID NO: 51 |
| 52 | TTTGAGGGCAGGCTGCGCAACTGTAAGTTGGG | SEQ ID NO: 52 |
| 53 | AAGATCGCGCCGGAAACCAGGCAAGACGTTGT | SEQ ID NO: 53 |
| 54 | AAGGGTTAAACAGAAATAAAGAAAAATCATAG | SEQ ID NO: 54 |
| 55 | TACTTCTGAACAATTCGACAACTCCTTTAGGA | SEQ ID NO: 55 |
| 56 | CTGATTGTGTTTAACGTCAGATGAACGCTGAG | SEQ ID NO: 56 |
| 57 | ATCATCATCATTATCATTTTGCGGATCAATAT | SEQ ID NO: 57 |
| 58 | CAACATTAAATGTCACCAGAAGGAGCCTGATT | SEQ ID NO: 58 |
| 59 | TGTAGCCACGCGCAGAGGCGAATTAATATATG | SEQ ID NO: 59 |
| 60 | TTTTAACCGTTGGTGTAGATGGGCTGCGGGCC | SEQ ID NO: 60 |
| 61 | AAATTTTTGTTAAATCGAAAACAAAATTGAACGGTAATCG | SEQ ID NO: 61 |
| 62 | TAATATTTGCATGTCAATCATATGTCATTGCC | SEQ ID NO: 62 |
| 63 | TTTTACAGGAAGATTGTATACAGAAAAGCCCCAAAATTTT | SEQ ID NO: 63 |
| 64 | TTTTAATTATTTGCACGTAAGAACCTACCATATCAATTTT | SEQ ID NO: 64 |
| 65 | TAACAGTATGATGGCAATTCATCACCGAACGT | SEQ ID NO: 65 |
| 66 | ATCGGGAGTCCTTGAAAACATAGCTTTCAAAT | SEQ ID NO: 66 |
| 67 | GCTTTGAAAATCGTCGCTATTAATAGCCTTTA | SEQ ID NO: 67 |
| 68 | CAATTACCAAAATAATTCGCGTCTAACGGCGG | SEQ ID NO: 68 |
| 69 | AGAAGATGTTACCTTTTTAATGGGAGTAATG | SEQ ID NO: 69 |
| 70 | TAAAACTATGTTAAAATTCGCATTTCTGCCAG | SEQ ID NO: 70 |
| 71 | TTGATAATAGCAAATATTTAAATTGCCTCAGG | SEQ ID NO: 71 |
| 72 | GTCTGAGATTATATAACTATATGTATAAACAC | SEQ ID NO: 72 |
| 73 | TTTATCAATTGCGTAGATTTTCAGTTGGATTA | SEQ ID NO: 73 |
| 74 | AAGAGTCACCAATCGCAAGACAAACGACCGTG | SEQ ID NO: 74 |
| 75 | CCTTAGAAAAACAATAACGGATTCGCGGAATT | SEQ ID NO: 75 |
| 76 | CTTCTGTATACCAAGTTACAAAATGCTTTCAT | SEQ ID NO: 76 |
| 77 | TGAGTGAATAGAACCCTCATATATAAGCCTCA | SEQ ID NO: 77 |
| 78 | CATTTGAAATGAAACAAACATCAAAGCTCATT | SEQ ID NO: 78 |
| 79 | ACAAGAGAATCGATAATTACATTTAGAAAGGC | SEQ ID NO: 79 |
| 80 | TGAGAGTCTATGATATTCAACCGTGAGCTGAA | SEQ ID NO: 80 |

TABLE 1-continued

Sequences of Regular Origami Staple Strands

| Number | Sequence | SEQ ID NO: |
|--------|----------|------------|
| 81 | TTTTCTATTTTTGAGAGATCATGCCGGAGAGGGTAGTTTT | SEQ ID NO: 81 |
| 82 | TTTTTCCGGCTTAGGTTGGGGACTACCTTTTTAACCTTTT | SEQ ID NO: 82 |
| 83 | GAAAACTTGATAGCTTAGATTAAGATATACAG | SEQ ID NO: 83 |
| 84 | ATATTTTAGTTAATTTGCGGGAGATAATTTTC | SEQ ID NO: 84 |
| 85 | TTTCAACGCCAAAAACATTATGACCAGAGGCA | SEQ ID NO: 85 |
| 86 | CAATGCCTAAACAGTACATAAATCATTCATTT | SEQ ID NO: 86 |
| 87 | TGTAGGTAGCAAGGCAAAGAATTATCCAGACG | SEQ ID NO: 87 |
| 88 | CGGAGACAGTAGTAGCATTAACATTTCCATAT | SEQ ID NO: 88 |
| 89 | ATAAATTATACAAAGGCTATCAGGTACCCCGG | SEQ ID NO: 89 |
| 90 | CGGAATCATGCGTTATACAAATTCTATTTTCATCGTAGGA | SEQ ID NO: 90 |
| 91 | AAATAAGAAAATGCTGATGCAAATATAGTGAA | SEQ ID NO: 91 |
| 92 | TGATAAATAACGCTCAACAGTAGGACCGCACT | SEQ ID NO: 92 |
| 93 | CCTAAATTCCATATTTAACAACGCTTATCATT | SEQ ID NO: 93 |
| 94 | CGGTTGTACAAGGATAAAATTTTTAACCTTG | SEQ ID NO: 94 |
| 95 | GAGCATAAATAAAGTACCGACAAAAAAAATAA | SEQ ID NO: 95 |
| 96 | TCATACAGAAGATTCAAAAGGGTGAACAATTT | SEQ ID NO: 96 |
| 97 | TACTAATAGTCAAATCACCATCAATGGAGCAA | SEQ ID NO: 97 |
| 98 | AAGGTGGCACGAGTAGATTTAGTTTCAACATG | SEQ ID NO: 98 |
| 99 | TTTTAACCTGTTTAGCTATATTCGCAAATGGTCAATTTTT | SEQ ID NO: 99 |
| 100 | TTTTCCTGTTTAGTATCATATAATTACTAGAAAAAGTTTT | SEQ ID NO: 100 |
| 101 | GAGAATCGTAATGGTTTGAAATACGAACGCGA | SEQ ID NO: 101 |
| 102 | AATTTAGGCCTGTAATACTTTTCATCTTCTGA | SEQ ID NO: 102 |
| 103 | TTTTCGAGGTAGAAACCAATCAATGTCAGAAG | SEQ ID NO: 103 |
| 104 | TAATTCTGGCAAAATTAAGCAATATTTAAATG | SEQ ID NO: 104 |
| 105 | ACGACAATTGTTTATCAACAATAGGTTTTAAT | SEQ ID NO: 105 |
| 106 | AACAGTTGGTGTCTGGAAGTTTCAGGAAGCAA | SEQ ID NO: 106 |
| 107 | AGATACATTTTCATTTGGGCGCTCTAGCTG | SEQ ID NO: 107 |
| 108 | GCCGTTTTTTACCAGTATAAAGCCAAGGCGTT | SEQ ID NO: 108 |
| 109 | CATCGAGATAAACAGTTCAGAAAAATCGTCAT | SEQ ID NO: 109 |
| 110 | CCAAGAACTCAAAAATCAGGTCTTTGTTTAGA | SEQ ID NO: 110 |
| 111 | ACGAGCATCCAGTAATAAGAGAATAGCTAAAT | SEQ ID NO: 111 |
| 112 | TATCCCATTAAGAGGAAGCCCGAAATAAAAAC | SEQ ID NO: 112 |
| 113 | AACGCGCCAAACAACATGTTCAGCCCAATAAA | SEQ ID NO: 113 |
| 114 | AAAGTACGATTCCCAATTCTGCGAATCAATTC | SEQ ID NO: 114 |
| 115 | TTTTAAATGTACCTTTAATTGCTCAATACCAC | SEQ ID NO: 115 |
| 116 | TTTTTAGAGCTTAATTGCTGATTTTGCGGATGGCTTTTT | SEQ ID NO: 116 |
| 117 | TTTTATAGCAAGCAAATCAGATCATTACCGCGCCCATTTT | SEQ ID NO: 117 |
| 118 | ATATAGAAGGCTTATCCGGTACTCAAATGCTTACAAGCAA | SEQ ID NO: 118 |

TABLE 1-continued

Sequences of Regular Origami Staple Strands

| Number | Sequence | SEQ ID NO: |
|---|---|---|
| 119 | ACCATAAAGGGTATTAAACCAAGTGCTTAATT | SEQ ID NO: 119 |
| 120 | CTATTATAAATCGGCTGTCTTTCCCAACATGT | SEQ ID NO: 120 |
| 121 | CAAAGCGGAAGAAGTTTTGCCAGACCAGTTAC | SEQ ID NO: 121 |
| 122 | AATATCGCATAAGTCCTGAACAAGAGGTAAAG | SEQ ID NO: 122 |
| 123 | TCGAGCTTACACTATCATAACCCTTAATCATT | SEQ ID NO: 123 |
| 124 | ACTCCAACGCCAAAAGGAATTACGGAACTGGC | SEQ ID NO: 124 |
| 125 | AAGAGGTCAATATAATGCTGTAGCTGACCATT | SEQ ID NO: 125 |
| 126 | AGGCGTTTAGCCTTAAATCAAGATGGTAATTG | SEQ ID NO: 126 |
| 127 | AAATATTCCCCAGCTACAATTTTAGAATTAAC | SEQ ID NO: 127 |
| 128 | CTGGATAGCGCTAACGAGCGTCTTAACATAAA | SEQ ID NO: 128 |
| 129 | TTTTGCAAATTGCATCAAAAAGATCCTAATTT | SEQ ID NO: 129 |
| 130 | CAAAATAGCCCAATCCAAAGAGATGGTTTAAT | SEQ ID NO: 130 |
| 131 | TAAGAGCACAAAGCGAACCAGACCTAATGCAG | SEQ ID NO: 131 |
| 132 | TACATAACAGGTCAGGATTAGAGAATGCAACT | SEQ ID NO: 132 |
| 133 | ATTCAACTGAAGAAAAATCTACGTAACCGGAT | SEQ ID NO: 133 |
| 134 | TTTTCAGGTAGAAAGATTCACGGAACAACATTATTATTTT | SEQ ID NO: 134 |
| 135 | TTTTTTGCGGGAGGTTTTGATAGCGAACCTCCCGACTTTT | SEQ ID NO: 135 |
| 136 | ATTTTGCAATTGAATCCCCTTCTAAGAACGCG | SEQ ID NO: 136 |
| 137 | CTTACCAACGTCCAATACTGCGGACGAGAATG | SEQ ID NO: 137 |
| 138 | CTAATTTGGGGGGTAATAGTAAAATACCCTGA | SEQ ID NO: 138 |
| 139 | AAAATAAAAAAATGAAAATAGCAGCGCGAAAC | SEQ ID NO: 139 |
| 140 | TTCAACTTCGTTTACCAGACGACGAGACTTCA | SEQ ID NO: 140 |
| 141 | GTGAATTATGACGAGAAACACCAGTGCTCCAT | SEQ ID NO: 141 |
| 142 | TCATTATAAAAGCTGCTCATTCAGGACGGTCA | SEQ ID NO: 142 |
| 143 | CGAACTAATCAGTTGAGATTTAGGCTTTTGAT | SEQ ID NO: 143 |
| 144 | AGCGCTAAAGCCCAATAATAAGAGAACGCAAT | SEQ ID NO: 144 |
| 145 | TGAACACCAGCAATAGCTATCTTAGCCGAACA | SEQ ID NO: 145 |
| 146 | AACAGGGAACTCATCTTTGACCCCAAGAATAC | SEQ ID NO: 146 |
| 147 | TAACGTCACAGCCATATTATTTATCGAGAGGC | SEQ ID NO: 147 |
| 148 | GTAAATTGGGCTTTAAGAAACGATTCGCCTGA | SEQ ID NO: 148 |
| 149 | GCTTGCCCCCTTATGCGATTTTAAAGGCATAG | SEQ ID NO: 149 |
| 150 | AACGTAACCCAGTCAGGACGTTGGAATGCAGA | SEQ ID NO: 150 |
| 151 | ATTCATTAACTTTGAAAGAGGACAGGGATCGT | SEQ ID NO: 151 |
| 152 | TTTTGGCTGACCTTCATCAAACCAGGCGCATAGGCTTTTT | SEQ ID NO: 152 |
| 153 | TTTTCACAAGAATTGAGTTATATCAGAGAGATAACCTTTT | SEQ ID NO: 153 |
| 154 | AATGAAATCTGAACAAAGTCAGAGTAGTTGCT | SEQ ID NO: 154 |
| 155 | CTTTTTAAAGCGCATTAGACGGGATCCTGAAT | SEQ ID NO: 155 |
| 156 | ATACCAAGCCTTTACAGAGAGAATTCCAGAGC | SEQ ID NO: 156 |

TABLE 1-continued

Sequences of Regular Origami Staple Strands

| Number | Sequence | SEQ ID NO: |
|---|---|---|
| 157 | AAAGTACAACGAAGGCACCAACCTGTCACAAT | SEQ ID NO: 157 |
| 158 | TAAATTGTTCCATTAAACGGGTAACAGCGCCA | SEQ ID NO: 158 |
| 159 | GTTACTTATTGAGGACTAAAGACTGATTGAGG | SEQ ID NO: 159 |
| 160 | ATCATAAGTCGGAACGAGGGTAGCATTATTCA | SEQ ID NO: 160 |
| 161 | GTGTACAGGAGTAATCTTGACAAGTAATAAAA | SEQ ID NO: 161 |
| 162 | AATAACGGCTTATTACGCAGTATGGAGCCACC | SEQ ID NO: 162 |
| 163 | AAGTTACCATACATACATAAAGGTCCATCTTT | SEQ ID NO: 163 |
| 164 | ACTAAAACAACGCAAAGACACCACATTTTCGG | SEQ ID NO: 164 |
| 165 | ATGCCACTACGGAGATTTGTATCATTTTTGTT | SEQ ID NO: 165 |
| 166 | AGGAAGTTGTCGAAATCCGCGACCAACGAGTA | SEQ ID NO: 166 |
| 167 | CAGAGGCTGCCGGAACGAGGCGCATGAATAAG | SEQ ID NO: 167 |
| 168 | AGACAGCAGGAACCGAACTGACCACCCAAATC | SEQ ID NO: 168 |
| 169 | CACCCTCACGACTTGAGCCAACCATCGCCCAC | SEQ ID NO: 169 |
| 170 | TTTTGAGGCTTGCAGGGAGTGATATATTCGGTCGCTTTTT | SEQ ID NO: 170 |
| 171 | TTTTGGCATGATTAAGACTCAATACCCAAAAGAACTTTTT | SEQ ID NO: 171 |
| 172 | CGTAGAAAAGAAGGAAACCGAGGACAAGAAAC | SEQ ID NO: 172 |
| 173 | ATAAAAGAGAAAAGTAAGCAGATACCGAAGCC | SEQ ID NO: 173 |
| 174 | TTTATTTTAAAACGAAAGAGGCAACAGCGATT | SEQ ID NO: 174 |
| 175 | CAATAGAATTAGCGTCAGACTGTAGTATGGGA | SEQ ID NO: 175 |
| 176 | AAGACAAACGTAATCAGTAGCGACTTCAGCGG | SEQ ID NO: 176 |
| 177 | GAGGGAAGAACGTCACCAATGAAAAAGGAATT | SEQ ID NO: 177 |
| 178 | TTAAAGGTCCAGTAGCACCATTACAAAATCTC | SEQ ID NO: 178 |
| 179 | GCATAACCTAAAGGCCGCTTTTGCGATGAACG | SEQ ID NO: 179 |
| 180 | ACCGGAACCCACCCTCAGAGCCACGAGGTTGA | SEQ ID NO: 180 |
| 181 | TCATAATCACCAGAACCACCGTAACGATCTAA | SEQ ID NO: 181 |
| 182 | TCATAGCCCGTCTTTCCAGACGTTACGCCTGTAGCATTCC | SEQ ID NO: 182 |
| 183 | GTTTGCCTAATTCATATGGTTTACAATACGTA | SEQ ID NO: 183 |
| 184 | AGCAGCACAGGGCGACATTCAACCTTTTCATG | SEQ ID NO: 184 |
| 185 | AGGCCGGAGTAAATATTGACGGAAAACGGCTA | SEQ ID NO: 185 |
| 186 | CAAAATCAGAATTATCACCGTCACGCAGCGAA | SEQ ID NO: 186 |
| 187 | CGACAATGACAACATTTGGGAATTCTTTAATT | SEQ ID NO: 187 |
| 188 | TTTTACAGCTTGATACCGATGAGGTGAATTTCTTAATTTT | SEQ ID NO: 188 |
| 189 | TTTTGCCACCCTCAGAACCGCGCCTCCCTCAGAGCCTTTT | SEQ ID NO: 189 |
| 190 | GAGCCGCCAAAATCACCGGAACCATTAGCAAA | SEQ ID NO: 190 |
| 191 | AGTTTTGTCCCTTATTAGCGTTTGGGCAACAT | SEQ ID NO: 191 |
| 192 | AATTTTCTGCGCGTTTTCATCGGCGGAATAAG | SEQ ID NO: 192 |
| 193 | TTTTGCTAAACACTGAGTTTCGTCAATAAGTT | SEQ ID NO: 193 |
| 194 | AGTGAGAAGATAGCAAGCCCAATAACAGTGCC | SEQ ID NO: 194 |

TABLE 1-continued

Sequences of Regular Origami Staple Strands

| Number | Sequence | SEQ ID NO: |
|---|---|---|
| 195 | GCGAATAACCACCCTCAGAGCCACCCTATTTCGGAACCTA | SEQ ID NO: 195 |
| 196 | CAAAAAAACGCCACCCTCAGAACCGCCACCCT | SEQ ID NO: 196 |
| 197 | GTATCGGTAGGTGTATCACCGTACGGATTAGG | SEQ ID NO: 197 |
| 198 | GGCAGGTCAATCCTCATTAAAGCCAGAATGGA | SEQ ID NO: 198 |
| 199 | ACAGACAGCCCTCATAGTTAGCACCAGAGCCGTCTCTGAATTTACCGT | SEQ ID NO: 199 |
| 200 | TGTACCGTAACAACTTTCAACAGTAGAATCAA | SEQ ID NO: 200 |
| 201 | TTTTCAGGTAGAAAGGAACAACTACCATCGAT | SEQ ID NO: 201 |
| 202 | CAGAACCGTAATTTTTTCACGTTGCATTAGCA | SEQ ID NO: 202 |
| 203 | TTTAGTACAGGCTCCAAAAGGAGCAGAGCCAG | SEQ ID NO: 203 |
| 204 | CCCGGAATTTATCAGCTTGCTTTCAGTTGCGC | SEQ ID NO: 204 |
| 205 | TTTTTCGAGAGGGTTGATATAGGCGGATAAGTGCCGTTTT | SEQ ID NO: 205 |
| 206 | TTTTTATTCACAAACAAATAAGACGATTGGCCTTGATTTT | SEQ ID NO: 206 |
| 207 | AAGCGCAGCCGCCAGCATTGACAGCACCCTCA | SEQ ID NO: 207 |
| 208 | TCCAGTAAGCGTCATA | SEQ ID NO: 208 |
| 209 | CATGGCTTTTGATGAT | SEQ ID NO: 209 |
| 210 | ACAGGAGTGTACTGGTACCAGTACAAACTACAAGTAAATG | SEQ ID NO: 210 |
| 211 | TTAACGGGGTCAGTGCCTTGAGTAGGAACCCA | SEQ ID NO: 211 |
| 212 | CGTATAAACAGTTAATGCCCCCTGCACCCTCA | SEQ ID NO: 212 |
| 213 | TTATTCTGAAACATGA | SEQ ID NO: 213 |
| 214 | AAGTATTAAGAGGCTG | SEQ ID NO: 214 |
| 215 | AGACTCCTCAAGAGAATCAGGAGG | SEQ ID NO: 215 |
| 216 | ATTAGCGGGGTTTTGCTCAGTACCAAGTATAG | SEQ ID NO: 216 |

Figure 6:
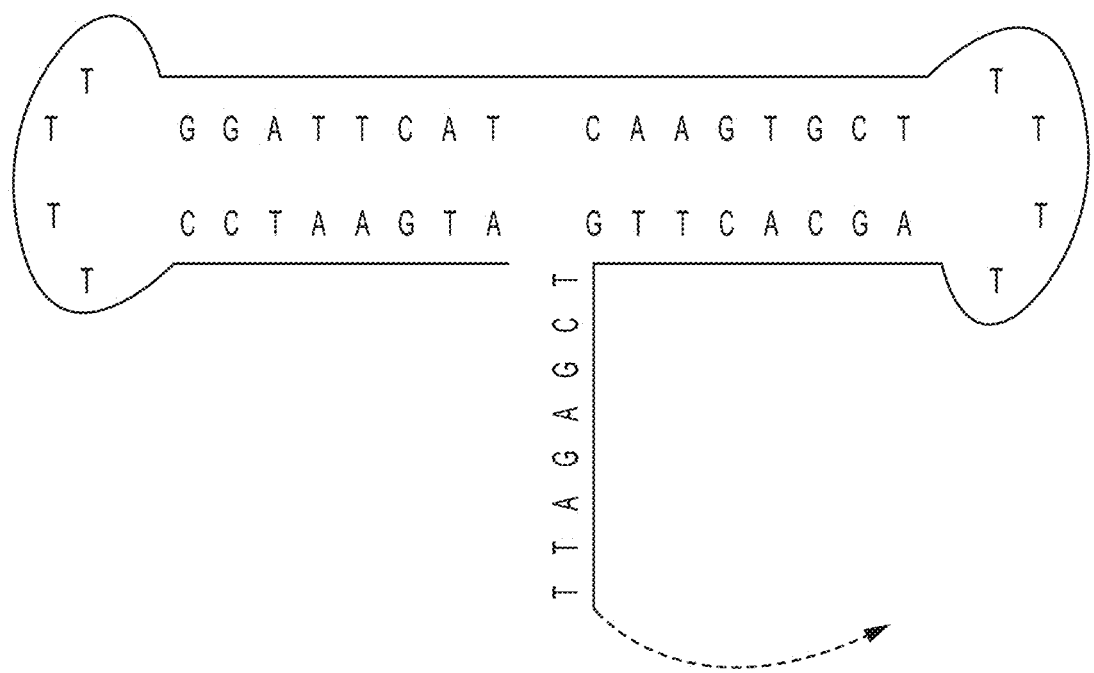
FIG. 6 schematically illustrates the structure of the DNA hairpin involved in producing letters (SEQ ID NO:345).

To label origami tiles for identification by AFM, DNA hairpins are added to increase the height of a desired location on the origami tile as shown in FIG. 6. The sequences of the hairpin modified staple strands involved in producing the letter "T" on the origami tile are shown in Table 2 below, where the nucleotides forming the hairpins are shown in lower case.

TABLE 2

Sequences of Staple Strands Involved in Producing the Letter T

| Label | Sequence | SEQ ID NO: |
|---|---|---|
| T-039 | atgaatccattggattcatcaagtgcttttagcacttgtcgagattCTGGTCAGCCCTAAAACATCGCCATTGCGTTG | SEQ ID NO: 217 |
| T-040-1 | AACCCTCAAACAAAGA | SEQ ID NO: 218 |
| T-040 | atgaatcatttggattcatcaagtgcttttagcacttgtcgagattAACGAGCGAGTAACAA | SEQ ID NO: 219 |
| T-041-1 | TAAAGCATATTCTCCG | SEQ ID NO: 220 |
| T-041 | atgaatccattggattcatcaagtgcttttagcacttgtcgagattTGGGAACAGGCCTTCCTGTAGCCACGCGCAGA | SEQ ID NO: 221 |
| T-042 | atgaatcatttggattcatcaagtgcttttagcacttgtcgagattTCTTCGCTATTACGTGCCACGCTGTAATGGGA | SEQ ID NO: 222 |
| T-049-1 | CCCGTCGGCACCTTGC | SEQ ID NO: 223 |

TABLE 2-continued

Sequences of Staple Strands Involved in Producing the Letter T

| Label | Sequence | SEQ ID NO: |
|---|---|---|
| T-049 | atgaatcatttggattcatcaagtgcttttagcacttgtcgagattTGAACCTCAACCACCA | SEQ ID NO: 224 |
| T-050-1 | ATTGACCGAGAGCCAG | SEQ ID NO: 225 |
| T-050 | atgaatccattggattcatcaagtgctattagcacttgtcgagattCAGCAAATCGGTCAGT | SEQ ID NO: 226 |
| T-051 | atgaatcatttggattcatcaagtgcttttagcacttgtcgagattTAGGTCACAATAGGAACGCCATCATGAGCAAA | SEQ ID NO: 227 |
| T-059 | atgaatcatttggattcatcaagtgcttttagcacttgtcgagattGGCGAATTAATATATGTGAGTGAATAGAACCC | SEQ ID NO: 228 |
| T-077 | atgaatcatttggattcatcaagtgcttttagcacttgtcgagattTCATATATAAGCCTCAGAGCATAAATAAAGTA | SEQ ID NO: 229 |
| T-095 | atgaatcatttggattcatcaagtgcttttagcacttgtcgagattCCGACAAAAAAATAATATCCCATTAAGAGGA | SEQ ID NO: 230 |
| T-112 | atgaatcatttggattcatcaagtgcttttagcacttgtcgagattAGCCCGAAATAAAACCAAAATAGCCCAATCC | SEQ ID NO: 231 |
| T-130 | atgaatcatttggattcatcaagtgcttttagcacttgtcgagattAAAGAGATGGTTTAAT | SEQ ID NO: 232 |
| T-158 | atgaatcatttggattcatcaagtgcttttagcacttgtcgagattTAAATTGTTCCATTAAACGGGTAACAGCGCCA | SEQ ID NO: 233 |
| T-176 | atgaatcatttggattcatcaagtgcttttagcacttgtcgagattAAGACAAACGTAATCAGTAGCGACTTCAGCGG | SEQ ID NO: 234 |

For an "I" pattern origami tile, the staple strands involved in producing the letter "T" in Table 2 above were used except that staple strands T-039, T-040, T-040-1, T-042, T-049, T-049-1, T-050, T-050-1 and T-051 are replaced with the regular staple strands with the same label numbers as shown in Table 1.

The sequences of the hairpin-modified staple strands involved in producing the letter "A" on the origami tile are shown in Table 3 below, where the nucleotides forming the hairpins are shown in lowercase.

TABLE 3

Sequences of Staple Strands Involved in Producing the Letter A

| Label | Sequence | SEQ ID NO: |
|---|---|---|
| A-023-1 | AAAGCCTGTAAAACAG | SEQ ID NO: 235 |
| A-023 | atgaatccttttggattcatcaagtgcttttagcacttgtcgagattAGGTGAGGGAAAAATC | SEQ ID NO: 236 |
| A-040-1 | AACCCTCAAACAAAGA | SEQ ID NO: 237 |
| A-040 | atgaatccttttggattcatcaagtgcttttagcacttgtcgagattAACGAGCGAGTAACAA | SEQ ID NO: 238 |
| A-049-1 | CCCGTCGGCACCTTGC | SEQ ID NO: 239 |
| A-049 | atgaatccttttggattcatcaagtgcttttagcacttgtcgagattTGAACCTCAACCACCA | SEQ ID NO: 240 |
| A-050-1 | ATTGACCGAGAGCCAG | SEQ ID NO: 241 |
| A-050 | atgaatccttttggattcatcaagtgcttttagcacttgtcgagattCAGCAAATCGGTCAGT | SEQ ID NO: 242 |
| A-051 | atgaatccttttggattcatcaagtgcttttagcacttgtcgagattTAGGTCACAATAGGAACGCCATCATGAGCAAA | SEQ ID NO: 243 |
| A-057 | atgaatccttttggattcatcaagtgcttttagcacttgtcgagattATCATCATCATTATCATTTTGCGGATCAATAT | SEQ ID NO: 244 |
| A-060 | atgaatccttttggattcatcaagtgcttttagcacttgtcgagattTTTTAACCGTTGGTGTAGATGGGCTGCGGGCC | SEQ ID NO: 245 |
| A-075 | atgaatccttttggattcatcaagtgcttttagcacttgtcgagattCCTTAGAAAAACAATAACGGATTCGCGGAATT | SEQ ID NO: 246 |
| A-078 | atgaatccttttggattcatcaagtgcttttagcacttgtcgagattCATTTGAAATGAAACAAACATCAAAGCTCATT | SEQ ID NO: 247 |

TABLE 3-continued

Sequences of Staple Strands Involved in Producing the Letter A

| Label | Sequence | SEQ ID NO: |
|---|---|---|
| A-096 | atgaatccttttggattcatcaagtgcttttagcacttgtcgagattTCATACAGAAGATTCAAAAGGGTGAACAATTT | SEQ ID NO: 248 |
| A-102 | atgaatccttttggattcatcaagtgcttttagcacttgtcgagattACTTTTCATCTTCTGA | SEQ ID NO: 249 |
| A-111 | atgaatccttttggattcatcaagtgcttttagcacttgtcgagattACGAGCATCCAGTAATAAGAGAATAGCTAAAT | SEQ ID NO: 250 |
| A-112-1 | TATCCCATTAAGAGGA | SEQ ID NO: 251 |
| A-112 | atgaatccttttggattcatcaagtgcttttagcacttgtcgagattAGCCCGAAATAAAAAC | SEQ ID NO: 252 |
| A-113 | atgaatccttttggattcatcaagtgcttttagcacttgtcgagattAACGCGCCAAACAACATGTTCAGCCCAATAAA | SEQ ID NO: 253 |
| A-120 | atgaatccttttggattcatcaagtgcttttagcacttgtcgagattGTCTTTCCCAACATGTAATTTAGGCCTGTAAT | SEQ ID NO: 254 |
| A-121 | atgaatccttttggattcatcaagtgcttttagcacttgtcgagattCAAAGCGGAAGAAGTTTTGCCAGACCAGTTAC | SEQ ID NO: 255 |
| A-122-1 | AATATCGCATAAGTCC | SEQ ID NO: 256 |
| A-122 | atgaatccttttggattcatcaagtgcttttagcacttgtcgagattTGAACAAGAGGTAAAG | SEQ ID NO: 257 |
| A-123 | atgaatccttttggattcatcaagtgcttttagcacttgtcgagattTCGAGCTTACACTATCATAACCCTTAATCATT | SEQ ID NO: 258 |
| A-131 | atgaatccttttggattcatcaagtgcttttagcacttgtcgagattTAAGAGCACAAAGCGAACCAGACCTAATGCAG | SEQ ID NO: 259 |
| A-138 | atgaatccttttggattcatcaagtgcttttagcacttgtcgagattTAGTAAAATACCCTGACTATTATAAATCGGCT | SEQ ID NO: 260 |
| A-149 | atgaatccttttggattcatcaagtgcttttagcacttgtcgagattGCTTGCCCCCTTATGCGATTTTAAAGGCATAG | SEQ ID NO: 261 |
| A-156-1 | ATACCAAGCCTTTACA | SEQ ID NO: 262 |
| A-156 | atgaatccttttggattcatcaagtgcttttagcacttgtcgagattGAGAGAATTCCAGAGCCTAATTTGGGGGGTAA | SEQ ID NO: 263 |

As for the locations of the hairpin-modified staple strands for the "H" pattern origami tile, the staple strands involved in producing the letter "A" were used, except that staple strands with hairpin sequences A-023, A-023-1, A-040, A-040-1, A-049, A-049-1, A-050, A-050-1 and A-050 were replaced with the regular staple strands with the same label numbers as shown in Table 1.

In order to connect two tiles together to form dimer seeds, some of the staple strands were modified to have sticky ends that protrude from the sides of the origami tile in the direction of the helices. The sequences of such modified staple strands are shown in Table 4 below, wherein the sticky end sequences are shown in lowercase.

TABLE 4

Sequences of horizontal sticky ends for dimer seed

| | | |
|---|---|---|
| Dimer-R-045 | TTTTCGGCACCGCTTCTGGTACTCCAGCCAGCTTTCtgtcgtggtca | SEQ ID NO: 264 |
| Dimer-R-063 | TTTTACAGGAAGATTGTATACAGAAAAGCCCCAAAAgcgcttcaata | SEQ ID NO: 265 |
| Dimer-R-081 | TTTTCTATTTTTGAGAGATCATGCCGGAGAGGGTAGcgcattcactt | SEQ ID NO: 266 |
| Dimer-R-099 | TTTTAACCTGTTTAGCTATATTCGCAAATGGTCAAtgggtcttcct | SEQ ID NO: 267 |
| Dimer-R-116 | TTTTTAGAGCTTAATTGCTGATTTTTGCGGATGGCTttattggcgtt | SEQ ID NO: 268 |
| Dimer-R-134 | TTTTCAGGTAGAAAGATTCACGGAACAACATTATTAggcttgttcga | SEQ ID NO: 269 |
| Dimer-R-152 | TTTTGGCTGACCTTCATCAAACCAGGCGCATAGGCTagtttccgtgc | SEQ ID NO: 270 |
| Dimer-R-170 | TTTTGAGGCTTGCAGGGAGTGATATATTCGGTCGCTaaccgagtatc | SEQ ID NO: 271 |
| Dimer-L-046 | TTTTCATTTGAGGATTTAGACCGTCAATAGATAATAtgaccacgaca | SEQ ID NO: 272 |

TABLE 4-continued

Sequences of horizontal sticky ends for dimer seed

| | | |
|---|---|---|
| Dimer-L-064 | TTTTAATTATTTGCACGTAAGAACCTACCATATCAAtattgaagcgc | SEQ ID NO: 273 |
| Dimer-L-082 | TTTTTCCGGCTTAGGTTGGGGACTACCTTTTTAACCaagtgaatgcg | SEQ ID NO: 274 |
| Dimer-L-100 | TTTTCCTGTTTAGTATCATATAATTACTAGAAAAAGaggaagaccca | SEQ ID NO: 275 |
| Dimer-L-117 | TTTTATAGCAAGCAAATCAGATCATTACCGCGCCCAaacgccaataa | SEQ ID NO: 276 |
| Dimer-L-135 | TTTTTTGCGGGAGGTTTTGATAGCGAACCTCCCGACtcgaacaagcc | SEQ ID NO: 277 |
| Dimer-L-153 | TTTTCACAAGAATTGAGTTATATCAGAGAGATAACCgcacggaaact | SEQ ID NO: 278 |
| Dimer-L-171 | TTTTGGCATGATTAAGACTCAATACCCAAAAGAACTgatactcggtt | SEQ ID NO: 279 |

There are two groups of vertical sticky-end pairs, with each vertical sticky end protruding perpendicularly from the surface/face (top or bottom) of an origami tile. For each set, strand 038 on the seed tile is complementary to strand 044 on the first generation tile (seed strand 038 to FG-044) and so on. One set was used on one unit tile (monomer) of seed in the dimer system. In order to ensure that the vertical sticky ends face up from the origami tile surface/face, complementary strands containing poly A sticky ends (black lines; see also Table 5 below), which would bind to the poly T segments of the vertical sticky ends. The sequences of the vertical sticky ends for the dimer seeds and first generation tiles are shown in Table 5 below.

TABLE 5

Sequences of vertical sticky ends for dimer seeds and first generation tiles

| | | SEQ ID NO: |
|---|---|---|
| Complementary strands to the poly T segment in vertical sticky ends | | |
| 9A-056 | AAAAAAAAACTGATTGTGTTTAACGTCAGATGAACGCTGAG | SEQ ID NO: 280 |
| 9A-092 | AAAAAAAAATGATAAATAACGCTCAACAGTAGGACCGCACT | SEQ ID NO: 281 |
| 9A-127 | AAAAAAAAAAATATTCCCCAGCTACAATTTTAGAATTAAC | SEQ ID NO: 282 |
| 9A-163 | AAAAAAAAAAGTTACCATACATACATAAAGGTCCATCTTT | SEQ ID NO: 283 |
| 9A-062 | AAAAAAAAATAATATTTGCATGTCAATCATATGTCATTGCC | SEQ ID NO: 284 |
| 9A-098 | AAAAAAAAAAGGTGGCACGAGTAGATTTAGTTTCAACATG | SEQ ID NO: 285 |
| 9A-133 | AAAAAAAAAATTCAACTGAAGAAAAATCTACGTAACCGGAT | SEQ ID NO: 286 |
| 9A-169 | AAAAAAAAACACCCTCACGACTTGAGCCAACCATCGCCCAC | SEQ ID NO: 287 |
| Vertical sticky ends (two sets) | | |
| 1-Seed-038 | TAAAATATGTATTAAATCCTTTGCATATAATCttttttttttatgagacgg | SEQ ID NO: 288 |
| 1-Seed-044 | TCGCCATTGACGACGACAGTATCGGTAAACGTttttttttttgtaggcagt | SEQ ID NO: 289 |
| 1-Seed-074 | AAGAGTCACCAATCGCAAGACAAACGACCGTGttttttttttcgtgttcag | SEQ ID NO: 290 |
| 1-Seed-080 | TGAGAGTCTATGATATTCAACCGTGAGCTGAAttttttttttcgtatgtgc | SEQ ID NO: 291 |
| 1-Seed-109 | CATCGAGATAAACAGTTCAGAAAAATCGTCATttttttttttcagcgttag | SEQ ID NO: 292 |
| 1-Seed-115 | TTTTAAATGTACCTTTAATTGCTCAATACCACttttttttttcttggttcg | SEQ ID NO: 293 |
| 1-Seed-145 | TGAACACCAGCAATAGCTATCTTAGCCGAACAttttttttttccattccga | SEQ ID NO: 294 |
| 1-Seed-151 | ATTCATTAACTTTGAAAGAGGACAGGGATCGTttttttttttggagagtcc | SEQ ID NO: 295 |
| 1-FG-038 | TAAAATATGTATTAAATCCTTTGCATATAATCttttttttttactgcctac | SEQ ID NO: 296 |
| 1-FG-044 | TCGCCATTGACGACGACAGTATCGGTAAACGTttttttttttccgtctcat | SEQ ID NO: 297 |
| 1-FG-074 | AAGAGTCACCAATCGCAAGACAAACGACCGTGttttttttttgcacatacg | SEQ ID NO: 298 |
| 1-FG-080 | TGAGAGTCTATGATATTCAACCGTGAGCTGAAttttttttttctgaacacg | SEQ ID NO: 299 |
| 1-FG-109 | CATCGAGATAAACAGTTCAGAAAAATCGTCATttttttttttcgaaccaag | SEQ ID NO: 300 |

TABLE 5-continued

Sequences of vertical sticky ends for dimer seeds and first generation tiles

| | | SEQ ID NO: |
|---|---|---|
| 1-FG-115 | TTTTAAATGTACCTTTAATTGCTCAATACCACttttttttttctaacgctg | SEQ ID NO: 301 |
| 1-FG-145 | TGAACACCAGCAATAGCTATCTTAGCCGAACAttttttttttggactctcc | SEQ ID NO: 302 |
| 1-FG-151 | ATTCATTAACTTTGAAAGAGGACAGGGATCGTttttttttttcggaatgg | SEQ ID NO: 303 |
| 2-Seed-038 | TAAAATATGTATTAAATCCTTTGCATATAATCttttttttttatgcaccc | SEQ ID NO: 304 |
| 2-Seed-044 | TCGCCATTGACGACGACAGTATCGGTAAACGTttttttttttatcgagtgc | SEQ ID NO: 305 |
| 2-Seed-074 | AAGAGTCACCAATCGCAAGACAAACGACCGTGttttttttttacctgggtc | SEQ ID NO: 306 |
| 2-Seed-080 | TGAGAGTCTATGATATTCAACCGTGAGCTGAAttttttttttggaaagtcg | SEQ ID NO: 307 |
| 2-Seed-109 | CATCGAGATAAACAGTTCAGAAAAATCGTCATttttttttttgcttcacg | SEQ ID NO: 308 |
| 2-Seed-115 | TTTTAAATGTACCTTTAATTGCTCAATACCACttttttttttagctgttgt | SEQ ID NO: 309 |
| 2-Seed-145 | TGAACACCAGCAATAGCTATCTTAGCCGAACAttttttttttcctcttgcc | SEQ ID NO: 310 |
| 2-Seed-151 | ATTCATTAACTTTGAAAGAGGACAGGGATCGTttttttttttgagcgattc | SEQ ID NO: 311 |
| 2-FG-038 | TAAAATATGTATTAAATCCTTTGCATATAATCttttttttttgcactcgat | SEQ ID NO: 312 |
| 2-FG-044 | TCGCCATTGACGACGACAGTATCGGTAAACGTttttttttttgggtgcata | SEQ ID NO: 313 |
| 2-FG-074 | AAGAGTCACCAATCGCAAGACAAACGACCGTGttttttttttcgactttcc | SEQ ID NO: 314 |
| 2-FG-080 | TGAGAGTCTATGATATTCAACCGTGAGCTGAAttttttttttgacccaggt | SEQ ID NO: 315 |
| 2-FG-109 | CATCGAGATAAACAGTTCAGAAAAATCGTCATttttttttttacaacagct | SEQ ID NO: 316 |
| 2-FG-115 | TTTTAAATGTACCTTTAATTGCTCAATACCACttttttttttcgtgaagca | SEQ ID NO: 317 |
| 2-FG-145 | TGAACACCAGCAATAGCTATCTTAGCCGAACAttttttttttgaatcgctc | SEQ ID NO: 318 |
| 2-FG-151 | ATTCATTAACTTTGAAAGAGGACAGGGATCGTttttttttttggcaagagg | SEQ ID NO: 319 |

Figures 7, 8A, 8B, 8C:
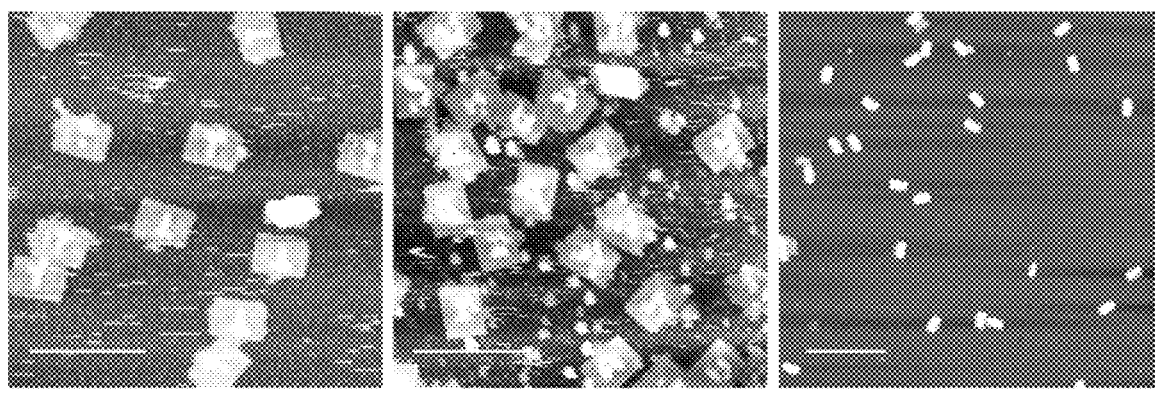
FIG. 7 shows sequences of horizontal sticky ends for first-generation (FG) tiles and second-generation (SG) tiles. Numbers on each generation tile are the label numbers of staple strands modified with horizontal sticky ends in the origami.
FIGS. 8A-8C show AFM images of the single origami tiles.

There are six sticky ends on both sides (at the ends of the DNA helices) of the first generation and second generation tiles, as shown in FIG. 7 of these six sticky ends on a side, four of them contain 3-cyanounylcarbazole nucleosides ($^{CNV}$K), labeled as "X" in FIG. 7, for photo-crosslinking. Under UV irradiation at a wavelength of 366 nm, UV-sensitive $^{CNV}$K nucleotides can form a covalent bond with thymine bases diagonally opposite on the other strand in the cohesion between a complementary pair of sticky ends from two adjacent tiles. Two conventional sticky end pairs on both sides of each tile are added to strengthen the binding between the two tiles and to improve the photo-crosslinking yield.

Formation of Individual DNA Origami Tiles.

The mixture of staple strands, sticky-ended strands and M13mp18 DNA genome was diluted using 1×TAE/Mg$^{2+}$ buffer (40 mM Tris-HCl, pH 8.0, 20 mM acetic acid, 2.5 mM EDTA and 12.5 mM magnesium acetate). The final concentration of M13mp18 DNA genome in the solution was 10 nM, and the molar ratio of the M13mp18 DNA genome to each staple strand was 1:10. The sample was cooled from 90° C. to 16° C. on a thermocycling machine over ~2 hrs. The origami tiles were purified using Amicon Ultra 0.5 mL centrifugal filters (100K, Millipore). At the same time, the buffer was exchanged to become 1×TAE/Mg$^{2+}$ buffer (28 mM magnesium acetate).

Formation of Self-Replication Seeds.

Individual DNA origami tiles (two for dimer seed, four for tetramer seed) were mixed stoichiometrically. The solution was slowly annealed from 61° C. to 24° C. with a ramp of 0.7° C./h, and then cooled further to 4° C. with a ramp of 3° C./h in an incubator.

Self-Replication Cycling.

(1) First-generation tiles and second-generation tiles were prepared by the method above. (2) Seeds, first-generation tiles, and second-generation tiles, with specific concentration ratio (for example, seed:first-generation tile:second-generation tile=1:32:30 in dimer system), were mixed well. (3) The mixture was annealed at 50° C. for 20 min, cooled from 50° C. to 24° C. at a rate of 1.0° C./h and from 24° C. to 4° C. at a rate of 3.0° C./h using an incubator. (4) The solution was exposed to 360 nm ultraviolet lamp (UVP, Model XX-15L, 15 W) at ~10° C. for ~2-3 hrs. (5) 2 μL of the solution was taken out of (4) for AFM imaging. The remaining solution underwent steps (3) to (5) for further self-replication cycles.

Amplification of DNA Origami Dimer by a Serial Transfer Experiment.

After 4 cycles of replication (when half of the monomers were consumed and a leveling off began), 8% of the material from the reaction mixture was transferred to the next replication tube, which contained a fresh supply of later-generation monomers, with an initial ratio of dimer, first-generation and second-generation tiles to be around 1:32:30 after each transfer.

Self-Replication Selection Cycling.

(1) Two seeds (HH and II) and their first- and second-generation tiles (H and I) were prepared by the same method of formation as self-replication seeds. (2) All the tiles with specific ratio (seed:first-generation:second generation=1:8:6) were mixed well. (3) The mixture was annealed at 50° C. for 20 min, cooled from 50° C. to 24° C. at a rate of 1.0° C./h and from 24° C. to 4° C. at a rate of 3.0° C./h using an incubator. (4) The solution was first exposed to the laser diode with the wavelength of 685 nm (Thorlabs HL6750MG, 50 mW, for dominance of II) or 785 nm (Thorlabs L785P090, 90 mW, for dominance of HH) at 4° C. for 20 min. The control sample without laser exposure skipped this step. The solution was exposed to the laser diode and ultraviolet lamp at 4° C. for ~50 min. (5) A 2 µL of the solution was taken out of (4) for AFM imaging. The rest of the solution underwent the steps from (3) to (5) for further self-replication cycles. (6) After each two cycles, the first- and second-generation tiles of the dominate products were added into the solution to keep the initial ratio (dominant dimer:corresponding first-generation tiles:corresponding second-generation tiles=1:7:7). The first- and second-generation tiles of the other species were also added to keep the equal amount of both species (H and I).

AFM Imaging.

Most of the AFM imaging was performed in tapping-mode in buffer, except for the imaging of double-layer complexes of the seed and the first generation. (1) Tapping-mode in Buffer: A 3-5 µL of diluted DNA sample (preheated at 46° C. for 1 h) was spotted on freshly cleaved mica (Ted pella, Inc.) and was left for 1 min to be absorbed. A 30 µL 1×TAE/Mg$^{2+}$ buffer (28 mM magnesium acetate) was added to both the mica surface and the liquid cell. (2) Tapping-mode in air: A 5-7 µL of diluted DNA sample was spotted on freshly cleaved mica (Ted pella, Inc.) at 4° C. and was left for 3 min to be absorbed. The mica was washed with 3 drops of ddH$_2$O three times, and excess water was removed by blotting the mica with a filter paper. The mica was then blown dry using compressed air. All AFM imaging was performed on a NanoScope IV MultiMode SPM (Digital Instruments) with silicon tips (Veeco, Inc.).

Results

Figure 1B:
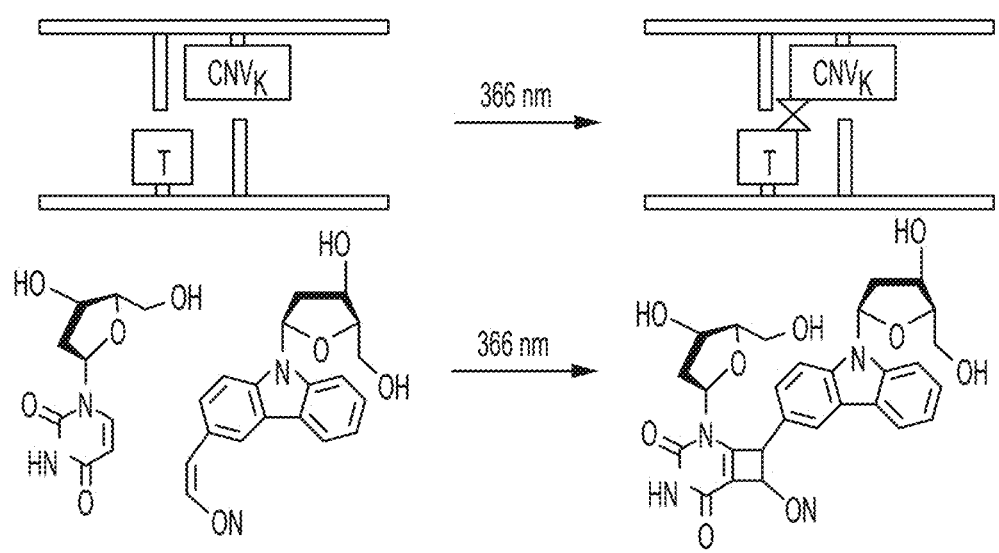

The present inventors have centered their efforts on a general process that autonomously replicates seeds fabricated from individual units into copies with the same shape and information that will continue to replicate for numerous further generations. The goal here is to make devices and materials that can grow exponentially and evolve to have specific desired properties in response to selective pressures. The basic idea of the present process is (i) to have each unit in the seed bind specifically to a complementary unit from a bath with a temperature dependent bond at low temperature, (ii) to covalently link the assembled daughter units using UV-photoactivated bonding and then (iii) separate seeds from daughters by heating. Both seeds and daughters serve as templates for the further progeny, doubling the population with each generation. A realization of such a system is shown in FIG. 1A, there are two complementary tiles made from rectangular DNA origami constructs (Rothemund, 2006). On one side the tiles are decorated by DNA hairpins that form a "T" or an "A" to be read by atomic force microscopy (AFM). On the flip sides are eight "vertical" sticky ends (red strands) that are complementary, T tiles to A tiles, and pair these tiles in the vertical direction. They encode the information for recognition and guarantee information transfer from a seed to later generations. The sticky ends are supported vertically by hybridizing their lower nine nucleotides with eight strands to form double helices. A second set of sticky ends (drawn in dotted and dashed lines) is attached to both ends of the origami tiles horizontally, in the direction of the origami tile's DNA double helices. These can bind to other tiles to form patterns of the origami tiles, TT, TA, ATA. etc. There are six horizontal sticky ends on each side of each tile, of which four contain the photo-cross-linkable nucleotide (FIG. 1B) 3-cyanovinylcarbazole nucleoside ($^{CNV}K$) (Yoshimura et al., 2008). All hairpins, sticky ends and supports are extensions of the staple strands that hold the origami together.

Figure 1C:
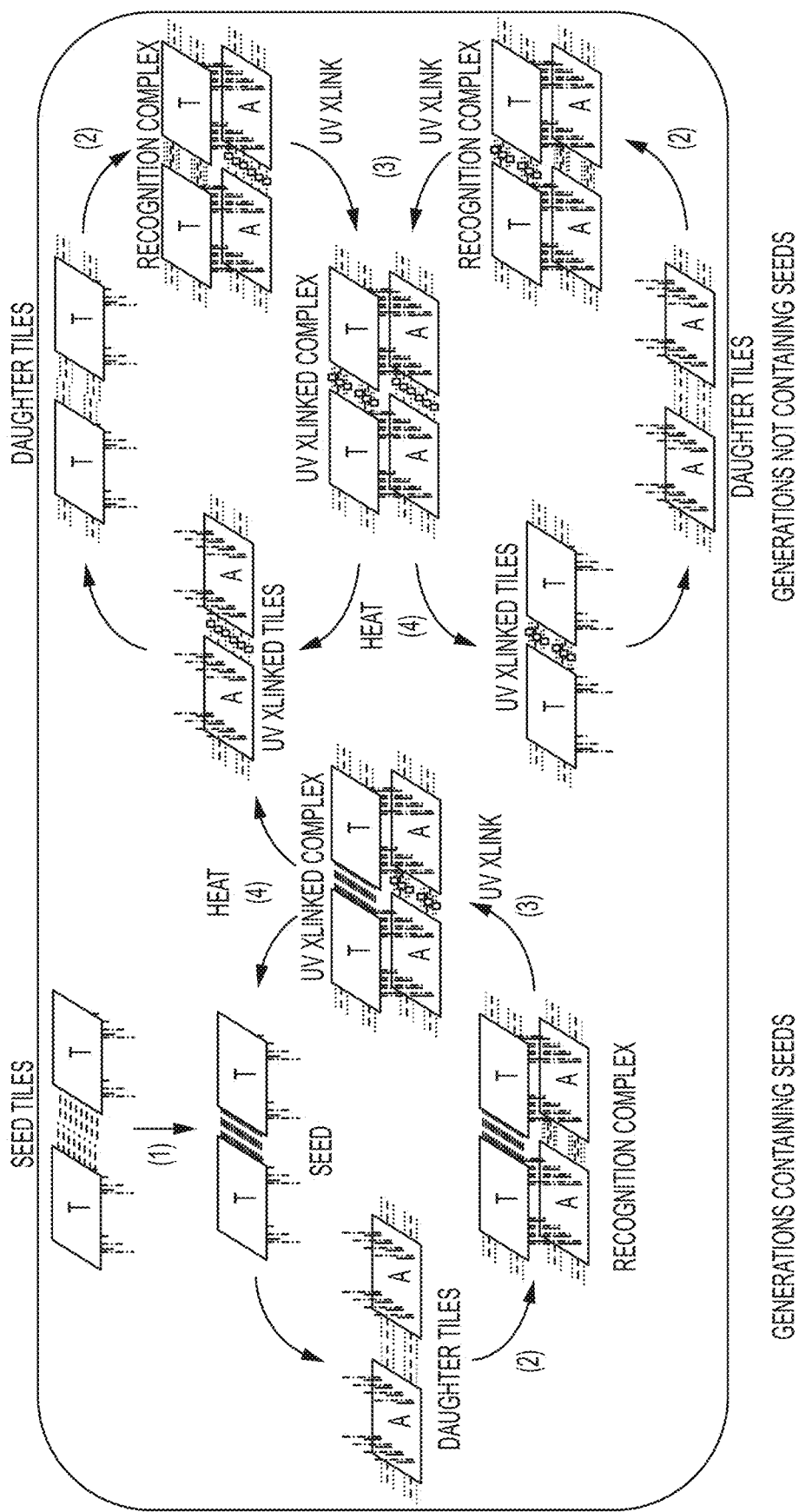
Figure 2A:
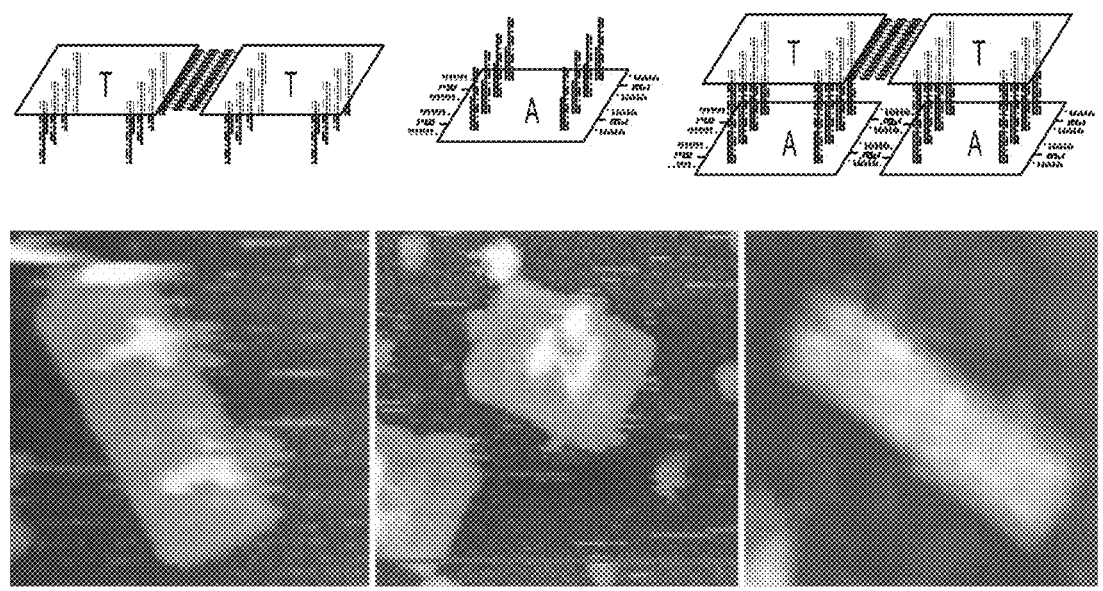
FIGS. 2A-2C show self-replication of DNA seeds.

FIG. 1C shows a schematic of self-replication cycling for the DNA origami pattern, using a dimer DNA seed. To begin, the seed 'TT' is constructed from two T-tiles using sticky-end cohesion. The T-tiles of the seed have different groups of horizontal sticky ends with high melting temperature, no $^{CNV}K$ and no external bonds. An AFM image of the seed is shown in FIG. 2A, demonstrating that the dimer seed forms as designed with high yield (see FIG. 10A for zoomed-out images). Seeds as initiators are added to a pool of A-tile and T-tile monomers. First-generation tiles (A-tiles, AFM image shown in FIG. 2A, zoom-out images shown in FIG. 13B) and seeds with complementary vertical cohesive sequences are paired together to form double-layer origami dimers (FIG. 2A and FIGS. 10C-10D), analogous to the DNA base pairing of adenine and thymine (5'-ApA-3' with 5'-TpT-3'). Two free monomer tiles in solution cannot bind to each other, in the temperature range of 4° C.—50° C., during the replication cycle, owing to the low melting temperature of the horizontal sticky ends. When immobilized on the seed by vertical binding, adjacent DNA origami tiles are present at a greatly enhanced local concentration, leading to the formation of six sticky end pairs $^{CNV}K$ will between adjacent DNA tiles. Upon 366-nm UV irradiation, sticky ends containing bond covalently to the thymine base diagonally opposite in the complementary strand. The same DNA sequences of horizontal sticky ends are used in the A-tile or the T-tile, except for the seed, to ensure successful replication.

To quantify the amplification, N, of dimers, each generation was sampled using AFM images to measure the percentage of dimers, $P_n$, compared to the initial percentage of seeds, $P_0$, with $N=P_n/P_0$ (see Table 6 below).

TABLE 6

Statistics for replication of dimer DNA origami tile calculated from AFM images

| | Seed (TT):First-generation tile (A):Second-generation tile (T) | | | | | |
|---|---|---|---|---|---|---|
| | 1:16:14 | | 1:32:30 | | 1:1024:1022 | |
| Cycle N | Monomer | Dimer | Monomer | Dimer | Monomer | Dimer |
| 1 | 1346 | 100 | 707 | 24 | | |
| 2 | 1000 | 154 | 899 | 62 | 1414 | 3 |
| 3 | 977 | 404 | 732 | 109 | 1036 | 5 |
| 4 | 647 | 373 | 504 | 212 | 1020 | 10 |
| 5 | 635 | 467 | 542 | 372 | 1177 | 21 |
| 6 | 437 | 439 | 466 | 401 | 983 | 34 |
| 7 | | | 449 | 559 | 1812 | 142 |
| 8 | | | 346 | 567 | 2760 | 391 |
| 9 | | | | | 1524 | 554 |
| 10 | | | | | 1340 | 701 |
| 11 | | | | | 995 | 667 |
| 12 | | | | | 984 | 766 |
| 13 | | | | | 698 | 746 |
| 14 | | | | | 531 | 918 |

Figure 2B:
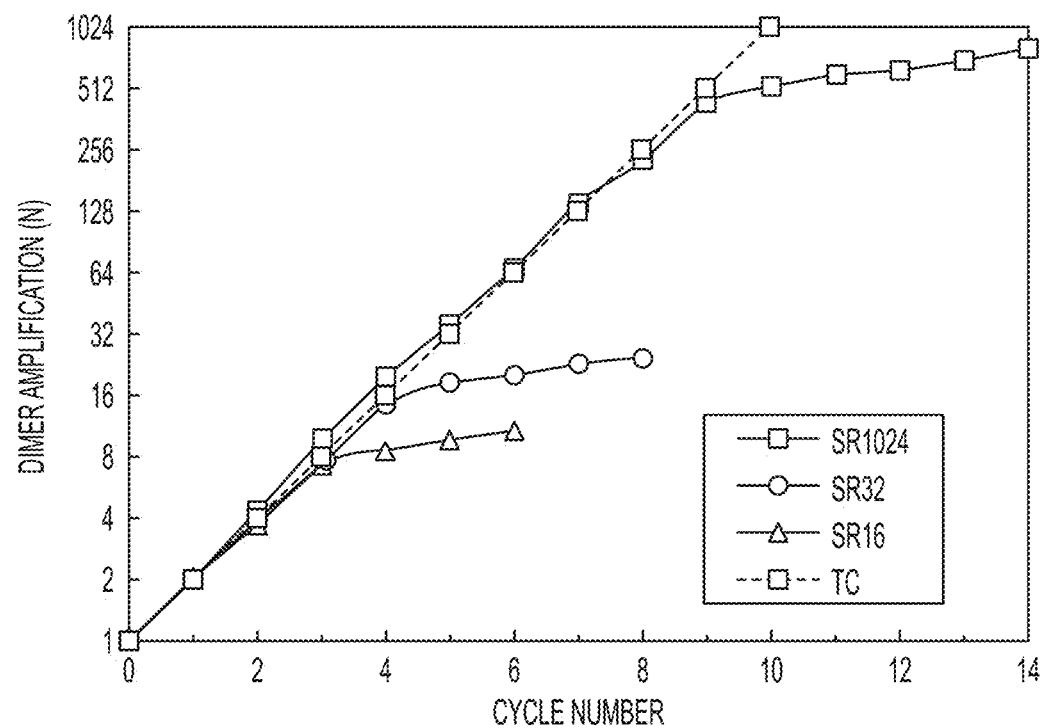
Figure 2C:
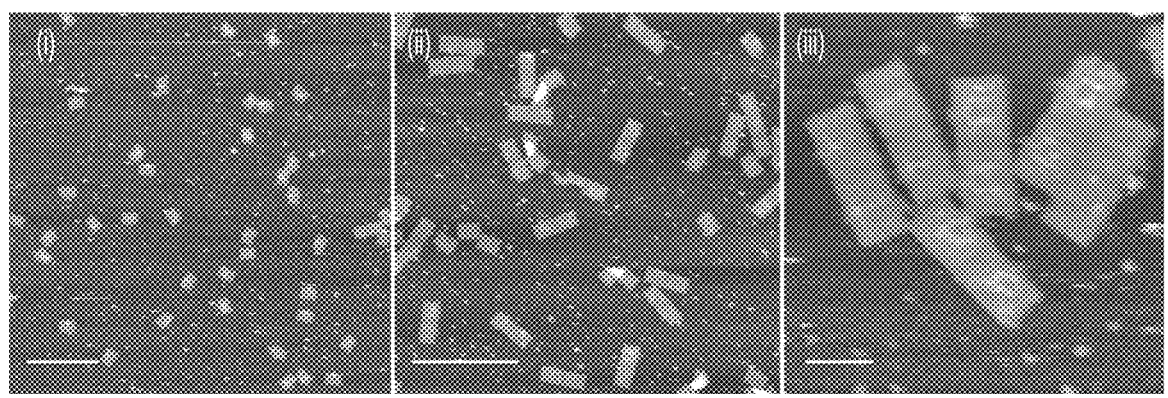
Figure 11:
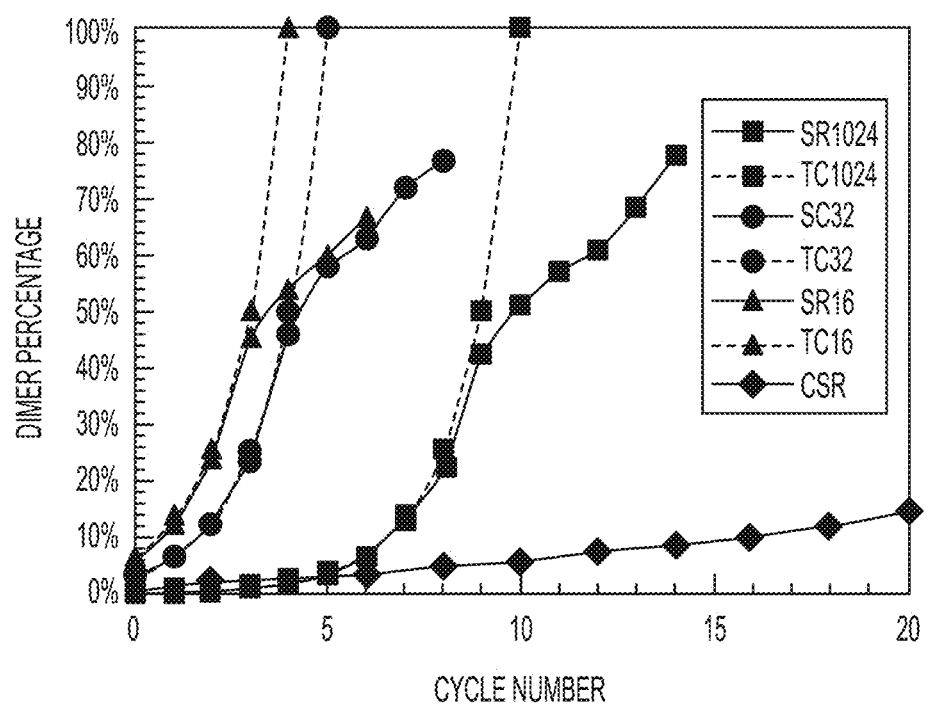
FIG. 11 shows DNA origami dimer percentage (yield) during replication cycling. Dimer percentage is calculated from the equation PD=ND/(ND+NM/2), where PD is dimer percentage, and ND and NM are the amounts of dimers and monomers, respectively (shown in Table 6). Solid curves with triangles, circles and squares represent the result obtained with various initial ratios of seeds, A-tiles and T-tiles (triangles: 1:16:14, circles: 1:32:30 and squares: 1:1024:1022). The theoretical curves of exponential growth are shown as dashed lines. The replication of dimers (including seeds and later-generations) increased exponentially before leveling off as the supply of substrates became exhausted. The system without seeds is presented as a control, drawn as a solid curve with diamonds, which affirms that seeds triggered the exponential self-replication.
Figure 12:
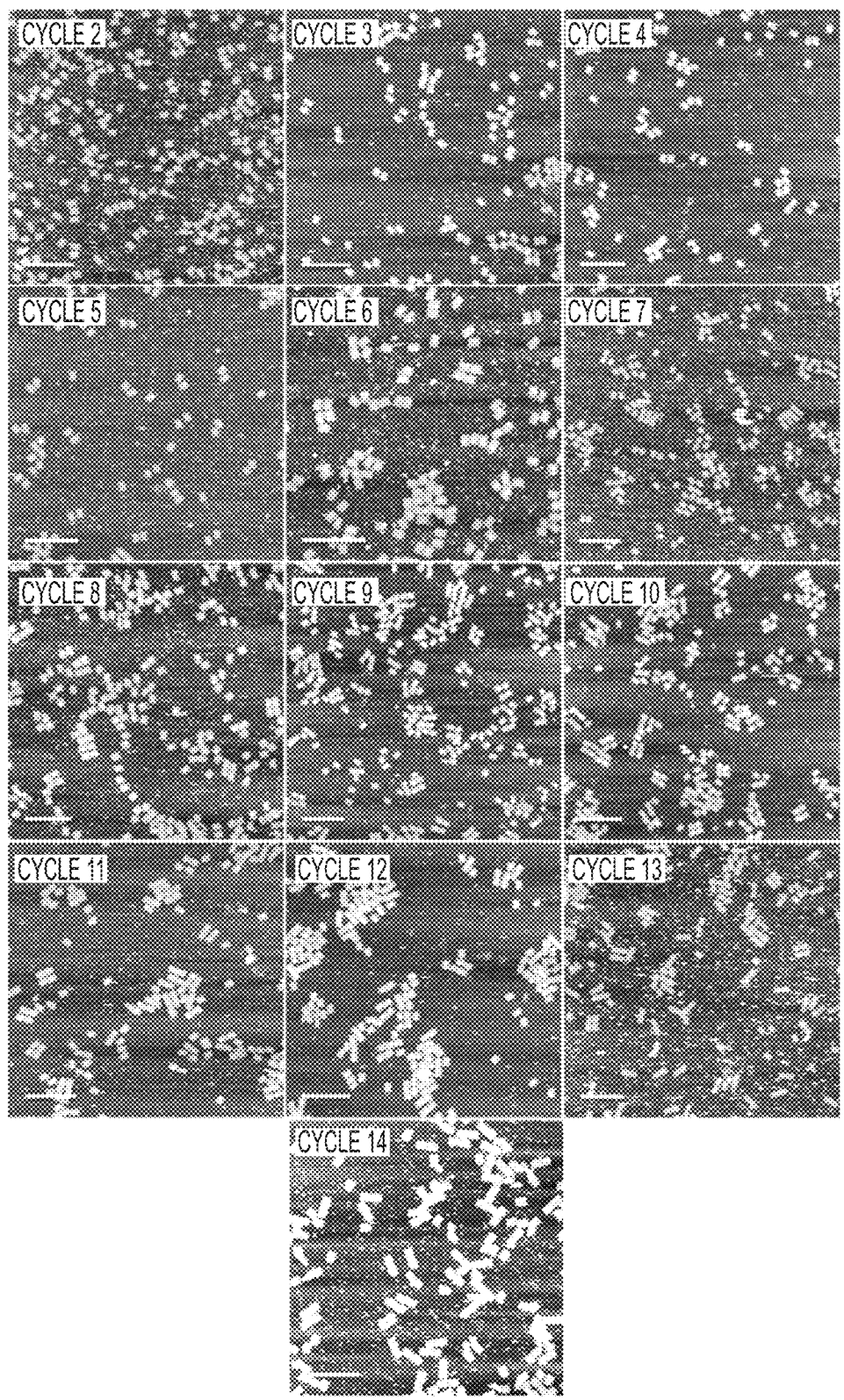
FIG. 12 shows AFM images of dimer replication cycling (ratio of seeds, A-tiles and T-tiles is 1:1024:1022). The statistics for amplification is calculated from several AFM images in each cycle. The scale bars are 500 nm.

FIG. 2C(i) shows an AFM image of the initial state of the pool containing dimer TT-seeds, A-tiles and T-tiles in a ratio of 1:32:30. After 8 cycles of self-replication, the dimers become dominant products in the pool by consuming monomers of A-tiles and T-tiles to produce further-generation AA and TT dimers (FIG. 2C(ii)). FIG. 2B shows the exponential amplification from analysis of more than 700 tiles in each cycle of self-replication (generation). For an initial ratio of TT-seed:A-tile:T–tile=1:1024:1022 (solid curve with squares; AFM images of cycles 2-14 are shown in FIG. 12), the exponential amplification is more than a 480-fold amplification after 9 cycles (amplification of 1.986/cycle). All amplification curves level off when about half of the monomers are consumed. The yield of the replicated generations with precisely encoded information TT or AA is estimated to be more than 99% (more than 100 dimers sampled in zoomed-in AFM images; no AT or TA dimers were found). However, as the cycle number increases, some trimer tiles are found with an extremely low yield (<1%). To demonstrate that seeds trigger self-replication, a control has been performed in which the solution contains only monomers of A-tiles and T-tiles; fewer than 14% dimers are detected after 20 replication cycles (FIG. 11).

Figure 3A:
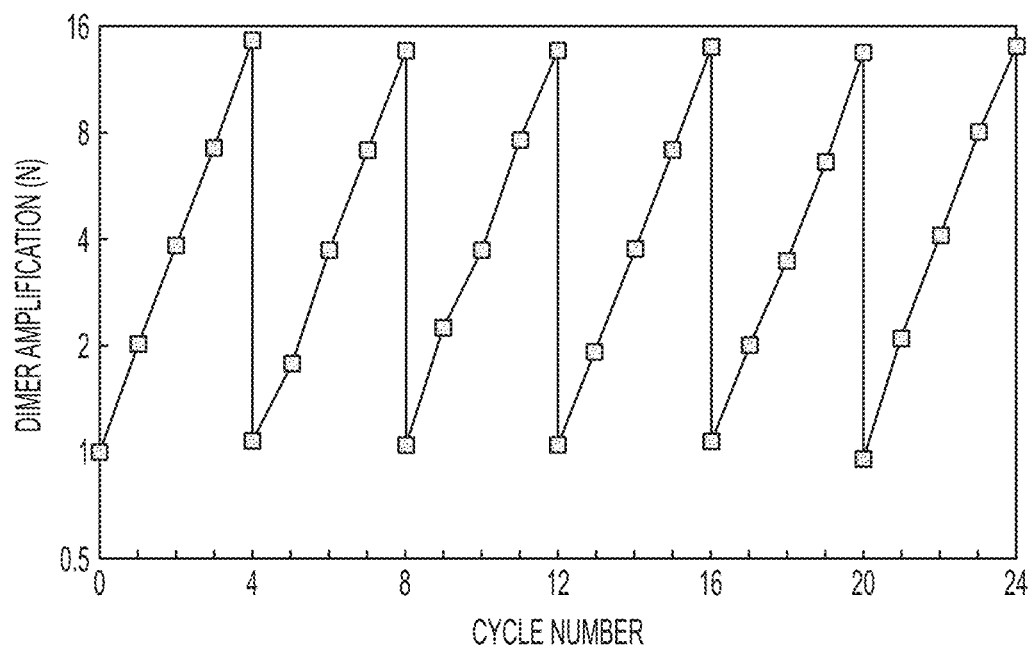
FIGS. 3A-3C show amplification of a serial transfer experiment.

Exponential growth was allowed to proceed indefinitely in a serial transfer experiment wherein a portion of a half-reacted mixture is transferred to a new pool that contains fresh later-generation monomers of A-tiles and T-tiles. The system with a ratio of 1:32:30 was used. Six successive replications were carried out in this manner, each 4 cycles in duration (when half of the monomers were consumed and a leveling off began; FIG. 3A) and then 8% of the material was transferred from one reaction solution to the next. The initial solution contained TT seeds, but all subsequent replication pools contained only those dimers TT or AA that were transferred over. The initial concentration ratio of dimers, A-tiles and T-tiles was maintained around 1:32:30 after each transfer. FIG. 3C shows the products of a randomly chosen replication unit of 4 cycles in duration, cycles 17-20, which verify that the percentage of dimers grows as the cycle number increases. Exponential growth was maintained throughout 24 cycles, with an overall amplification (1.93/cycle) of greater than 7,000,000-fold for dimers TT and AA as shown in FIG. 3 (see Table 7 below for statistics of amplification of dimers through a serial transfer experiment).

TABLE 7

Statistics for amplification of dimer by a serial transfer experiment

| Cycle N | M | D | Dimer Percentage | Amplification |
|---|---|---|---|---|
| 0 |  |  | 0.03125 | 1 |
| 1 | 707 | 24 | 0.0635 | 2.03 |
| 2 | 899 | 62 | 0.121 | 3.87 |
| 3 | 732 | 109 | 0.230 | 7.36 |
| 4 | 504 | 212 | 0.457 | 14.6 |
| 4 (T1) | 1698 | 30 | 0.0341 | 1.09 |
| 5 | 1199 | 39 | 0.0611 | 1.79 |
| 6 | 1286 | 94 | 0.128 | 3.75 |
| 7 | 1409 | 228 | 0.245 | 7.19 |
| 8 | 1144 | 507 | 0.470 | 13.8 |
| 8 (T2) | 1588 | 27 | 0.0329 | 1.05 |
| 9 | 1536 | 61 | 0.0736 | 2.24 |
| 10 | 2081 | 147 | 0.124 | 3.77 |
| 11 | 2249 | 385 | 0.255 | 7.76 |
| 12 | 939 | 391 | 0.454 | 13.8 |
| 12 (T3) | 2227 | 38 | 0.0330 | 1.06 |
| 13 | 1016 | 35 | 0.0645 | 1.95 |
| 14 | 1454 | 104 | 0.125 | 3.79 |
| 15 | 1680 | 265 | 0.240 | 7.27 |
| 16 | 617 | 268 | 0.465 | 14.1 |
| 16 (T4) | 2290 | 40 | 0.0338 | 1.08 |
| 17 | 2441 | 89 | 0.0680 | 2.01 |
| 18 | 1056 | 71 | 0.118 | 3.51 |
| 19 | 1039 | 150 | 0.224 | 6.64 |
| 20 | 970 | 408 | 0.457 | 13.5 |
| 20 (T5) | 1686 | 26 | 0.0299 | 0.957 |
| 21 | 2424 | 82 | 0.0634 | 2.12 |
| 22 | 2015 | 143 | 0.124 | 4.15 |
| 23 | 1326 | 213 | 0.243 | 8.13 |
| 24 | 875 | 318 | 0.421 | 14.1 |

Figure 3B:
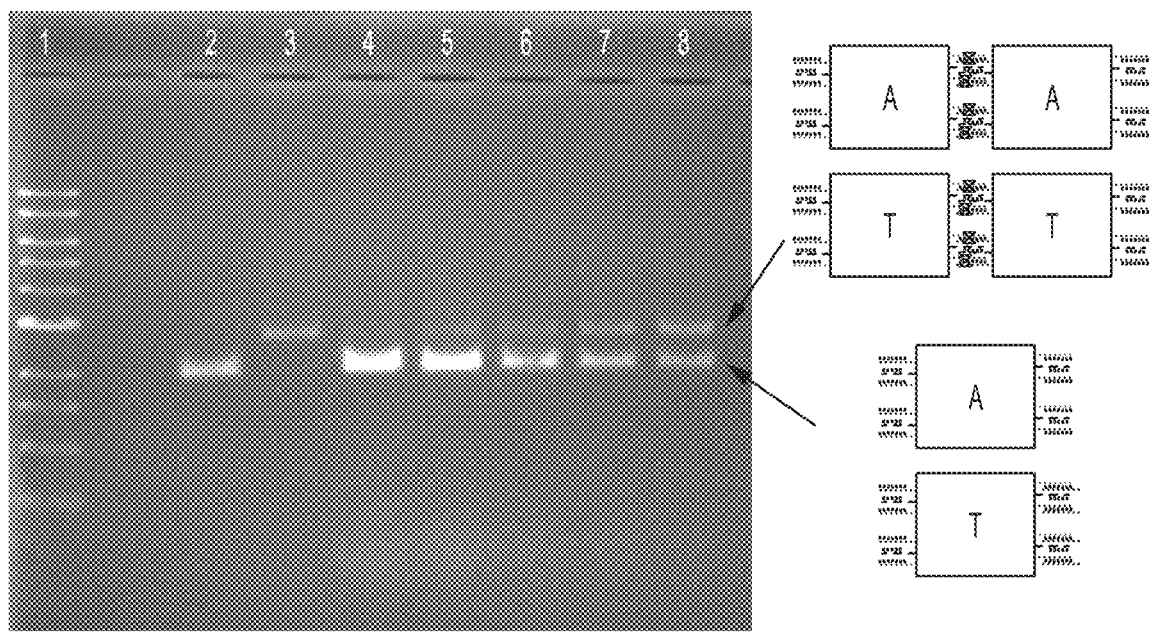
Figure 3C:
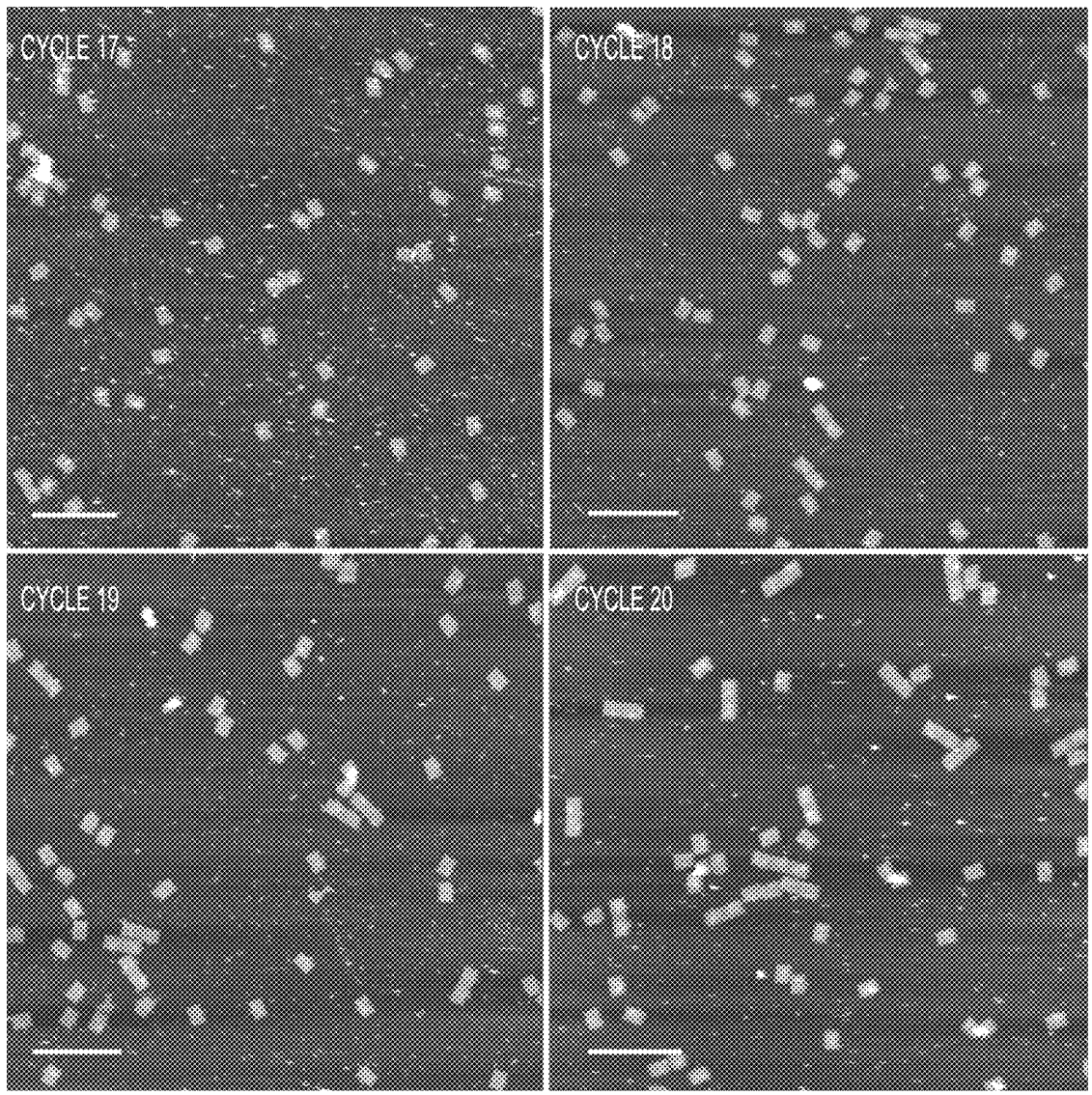

Nondenaturing agarose gel electrophoresis was also applied to examine the self-replication products from cycle 8 to cycle 12 (FIG. 3B). The intensity of the upper bands, representing dimers, increases exponentially from cycle 8 to cycle 12 (lane 4 to lane 8); while, the intensity of the lower bands, monomers, decreases. The plot of the dimer amplification versus cycle quantified from the gel is consistent with the plot obtained from AFM images.

Figure 4A:
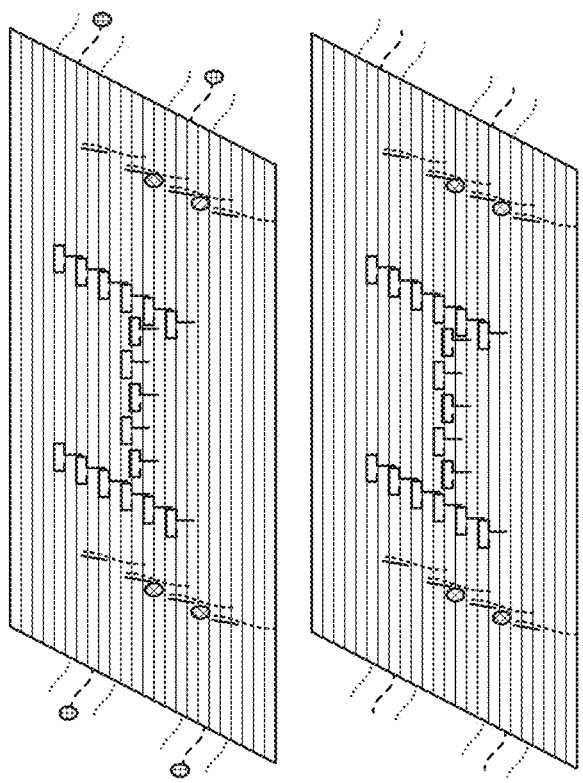
FIGS. 4A-4G show self-replication enabling selection.
Figure 4A:
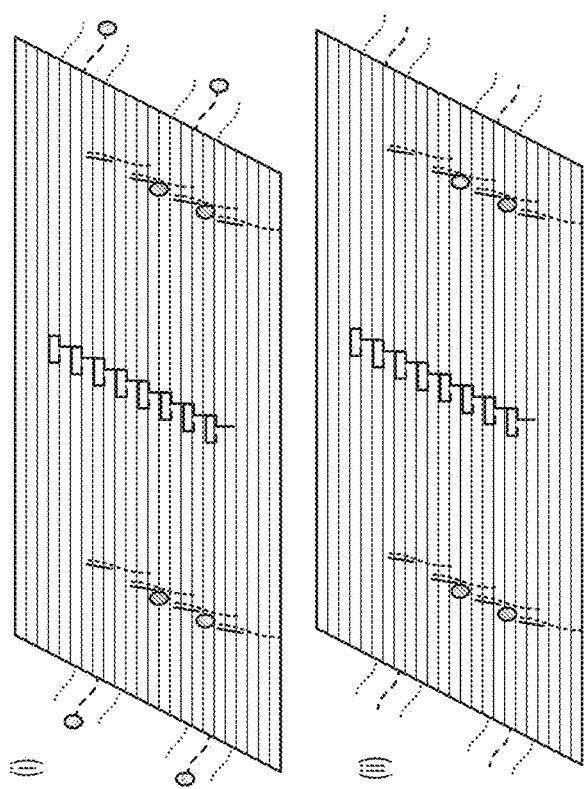
Figure 4B:
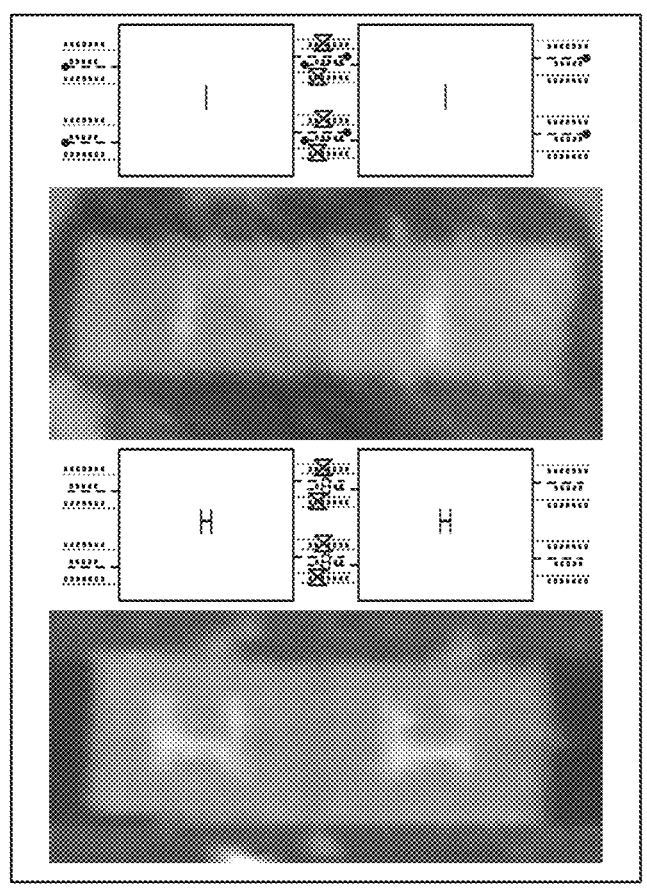

A selection experiment was performed to demonstrate that the present DNA origami system is capable of evolution. DNA origami dimers were subjected to an environment change that affected their ability to replicate. Here, DNA origami dimers labeled with 'HH' and 'II' were used as competing species. In contrast to the complementary system used above, dimer HH can only replicate HH, and II replicates II. Near-infrared dyes that have light-activated heat generation properties were used to generate the environmental change. IR Dye 700 (hatched circles in FIG. 4A) and IR Dye 800 (dotted circles in FIG. 4A), have been chosen and attached to two origami tiles HH and II (FIG. 4B), respectively (see Table 8 below for formation of dimers HH and II).

TABLE 8

Sequences of IR dye-modified strands for self-replication selection

| First-generation tile 'H' | IR700-9A-092 | aAAAAAAAATGATAAATAACGCTCAACAGTAGGACCGCACT | SEQ ID NO: 320 |
|---|---|---|---|
|  | IR700-9A-127 | aAAAAAAAAAAATATTCCCCAGCTACAATTTTAGAATTAAC | SEQ ID NO: 321 |
|  | IR700-9A-098 | aAAAAAAAAAAGGTGGCACGAGTAGATTTAGTTTCAACATG | SEQ ID NO: 322 |
|  | IR700-9A-133 | aAAAAAAAAATTCAACTGAAGAAAAATCTACGTAACCGGAT | SEQ ID NO: 323 |
|  | IR700-063 | tAGGTTTTACAGGAAGATTGTATACAGAAAAGCCCCAAAATTTT | SEQ ID NO: 324 |
|  | IR700-064 | aCCTATTTAATTATTTGCACGTAAGAACCTACCATATCAATTTT | SEQ ID NO: 325 |
|  | IR700-152 | aGTCTTTTGGCTGACCTTCATCAAACCAGGCGCATAGGCTTTT | SEQ ID NO: 326 |

TABLE 8-continued

Sequences of IR dye-modified strands for self-replication selection

| | | | |
|---|---|---|---|
| | IR700-153 | aGACTTTTCACAAGAATTGAGTTAT ATCAGAGAGATAACCTTTT | SEQ ID NO: 327 |
| Seed or second-generation tile 'H' | IR700-9A-092 | aAAAAAAAATGATAAATAACGCTCA ACAGTAGGACCGCACT | SEQ ID NO: 328 |
| | IR700-9A-127 | aAAAAAAAAAAATATTCCCCAGCTA CAATTTTAGAATTAAC | SEQ ID NO: 329 |
| | IR700-9A-098 | aAAAAAAAAAAGGTGGCACGAGTA GATTTAGTTTCAACATG | SEQ ID NO: 330 |
| | IR700-9A-133 | aAAAAAAAAATTCAACTGAAGAAA AATCTACGTAACCGGAT | SEQ ID NO: 331 |
| First-generation tile 'I' | IR800-9A-092 | aAAAAAAAATGATAAATAACGCTCA ACAGTAGGACCGCACT | SEQ ID NO: 332 |
| | IR800-9A-127 | aAAAAAAAAAAATATTCCCCAGCTA CAATTTTAGAATTAAC | SEQ ID NO: 333 |
| | IR800-9A-098 | aAAAAAAAAAAGGTGGCACGAGTA GATTTAGTTTCAACATG | SEQ ID NO: 334 |
| | IR800-9A-133 | aAAAAAAAAATTCAACTGAAGAAA AATCTACGTAACCGGAT | SEQ ID NO: 335 |
| | IR800-063 | tAGGTTTTACAGGAAGATTGTATAC AGAAAAGCCCCAAAATTTT | SEQ ID NO: 336 |
| | IR800-064 | aCCTATTTAATTATTTGCACGTAAGA ACCTACCATATCAATTTT | SEQ ID NO: 337 |
| | IR800-152 | aGTCTTTTGGCTGACCTTCATCAAAC CAGGCGCATAGGCTTTTT | SEQ ID NO: 338 |
| | IR800-153 | aGACTTTTCACAAGAATTGAGTTAT ATCAGAGAGATAACCTTTT | SEQ ID NO: 339 |
| Seed or second-generation tile 'I' | IR800-9A-092 | aAAAAAAAATGATAAATAACGCTCA ACAGTAGGACCGCACT | SEQ ID NO: 340 |
| | IR800-9A-127 | aAAAAAAAAAAATATTCCCCAGCTA CAATTTTAGAATTAAC | SEQ ID NO: 341 |
| | IR800-9A-098 | aAAAAAAAAAAGGTGGCACGAGTA GATTTAGTTTCAACATG | SEQ ID NO: 342 |
| | IR800-9A-133 | aAAAAAAAAATTCAACTGAAGAAA AATCTACGTAACCGGAT | SEQ ID NO: 343 |

Figure 4C:
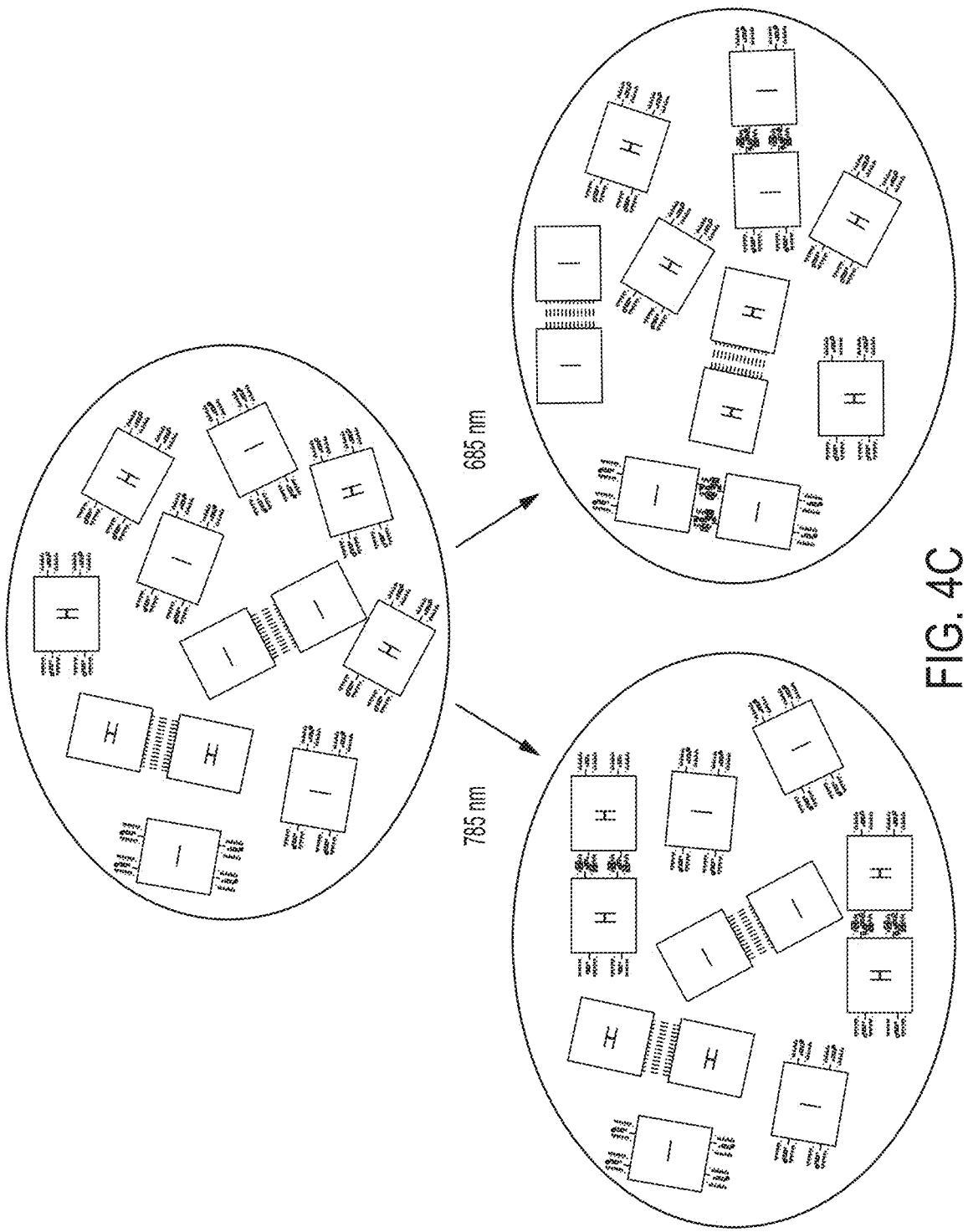
Figure 4D:
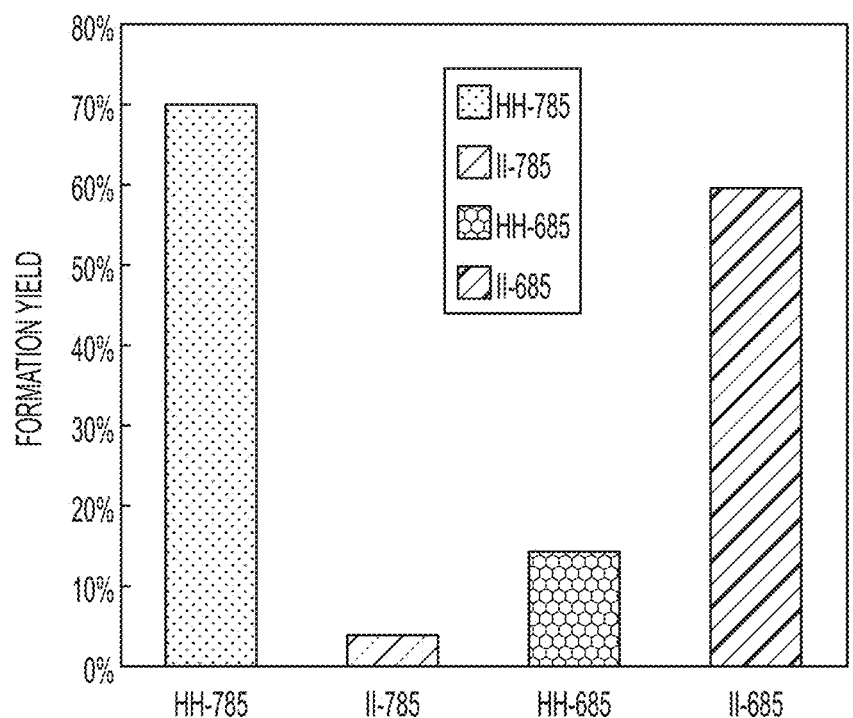
Figure 13:
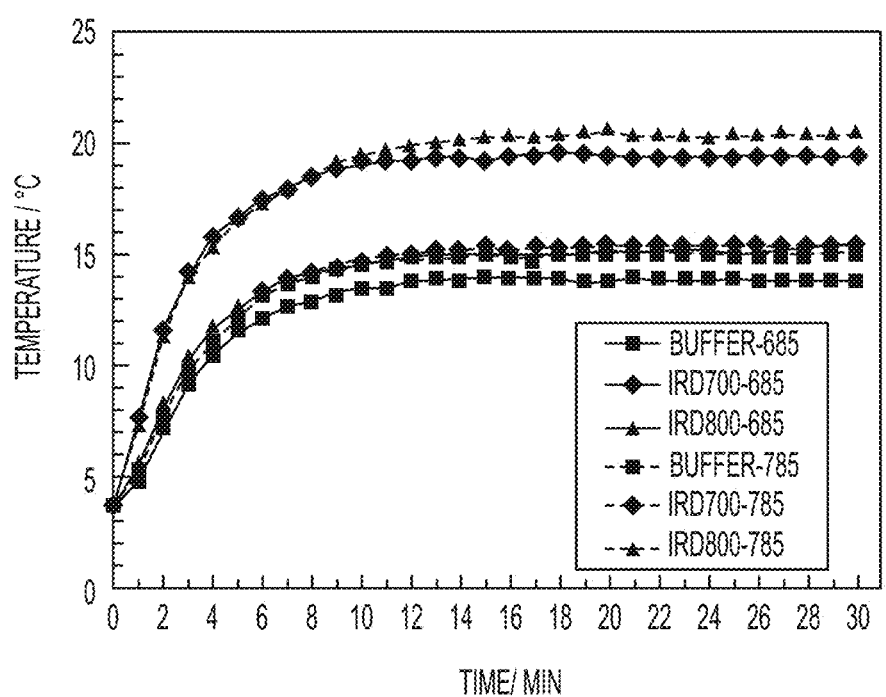
FIG. 13 is a graph showing the heat generation profile of tubes containing buffer or IR dye-modified oligonucleotides when irradiated with IR lasers for 30 minutes. Solid curves were measured under 685-nm laser exposure, while dashed curves were obtained with 785-nm laser. The concentrations of the oligonucleotides (19 µM) are controlled to be the same as the local concentration of the dyes in double-layer origami dimers. The lasers and the samples, when operating, were enclosed in a box to prevent external emission of the NIR light and to avoid air circulation that would affect the temperature of the samples. The starting temperature was ~3.8° C. The temperature of the solution was measured with a thermocouple for the 30-minute laser exposure. The solution containing oligonucleotides modified by IR Dye 700 produced a significantly higher peak temperature increase of ~4° C. than those under 685-nm laser irradiation. The IR Dye 800-modified oligonucleotide solution generated the highest peak temperature increase.
Figure 14A:
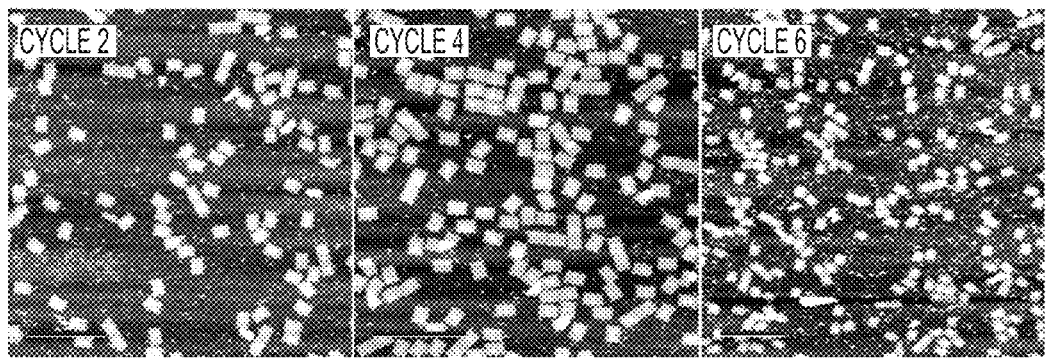
FIGS. 14A-14D show AFM images of replication selection cycling.
Figure 14B:
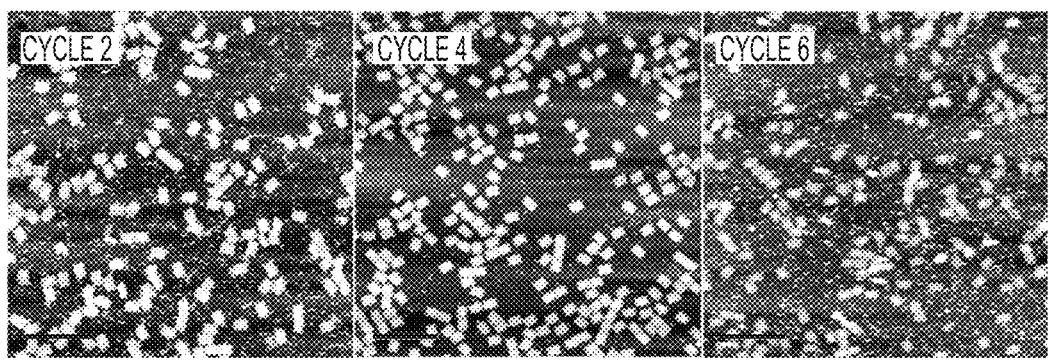
Figure 14C:
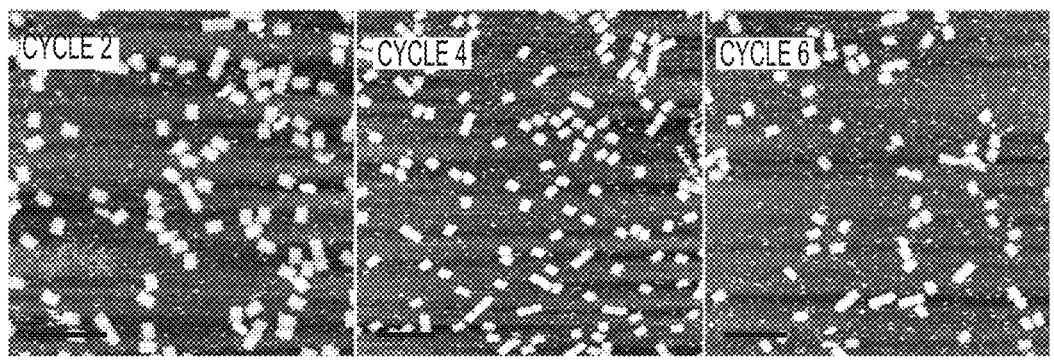
Figure 14D:
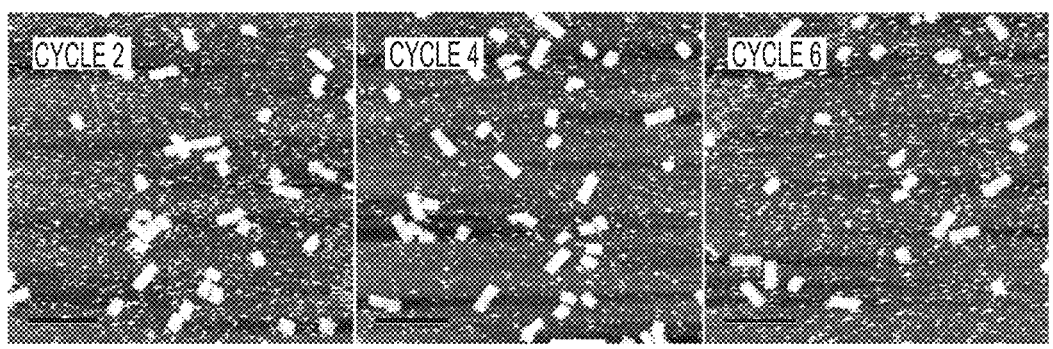

The heat generation profiles of the oligonucleotides modified with IR Dye 700 or IR Dye 800 at their 5' ends were measured during 30 minutes of laser irradiation. The concentrations of the oligonucleotides modified with dyes are controlled to be similar to the local concentration of the dyes in double-layer origami dimers. IR Dye 700- and IR Dye 800-modified oligonucleotides produced a temperature increase of about 5° C. under 685-nm laser and 785-nm laser irradiation, respectively (FIG. 13). The effect of light/heat on the formation of first-generation dimers from a template: monomer ratio of 1:2 is shown in FIG. 4D. Formation of species HH was barely affected by 785-nm laser diode, but 685-nm laser irradiation caused a significant reduction in yield (see Table 9 below for statistics).

TABLE 9

Statistics for formation yields of daughter generations under 685-nm or 785-nm laser irradiation.

| | Monomer | Dimer | Dimer Formation Yield |
|---|---|---|---|
| HH-785 | 108 | 181 | 0.702 |
| HH-685 | 475 | 277 | 0.0387 |
| II-785 | 323 | 168 | 0.143 |
| II-685 | 257 | 319 | 0.597 |

Figure 4E:
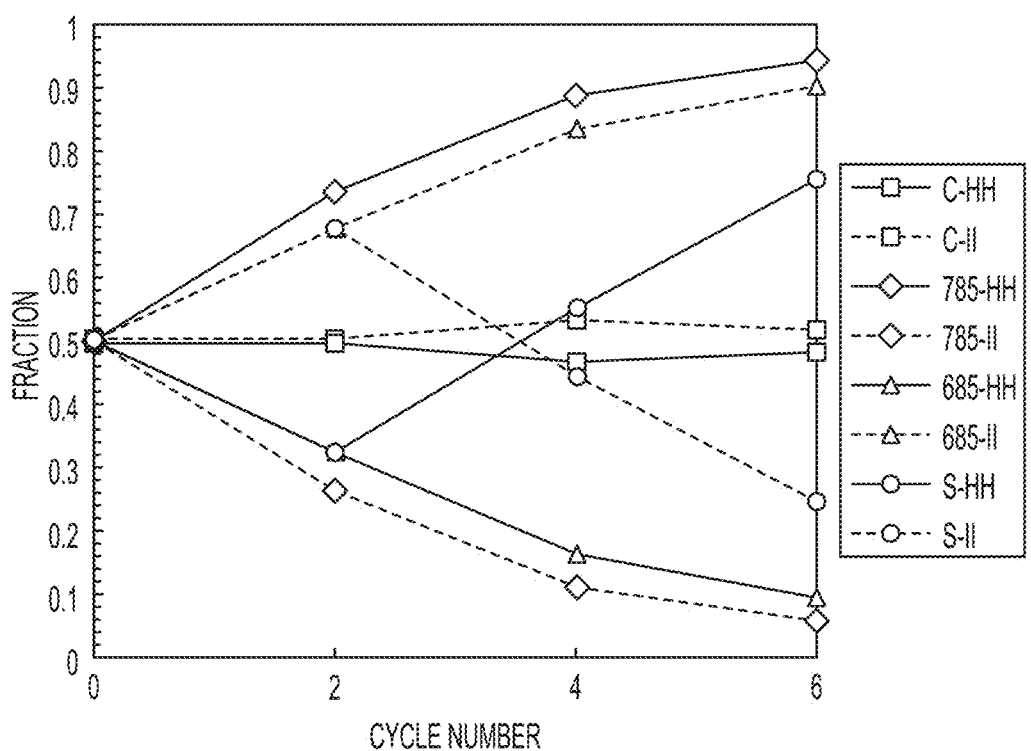

The opposite results were obtained in the formation of species II. The two IR dyes indeed produce a replication selection where an environmental change results from laser color change. In the selection system, the initial concentrations of seeds HH and II were the same and the ratio of seeds:monomers=1:16 for both I-tiles and H-tiles. After vertical recognition and cooling, successive generations of NIR dye modified tiles were exposed to laser irradiation for 20 minutes before UV exposure. The IR dyes absorbed energy and locally heated the tiles of the corresponding wavelength. The vertical binding efficiency of successive generations and concomitantly the horizontal photo-cross-linking yield of later generations decreases, due to the local temperature increase. The temperature increase decays inversely with distance from absorbing tiles; thus, if the average temperature rise of a tile containing a dye is 10° C., a tile 1 micron away is heated less than 1° C. The replication yield of the absorbing DNA origami dimers was observed to be reduced. As illustrated in FIG. 4C, species II amplifies under 685-nm light, while species HH amplifies under 785-nm light. So as to prevent degradation of heat production, fresh NIR dye-modified monomers were added into the replication mixture after each 2 cycles, thereby keeping a ratio of 1:16 between dimer and monomer. The result of the self-replication selection under different environments is shown in FIG. 4E. The proportion between dimer HH and II was quantified from AFM images using the simple relationships, $D_{II}=1-D_{HH}$, where $D_{HH}$ and $D_{II}$ are the fractions of dimers HH and dimers II, respectively (FIGS. 14A-14D and Table 10 below).

TABLE 10

S Statistics for self-replication selection

| Cycle | Control (Without laser) | | | Selection with 785-nm laser | | | Selection with 685-nm laser | | | Selection with laser switch | | |
|---|---|---|---|---|---|---|---|---|---|---|---|---|
| | Monomer | HH | II | Monomer | HH | II | Monomer | HH | II | Monomer | HH | II |
| 0 | 529 | 19 | 19 | 529 | 19 | 19 | 529 | 19 | 19 | 529 | 19 | 19 |
| 2 | 319 | 51 | 52 | 765 | 95 | 34 | 308 | 20 | 42 | 308 | 20 | 42 |
| 4 | 300 | 51 | 58 | 964 | 129 | 16 | 823 | 23 | 117 | 1526 | 67 | 54 |
| 6 | 316 | 59 | 64 | 2013 | 251 | 15 | 1584 | 19 | 185 | 560 | 49 | 16 |

Figure 4F:
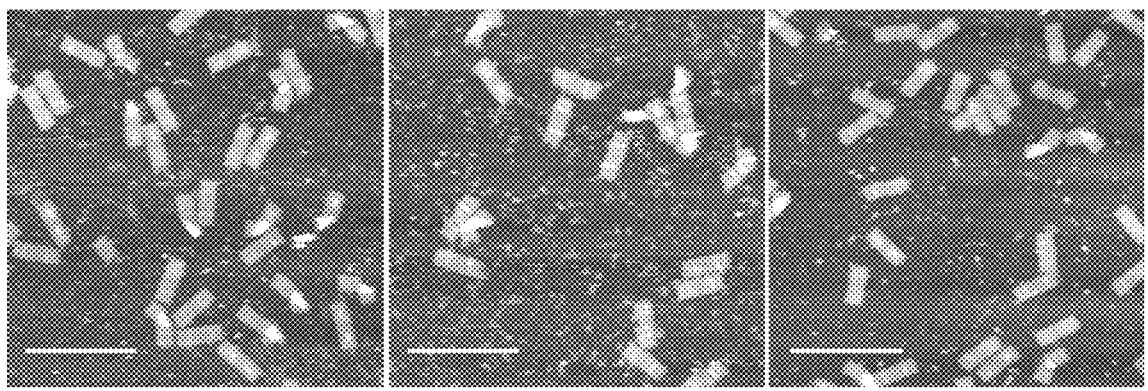
Figure 4G:
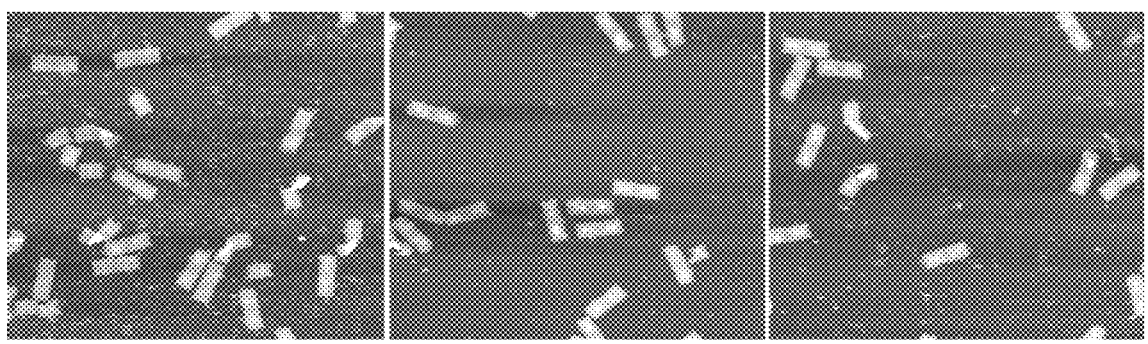

After 6 cycles, species HH became dominant under 785-nm laser irradiation, representing more than 94% of the total dimers (solid diamond curve in FIG. 4E). In contrast, dimer II became the preferred species, ~90%, under 685-nm laser irradiation (dashed triangle curve). When no laser was applied (control system, no environment change, curves with square as datapoints), the ratio of dimer HH and II remained constant around 1:1, confirming that both species underwent replication amplification at similar rates. It was also demonstrated that minor species can become dominant if the environment changes favorably (the laser was changed from 685 nm to 785 nm after two replication cycles). The curves with circles as datapoints in FIG. 4E show that the dimers II with a higher fraction in the first two cycles turned into minor species after the laser was switched to 785 nm; meanwhile, the dimers HH became dominant. After the dimer purification from the replication mixtures, AFM images of cycles 2 and 6 (each 2 self-replication cycles) under 685-nm or 785-nm laser exposure are presented in FIGS. 4F-4G. The results indicate that artificial evolution promoting one component over another has indeed been achieved using the wavelength of light as the selection factor.

The replication/selection system the present inventors have demonstrated depends upon the catalysis of progeny formation by a covalently crosslinked parent. It is related to the purification/selection system used by Adleman when he amplified the correct start and end points of a Hamiltonian path search using PCR (Adleman, 1994). The process demonstrated in this Example should be readily adapted to other systems that need to optimize the properties of materials. A multi-component seed is introduced into a bath of the individual components, it templates the assembly of complementary (or similar) components by specific reversible recognition, which can be chemical or physical (Sacanna et al., 2010); a subsequent step fixes the daughter configuration permanently and the daughter is then separated from the template. The material with the desired properties is distinguished from other members in the pool by enabling it to replicate. Cycling produces exponential growth and environmental changes can affect growth rates, leading to selective evolution. The present demonstration with DNA origami tiles may prove particularly useful since origami tiles can be attached to many nano- and micron-scale components; these components can then be assembled and replicated into devices that are selectively evolved and optimized for different purposes.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Adleman, L. M., Molecular computation of solutions to combinatorial problems, Science 266, 1021-1024 (1994).

Cho, Y. et al., Controlled release of an anti-cancer drug from DNA structured nano-films. Scientific Reports 4:4078 (2014), doi:10.1038/srep04078.

Douglas, S. M., Marblestone A. H., Terrapittayanon, S., Vasquez, A., Church, G. M., Shih, W. M., Rapid prototyping of 3D DNA-origami shapes with caDNAno. Nucl. Acids Res. 37, 5001-5006 (2009).

Eckardt, L. H., Naumann, K., Pankau, W. M., Rein, M., Schweitzer, M., Windhab, N., von Kiedrowski, G., Chemical copying of connectivity, Nature 420, 286-286 (2002).

Ellington, A. D., Szostak, J. W., In Vitro selection of RNA molecules that bind to specific ligands, Nature 346 818-822 (1990).

Lee, D. H., Severin, K., Yokobayashi, Y. & Ghadiri, M. R. Emergence of symbiosis in peptide self-replication through a peptide hypercyclic network. Nature 390, 591-594 (1997).

Leunissen, M. E., Dreyfus, R., Sha, R., Wang, T., Seeman, N. C., Pine, D., Chaikin, P. M., Towards self-replicating materials of DNA-functionalized colloids. Soft Matter 5, 2422-2430 (2009).

Lin, C. Rinker, S., Wang, X., Liu, Y, Seeman, N.C., H. Yan, H., In Vivo Cloning of Artificial DNA Nanostructures, Proc. Nat. Acad. Sci. (USA) 105, 17626-17631 (2008).

Lincoln, T. A. & Joyce, G. F. Self-sustained replication of an RNA enzyme. Science 323, 1229-1232 (2009).

Rothemund, P. W. K., Folding DNA to create nanoscale shapes and patterns Nature, 440, 297-302, 2006.

Sacanna, S., Irvine, W. T. M., Chaikin, P. M. & Pine, D. J. Lock and key colloids. Nature 464, 575-578 (2010).

Schulman, R. & Winfree, E. Synthesis of crystals with a programmable kinetic barrier to nucleation. Proc. Natl Acad. Sci. USA 104, 15236-15241 (2007).

Tuerk, C., Gold, L., Systematic evolution of ligands by exponential enrichment, Science 249, 505-510 (1990).

Wang, T., Sha, R., Dreyfus, R., Leunissen, M. E., Maass, C., Pine, D., Chaikin, P. M., Seeman, N.C., Self-replication of information-bearing nanoscale patterns, Nature, 478, 225-228, (2011).

Wei, B., Wang, Z. & Mi, Y., Uniquimer: Software of de novo DNA sequence generation for DNA self-assembly—An introduction and the related applications in DNA self-assembly J. Comp. & Theor. Nanosci. 4, 133-141 (2007).

Wintner, E. A., Conn, M. M. & Rebek, J. Jr. Studies in molecular replication. Acc. Chem. Res. 27, 198-203 (1994).

Yoshimura, R. & Fujimoto, K. Ultrafast reversible photo-cross-linking reaction: toward in situ DNA manipulation. Org. Lett. 10, 3227-3230 (2008).

Zhang, H. et al., Folding super-sized DNA origami with scaffold strands from long-range PCR Chem. Commun. 48:6405-6407 (2012).

Zhao, Y. et al., DNA origami delivery system for cancer therapy with tunable release properties. ACSNANO 6(10):8684-8691 (2012).

What is claimed is:

1. A method for exponential self-replication of nucleic acid origami tiles, comprising:
   (i) providing a set of monomers of seed nucleic acid origami tiles, monomers of first generation daughter nucleic acid origami tiles and monomers of second generation daughter nucleic acid origami tiles, each monomer having a long scaffold strand that is folded by a plurality of short staple strands into an origami tile structure having a plurality of horizontal edges and a plurality of faces, with a plurality of sticky cohesive ends protruding from one or more horizontal edges of the tiles and from one or more faces of the tiles;
   (ii) forming a multimer from monomers of seed nucleic acid origami tiles by cohesion of complementary horizontal sticky cohesive ends between the edge of one monomer to the edge of another monomer;
   (iii) mixing the resulting multimer of seed tiles with monomers of first generation daughter (1G) tiles to allow the monomers to anneal to each other by horizontal sticky end cohesion between edges of adjacent 1G monomeric tiles, as enhanced by the 1G monomers first annealing to the multimer of seed tiles by vertical sticky end cohesion between sticky cohesive ends protruding from the faces of adjacent seed and 1G tiles, to form a stacked multimer of seed and 1G tiles;
   (iv) covalently linking the 1G tiles which are in sticky end cohesion with each other in the stacked multimer;
   (v) heating to denature the horizontal sticky end cohesion between monomers of seed tiles and the vertical sticky end cohesion between monomers of seed tiles and 1G tiles to separate the heat resistant covalently linked 1G tiles as a multimer of 1G tiles;
   (vi) mixing the multimer of covalently linked 1G tiles with monomers of second generation daughter (2G) tiles to allow the monomers to anneal to each other by horizontal sticky end cohesion between edges of adjacent 2G monomeric tiles, as enhanced by the 2G monomers first annealing to the multimer of covalently linked 1G tiles by vertical sticky end cohesion between sticky cohesive ends protruding from the faces of adjacent 1G and 2G tiles, to form a stacked multimer of 1G and 2G tiles;
   (vii) covalently linking the 2G tiles which are in sticky end cohesion with each other in the stacked multimer;

(viii) heating to denature the vertical sticky end cohesion between the multimer of 1G tiles and the multimer of 2G tiles in the stacked multimer to separate the multimers of covalently linked 1G tiles and covalently linked 2G tiles;

(ix) incubating the separated multimers with monomers of 1G tiles and 2G tiles to allow the monomers of 1G and 2G tiles to anneal respectively to other 1G and 2G monomers by horizontal sticky end cohesion between edges of adjacent monomers tiles and to a multimer of covalently linked 1G or 2G tiles by vertical sticky end cohesion between sticky cohesive ends protruding from the faces of adjacent 1G and 2G tiles to form stacked multimers of 1G and 2G tiles;

(x) for 1G and 2G tiles not already covalently linked, covalently linking 1G tiles in horizontal sticky end cohesion to each other and covalently link 2G tiles in horizontal sticky end cohesion to each other in the stacked multimers;

(xi) heating to denature the vertical sticky end cohesion between multimers of covalently linked 1G tiles and multimers of covalently linked 2G tiles;

(xii) repeating steps (ix)-(xi) one or more times to self-replicate and exponentially amplify multimers of nucleic acid origami tiles.

2. The method of claim 1, wherein the nucleic acid origami tiles are DNA origami tiles.

3. The method of claim 1, wherein, in step (ix) or in one of the repetitions thereof in (xii), additional amounts of monomers of 1G and 2G tiles are added and mixed with the separated multimers of 1G and 2G tiles.

4. The method of claim 1, wherein the monomers of seed, 1G and 2G tiles are substantially two dimensional with a top and bottom face/surface.

5. The method of claim 4, wherein the monomers are rectangular.

6. The method of claim 1, wherein a hairpin formed from a nucleic acid strand protrudes perpendicularly from a face of the monomer.

7. The method of claim 6, wherein a pendant molecule or moiety is attached to the hairpin.

8. The method of claim 1, wherein the covalently linked 1G and 2G tiles are from photo-crosslinking.

9. The method of claim 8, wherein the photo-crosslinking is with a 3-cyanovinylcarbazole nucleoside.

10. The method of claim 1, further comprising monomers of one or more different sets of seed, 1G and 2G daughter tiles are provided in the same self-replication mixture to selectively amplify a nucleic acid multimer over competing monomers and multimers from the other set(s).

11. The method of claim 10, wherein, for each of the different set(s) of tiles, the monomers each have a sticky cohesive end, which is necessary for forming a multimer, labeled with a different near-infrared dye that produces light-activated local heat generation at a specific wavelength that is different from those of the dyes on competing monomers and multimers of the other sets of tiles.

12. The method of claim 11, further comprising irradiating the tiles at one or more different wavelengths to effect light-activated local heat generation, thereby suppressing sticky end cohesion of competing monomers labeled with dyes that are light-activated at the one or more wavelengths to selectively amplify a multimer in which sticky end cohesion is not suppressed.

13. The method of claim 1, wherein:
each monomer is substantially two dimensional with a top and bottom face and at least three horizontal edges;
at least one edge of each monomer has a plurality of protruding single stranded nucleic acid ends that serve as sticky ends for annealing to complementary single stranded nucleic acid ends of another monomer so as to form adjacent monomers joined by sticky end cohesion; and
the top or bottom face of each monomer has a plurality of single stranded nucleic acid ends that protrude perpendicularly from the plane of the substantially two dimensional monomer (monomeric tile); and the monomers of seed tiles differ from monomers of 1G tiles in the nature of the plurality of single stranded nucleic acid ends that serve as sticky ends for annealing to complementary nucleic acid ends of another monomer.

14. The method of claim 13, wherein:
in step (ii), the multimer of seed tiles is formed in a plane with a top and bottom face from the monomers of seed tiles through the annealing of a plurality of sticky ends with nucleic acid sequence complementarity at the adjacent edges of monomeric seed tiles; and the plurality of single stranded nucleic acid ends that protrude perpendicularly from the top or bottom face of each monomeric seed tile are on the same face of the multimer of seed tiles;

in step (iii), the formed multimer of seed tiles is mixed with monomers of 1G tiles and the monomers of 1G tiles are allowed to anneal to each other and to the multimer of seed tiles to form a stacked multimer of seed and 1G tiles that serves as a first recognition complex for self-replication, wherein:

the annealing of monomers of 1G tiles to each other through sequence complementarity between the plurality of protruding single stranded ends at the edges of adjacent monomeric 1G tiles forms a multimer of 1G tiles in a plane with a top and bottom face;

the plurality of single stranded nucleic acid ends protruding perpendicularly from the plane of the substantially two dimensional monomeric 1G tiles are on the same face of the multimer of 1G tiles; and the annealing of monomers of 1G tiles to the monomeric seed tiles in the multimer of seed tiles is through sequence complementarity between the plurality of single stranded nucleic acid ends that protrude perpendicularly from the planes of the monomeric daughter tiles and the monomeric seed tiles so as to form the stacked multimer in which the plane of the multimer of seed tiles is parallel to the plane of the multimer of 1G tiles and joined thereto by sticky end cohesion;

in step (iv), at least two of the plurality of annealed sticky ends between adjacent monomers in the multimer of daughter tiles forming the first recognition complex are allowed to react to covalently link with complementary strands in the at least two annealed sticky ends so as to be resistant to heat denaturation at a melting temperature (Tm) which denatures the sticky end cohesion between the monomers of seed tiles and monomers of 1G tiles;

in step (v), the sticky end cohesion between monomers of seed tiles and monomers of 1G tiles is denatured by heating at the Tm so as to separate the multimer of 1G tiles, which is resistant to heat denaturation, from the multimer of seed tiles to release the multimers of the first recognition complex;

in step (vi), the heat resistant multimer of 1G tiles are allowed to anneal with monomers of 2G tiles and the monomers of 2G tiles are allowed to anneal to each other to form a second stacked multimer of 1G and 2G tiles that serves as a second recognition complex for self-replication, wherein:

monomers of 2G tiles are annealed to each other through sequence complementarity between the plurality of protruding single stranded ends at the edges of adjacent monomeric 2G tiles to form a multimer of 2G tiles in a plane with a top and bottom face;

the plurality of single stranded nucleic acid ends protruding perpendicularly from the plane of the substantially two dimensional monomeric 2G tiles are on the same face of the multimer of 2G tiles; and the monomers of 2G tiles are annealed to the monomeric 1G tiles in the heat resistant multimer of 1G tiles through sequence complementarity between the plurality of single stranded nucleic acid ends that protrude perpendicularly from the planes of the monomeric 2G tiles and the monomeric 1G tiles so as to form the second stacked multimer in which the plane of the heat resistant multimer of 1G tiles is parallel to the plane of the multimer of 2G tiles and joined thereto by sticky end cohesion;

in step (vii), at least two of the plurality of annealed sticky ends between adjacent monomers in the multimer of 2G tiles forming the second recognition complex are allowed to react to covalently link the complementary strands in the at least two annealed sticky ends together so as to be resistant to heat denaturation at the Tm which denatures the sticky end cohesion between the monomers of the 1G tiles and monomers of 2G tiles;

in step (viii), the sticky end cohesion between the heat resistant multimer of 1G tiles in one plane and the heat resistant multimer of 2G tiles in a second parallel plane is denatured by heating at the Tm to separate the heat resistant multimer of 2G tiles from the heat resistant multimer of 1G tiles to release the heat resistant multimers of 1G and 2G tiles from the second recognition complex;

in step (ix), the heat resistant multimer of 1G tiles and the heat resistant multimer of 2G tiles obtained from step (viii) are mixed with monomers of 1G tiles and 2G tiles with monomers of 1G tiles being allowed to anneal to each other and to the heat resistant multimer of 2G tiles and monomers of 2G tiles being allowed to anneal to each other and to heat resistant multimers of 1G tiles, both forming the second stacked multimer that serves as the second recognition complex, wherein the monomers of 1G and 2G tiles are annealed to corresponding monomers of 1G and 2G tiles through sequence complementarity between the plurality of protruding single stranded ends at the edges of adjacent monomeric 1G or 2G tiles to form a multimer of 1G tiles and a multimer of 2G tiles, both of which have a plane with a top and bottom face;

the plurality of single stranded nucleic acid ends protruding perpendicularly from the plane of the substantially two dimensional monomeric 1G tiles and the plane of the substantially two dimensional monomeric 2G tiles are on the same face of the multimer of 1G tiles and the multimer of 2G tiles, respectively; and the monomers of 1G or 2G tiles are annealed respectively to the monomeric 2G or 1G tiles in the multimer of 2G or 1G tiles through sequence complementarity between the plurality of single stranded nucleic acid ends that protrude perpendicularly from the planes of the monomeric 1G tiles and the monomeric 2G tiles so as to form the second stacked multimer in which the plane of the multimer of 2G tiles is parallel to the plane of the multimer of 1G tiles and joined thereto by sticky end cohesion;

(x) at least two of the plurality of annealed sticky ends between adjacent monomers in the multimer of 1G tiles and in the multimer of 2G tiles in the second recognition complex are allowed to react to covalently link the complementary strands in the at least two annealed sticky ends together so as to be resistant to heat denaturation at the Tm which denatures the vertical sticky end cohesion between monomers of 1G tiles and monomers of 2G tiles;

(xi) the sticky end cohesion between the heat resistant multimer of 1G tiles in one plane and the heat resistant multimer of 2G tiles in a second parallel plane is denatured by heating at the Tm to separate the heat resistant multimers and release them from the second recognition complex;

(xii) repeating steps (ix)-(xi) one or more times to self-replicate and exponentially amplify multimers of 1G and 2G tiles.

15. The method of claim 13, wherein:

each monomer is a rectangle with four horizontal edges;

each monomer has eight single stranded nucleic acid ends that protrude perpendicularly from the same face of the substantially two dimensional rectangular tile for vertical sticky end cohesion to the complementary single stranded nucleic acid ends of another monomeric tile;

each monomer of seed tiles has eight horizontal single stranded nucleic acid ends at one edge of the substantially two dimensional rectangular seed tile for horizontal sticky end cohesion to the complementary single stranded nucleic acid ends of another monomeric seed tile; and each monomer of 1G and 2G tiles has six horizontal single stranded nucleic acid ends at each of two opposing edges of the substantially two dimensional rectangular 1G or 2G tile for horizontal sticky end cohesion to the complementary single stranded nucleic acid ends of, respectively, another monomeric 1G or 2G tile, with four of the six horizontal single stranded nucleic acid ends on one edge having a 3-cyanovinylcarbazole nucleoside for photo-crosslinking to the complementary single stranded nucleic acid ends of an adjacent monomer.

16. The method of claim 4, wherein the monomers are planar.

17. The method of claim 1, wherein the monomers are planar DNA origami tiles having a scaffold strand in the range of 5-10 kb in size.

* * * * *

```
                          SEQUENCE LISTING

<160> NUMBER OF SEQ ID NOS: 345

<210> SEQ ID NO 1
<211> LENGTH: 40
<212> TYPE: DNA
<213> ORGANISM: Artificial Sequence
<220> FEATURE:
<223> OTHER INFORMATION: Synthetic

<400> SEQUENCE: 1
ttctttgatt agtaattatc ggccttgctg gtacacgacc                              40

<210> SEQ ID NO 2
<211> LENGTH: 32
<212> TYPE: DNA
<213> ORGANISM: Artificial Sequence
<220> FEATURE:
<223> OTHER INFORMATION: Synthetic

<400> SEQUENCE: 2
gcaaattatt accgccagcc attgatggat ta                                      32

<210> SEQ ID NO 3
<211> LENGTH: 32
<212> TYPE: DNA
<213> ORGANISM: Artificial Sequence
<220> FEATURE:
<223> OTHER INFORMATION: Synthetic

<400> SEQUENCE: 3
gaggccacca tggaaatacc tttccagtcg gg                                      32

<210> SEQ ID NO 4
<211> LENGTH: 32
<212> TYPE: DNA
<213> ORGANISM: Artificial Sequence
<220> FEATURE:
<223> OTHER INFORMATION: Synthetic

<400> SEQUENCE: 4
```

-continued ccagaatccg tgccagctgc attaagctaa ct                                     32

<210> SEQ ID NO 5
<211> LENGTH: 32
<212> TYPE: DNA
<213> ORGANISM: Artificial Sequence
<220> FEATURE:
<223> OTHER INFORMATION: Synthetic

<400> SEQUENCE: 5
gaaaaaccgc ggggagaggc ggtttaaagt gt                                     32

<210> SEQ ID NO 6
<211> LENGTH: 32
<212> TYPE: DNA
<213> ORGANISM: Artificial Sequence
<220> FEATURE:
<223> OTHER INFORMATION: Synthetic

<400> SEQUENCE: 6
attaaagagg gtggttttc ttttcacaat tc                                      32

<210> SEQ ID NO 7
<211> LENGTH: 32
<212> TYPE: DNA
<213> ORGANISM: Artificial Sequence
<220> FEATURE:
<223> OTHER INFORMATION: Synthetic

<400> SEQUENCE: 7
agtgttgtaa cagctgattg cccttagctg tt                                     32

<210> SEQ ID NO 8
<211> LENGTH: 32
<212> TYPE: DNA
<213> ORGANISM: Artificial Sequence
<220> FEATURE:
<223> OTHER INFORMATION: Synthetic

<400> SEQUENCE: 8
ataaatcaag agagttgcag caaggggtac cg                                     32

<210> SEQ ID NO 9
<211> LENGTH: 40
<212> TYPE: DNA
<213> ORGANISM: Artificial Sequence
<220> FEATURE:
<223> OTHER INFORMATION: Synthetic

<400> SEQUENCE: 9
ttttatcctg tttgatggtg gccccagcag gcgaaatttt                             40

<210> SEQ ID NO 10
<211> LENGTH: 40
<212> TYPE: DNA
<213> ORGANISM: Artificial Sequence
<220> FEATURE:
<223> OTHER INFORMATION: Synthetic

<400> SEQUENCE: 10
ttttgtagaa gaactcaaac aacatcactt gcctgatttt                             40

<210> SEQ ID NO 11
<211> LENGTH: 32
<212> TYPE: DNA

<213> ORGANISM: Artificial Sequence
<220> FEATURE:
<223> OTHER INFORMATION: Synthetic

<400> SEQUENCE: 11
aaaacgctcg agtaaaagag tctgtccatc ac         32

<210> SEQ ID NO 12
<211> LENGTH: 32
<212> TYPE: DNA
<213> ORGANISM: Artificial Sequence
<220> FEATURE:
<223> OTHER INFORMATION: Synthetic

<400> SEQUENCE: 12
aaacctgtct gagaagtgtt tttataatca gt         32

<210> SEQ ID NO 13
<211> LENGTH: 32
<212> TYPE: DNA
<213> ORGANISM: Artificial Sequence
<220> FEATURE:
<223> OTHER INFORMATION: Synthetic

<400> SEQUENCE: 13
gccaacgcgt ctatcaagac aggaacggta cg         32

<210> SEQ ID NO 14
<211> LENGTH: 32
<212> TYPE: DNA
<213> ORGANISM: Artificial Sequence
<220> FEATURE:
<223> OTHER INFORMATION: Synthetic

<400> SEQUENCE: 14
gggcgccaac gtggactcca acgtcaaagg gc         32

<210> SEQ ID NO 15
<211> LENGTH: 32
<212> TYPE: DNA
<213> ORGANISM: Artificial Sequence
<220> FEATURE:
<223> OTHER INFORMATION: Synthetic

<400> SEQUENCE: 15
agacgggctc cagtttggaa caagagtcca ct         32

<210> SEQ ID NO 16
<211> LENGTH: 32
<212> TYPE: DNA
<213> ORGANISM: Artificial Sequence
<220> FEATURE:
<223> OTHER INFORMATION: Synthetic

<400> SEQUENCE: 16
tggccctgaa agaatagccc gagatagggt tg         32

<210> SEQ ID NO 17
<211> LENGTH: 32
<212> TYPE: DNA
<213> ORGANISM: Artificial Sequence
<220> FEATURE:
<223> OTHER INFORMATION: Synthetic

<400> SEQUENCE: 17
gctggtttgt tccgaaatcg gcaaaatccc tt         32

<210> SEQ ID NO 18
<211> LENGTH: 32
<212> TYPE: DNA
<213> ORGANISM: Artificial Sequence
<220> FEATURE:
<223> OTHER INFORMATION: Synthetic

<400> SEQUENCE: 18
agtaataatt ctgacctgaa agcgaactaa ta                                    32

<210> SEQ ID NO 19
<211> LENGTH: 40
<212> TYPE: DNA
<213> ORGANISM: Artificial Sequence
<220> FEATURE:
<223> OTHER INFORMATION: Synthetic

<400> SEQUENCE: 19
caccagtcaa tatccagaac aataaccgtt gtagcaatac                            40

<210> SEQ ID NO 20
<211> LENGTH: 32
<212> TYPE: DNA
<213> ORGANISM: Artificial Sequence
<220> FEATURE:
<223> OTHER INFORMATION: Synthetic

<400> SEQUENCE: 20
tttacattag acaatatttt tgaaaggtta tc                                    32

<210> SEQ ID NO 21
<211> LENGTH: 32
<212> TYPE: DNA
<213> ORGANISM: Artificial Sequence
<220> FEATURE:
<223> OTHER INFORMATION: Synthetic

<400> SEQUENCE: 21
cgctcactgc ccgctacatt ttgaatgcgc ga                                    32

<210> SEQ ID NO 22
<211> LENGTH: 32
<212> TYPE: DNA
<213> ORGANISM: Artificial Sequence
<220> FEATURE:
<223> OTHER INFORMATION: Synthetic

<400> SEQUENCE: 22
cacattaatt aaaaataccg aacgaaatat ca                                    32

<210> SEQ ID NO 23
<211> LENGTH: 32
<212> TYPE: DNA
<213> ORGANISM: Artificial Sequence
<220> FEATURE:
<223> OTHER INFORMATION: Synthetic

<400> SEQUENCE: 23
aaagcctgta aaacagaggt gagggaaaaa tc                                    32

<210> SEQ ID NO 24
<211> LENGTH: 32
<212> TYPE: DNA
<213> ORGANISM: Artificial Sequence
<220> FEATURE:

<223> OTHER INFORMATION: Synthetic

<400> SEQUENCE: 24
cacacaaccg cctgcaacag ccagctggcg aa                                32

<210> SEQ ID NO 25
<211> LENGTH: 32
<212> TYPE: DNA
<213> ORGANISM: Artificial Sequence
<220> FEATURE:
<223> OTHER INFORMATION: Synthetic

<400> SEQUENCE: 25
tcctgtgtgt gctgcaaggc gatttgggaa gg                                32

<210> SEQ ID NO 26
<211> LENGTH: 32
<212> TYPE: DNA
<213> ORGANISM: Artificial Sequence
<220> FEATURE:
<223> OTHER INFORMATION: Synthetic

<400> SEQUENCE: 26
agctcgaagg gttttcccag tcacagcgcc at                                32

<210> SEQ ID NO 27
<211> LENGTH: 40
<212> TYPE: DNA
<213> ORGANISM: Artificial Sequence
<220> FEATURE:
<223> OTHER INFORMATION: Synthetic

<400> SEQUENCE: 27
ttttgcatgc ctgcaggtcg ggccagtgcc aagctttttt                        40

<210> SEQ ID NO 28
<211> LENGTH: 40
<212> TYPE: DNA
<213> ORGANISM: Artificial Sequence
<220> FEATURE:
<223> OTHER INFORMATION: Synthetic

<400> SEQUENCE: 28
ttttaacaga gatagaaccc aagggacatt ctggcctttt                        40

<210> SEQ ID NO 29
<211> LENGTH: 32
<212> TYPE: DNA
<213> ORGANISM: Artificial Sequence
<220> FEATURE:
<223> OTHER INFORMATION: Synthetic

<400> SEQUENCE: 29
agtctttacg ctcaatcgtc tgaacaacag ga                                32

<210> SEQ ID NO 30
<211> LENGTH: 32
<212> TYPE: DNA
<213> ORGANISM: Artificial Sequence
<220> FEATURE:
<223> OTHER INFORMATION: Synthetic

<400> SEQUENCE: 30
actgatagtt ggcaaatcaa cagtttaaaa gt                                32

```
<210> SEQ ID NO 31
<211> LENGTH: 32
<212> TYPE: DNA
<213> ORGANISM: Artificial Sequence
<220> FEATURE:
<223> OTHER INFORMATION: Synthetic

<400> SEQUENCE: 31
gcagaagagg gtgcctaatg agtgatgaat cg                                    32

<210> SEQ ID NO 32
<211> LENGTH: 32
<212> TYPE: DNA
<213> ORGANISM: Artificial Sequence
<220> FEATURE:
<223> OTHER INFORMATION: Synthetic

<400> SEQUENCE: 32
attaacacat acgagccgga agcatgcgta tt                                    32

<210> SEQ ID NO 33
<211> LENGTH: 32
<212> TYPE: DNA
<213> ORGANISM: Artificial Sequence
<220> FEATURE:
<223> OTHER INFORMATION: Synthetic

<400> SEQUENCE: 33 aggggggatga aattgttatc cgctcaccag tg                                   32

<210> SEQ ID NO 34
<211> LENGTH: 32
<212> TYPE: DNA
<213> ORGANISM: Artificial Sequence
<220> FEATURE:
<223> OTHER INFORMATION: Synthetic

<400> SEQUENCE: 34
taacgccatt cgtaatcatg gtcatcaccg cc                                    32

<210> SEQ ID NO 35
<211> LENGTH: 32
<212> TYPE: DNA
<213> ORGANISM: Artificial Sequence
<220> FEATURE:
<223> OTHER INFORMATION: Synthetic

<400> SEQUENCE: 35
aaaacgacac tctagaggat ccccggtcc ac                                     32

<210> SEQ ID NO 36
<211> LENGTH: 32
<212> TYPE: DNA
<213> ORGANISM: Artificial Sequence
<220> FEATURE:
<223> OTHER INFORMATION: Synthetic

<400> SEQUENCE: 36
gattagagag tattagactt tacaaataat gg                                    32

<210> SEQ ID NO 37
<211> LENGTH: 32
<212> TYPE: DNA
<213> ORGANISM: Artificial Sequence
<220> FEATURE:
<223> OTHER INFORMATION: Synthetic
```

```
<400> SEQUENCE: 37
gcactaacta agaatacgtg gcacggcaga tt                          32

<210> SEQ ID NO 38
<211> LENGTH: 32
<212> TYPE: DNA
<213> ORGANISM: Artificial Sequence
<220> FEATURE:
<223> OTHER INFORMATION: Synthetic

<400> SEQUENCE: 38
taaaatatgt attaaatcct ttgcatataa tc                          32

<210> SEQ ID NO 39
<211> LENGTH: 32
<212> TYPE: DNA
<213> ORGANISM: Artificial Sequence
<220> FEATURE:
<223> OTHER INFORMATION: Synthetic

<400> SEQUENCE: 39
ctggtcagcc ctaaaacatc gccattgcgt tg                          32

<210> SEQ ID NO 40
<211> LENGTH: 32
<212> TYPE: DNA
<213> ORGANISM: Artificial Sequence
<220> FEATURE:
<223> OTHER INFORMATION: Synthetic

<400> SEQUENCE: 40
aaccctcaaa caagaaacg agcgagtaac aa                           32

<210> SEQ ID NO 41
<211> LENGTH: 32
<212> TYPE: DNA
<213> ORGANISM: Artificial Sequence
<220> FEATURE:
<223> OTHER INFORMATION: Synthetic

<400> SEQUENCE: 41
taaagcatat tctccgtggg aacaggcctt cc                          32

<210> SEQ ID NO 42
<211> LENGTH: 32
<212> TYPE: DNA
<213> ORGANISM: Artificial Sequence
<220> FEATURE:
<223> OTHER INFORMATION: Synthetic

<400> SEQUENCE: 42
tcttcgctat tacgtgccac gctgtaatgg ga                          32

<210> SEQ ID NO 43
<211> LENGTH: 24
<212> TYPE: DNA
<213> ORGANISM: Artificial Sequence
<220> FEATURE:
<223> OTHER INFORMATION: Synthetic

<400> SEQUENCE: 43
gcgatcgggc atcgtaaccg tgca                                   24

<210> SEQ ID NO 44
<211> LENGTH: 32
```

<210> SEQ ID NO 45
<211> LENGTH: 40
<212> TYPE: DNA
<213> ORGANISM: Artificial Sequence
<220> FEATURE:
<223> OTHER INFORMATION: Synthetic

<400> SEQUENCE: 44
tcgccattga cgacgacagt atcggtaaac gt    32

<210> SEQ ID NO 45
<211> LENGTH: 40
<212> TYPE: DNA
<213> ORGANISM: Artificial Sequence
<220> FEATURE:
<223> OTHER INFORMATION: Synthetic

<400> SEQUENCE: 45
ttttcggcac cgcttctggt actccagcca gctttctttt    40

<210> SEQ ID NO 46
<211> LENGTH: 40
<212> TYPE: DNA
<213> ORGANISM: Artificial Sequence
<220> FEATURE:
<223> OTHER INFORMATION: Synthetic

<400> SEQUENCE: 46
ttttcatttg aggatttaga ccgtcaatag ataatatttt    40

<210> SEQ ID NO 47
<211> LENGTH: 32
<212> TYPE: DNA
<213> ORGANISM: Artificial Sequence
<220> FEATURE:
<223> OTHER INFORMATION: Synthetic

<400> SEQUENCE: 47
tattaatttg aaaggaattg aggatggcta tt    32

<210> SEQ ID NO 48
<211> LENGTH: 32
<212> TYPE: DNA
<213> ORGANISM: Artificial Sequence
<220> FEATURE:
<223> OTHER INFORMATION: Synthetic

<400> SEQUENCE: 48
ttgagtaaat tcctgattat cagaccttttt ac    32

<210> SEQ ID NO 49
<211> LENGTH: 32
<212> TYPE: DNA
<213> ORGANISM: Artificial Sequence
<220> FEATURE:
<223> OTHER INFORMATION: Synthetic

<400> SEQUENCE: 49
cccgtcggca ccttgctgaa cctcaaccac ca    32

<210> SEQ ID NO 50
<211> LENGTH: 32
<212> TYPE: DNA
<213> ORGANISM: Artificial Sequence
<220> FEATURE:
<223> OTHER INFORMATION: Synthetic

<400> SEQUENCE: 50
attgaccgag agccagcagc aaatcggtca gt                    32

<210> SEQ ID NO 51
<211> LENGTH: 32
<212> TYPE: DNA
<213> ORGANISM: Artificial Sequence
<220> FEATURE:
<223> OTHER INFORMATION: Synthetic

<400> SEQUENCE: 51
taggtcacaa taggaacgcc atcatgagca aa                    32

<210> SEQ ID NO 52
<211> LENGTH: 32
<212> TYPE: DNA
<213> ORGANISM: Artificial Sequence
<220> FEATURE:
<223> OTHER INFORMATION: Synthetic

<400> SEQUENCE: 52
tttgagggca ggctgcgcaa ctgtaagttg gg                    32

<210> SEQ ID NO 53
<211> LENGTH: 32
<212> TYPE: DNA
<213> ORGANISM: Artificial Sequence
<220> FEATURE:
<223> OTHER INFORMATION: Synthetic

<400> SEQUENCE: 53
aagatcgcgc cggaaaccag gcaagacgtt gt                    32

<210> SEQ ID NO 54
<211> LENGTH: 32
<212> TYPE: DNA
<213> ORGANISM: Artificial Sequence
<220> FEATURE:
<223> OTHER INFORMATION: Synthetic

<400> SEQUENCE: 54
aagggttaaa cagaaataaa gaaaaatcat ag                    32

<210> SEQ ID NO 55
<211> LENGTH: 32
<212> TYPE: DNA
<213> ORGANISM: Artificial Sequence
<220> FEATURE:
<223> OTHER INFORMATION: Synthetic

<400> SEQUENCE: 55
tacttctgaa caattcgaca actcctttag ga                    32

<210> SEQ ID NO 56
<211> LENGTH: 32
<212> TYPE: DNA
<213> ORGANISM: Artificial Sequence
<220> FEATURE:
<223> OTHER INFORMATION: Synthetic

<400> SEQUENCE: 56
ctgattgtgt ttaacgtcag atgaacgctg ag                    32

<210> SEQ ID NO 57
<211> LENGTH: 32
<212> TYPE: DNA
<213> ORGANISM: Artificial Sequence
<220> FEATURE:
<223> OTHER INFORMATION: Synthetic

<400> SEQUENCE: 57
atcatcatca ttatcattt gcggatcaat at                                32

<210> SEQ ID NO 58
<211> LENGTH: 32
<212> TYPE: DNA
<213> ORGANISM: Artificial Sequence
<220> FEATURE:
<223> OTHER INFORMATION: Synthetic

<400> SEQUENCE: 58
caacattaaa tgtcaccaga aggagcctga tt                                32

<210> SEQ ID NO 59
<211> LENGTH: 32
<212> TYPE: DNA
<213> ORGANISM: Artificial Sequence
<220> FEATURE:
<223> OTHER INFORMATION: Synthetic

<400> SEQUENCE: 59
tgtagccacg cgcagaggcg aattaatata tg                                32

<210> SEQ ID NO 60
<211> LENGTH: 32
<212> TYPE: DNA
<213> ORGANISM: Artificial Sequence
<220> FEATURE:
<223> OTHER INFORMATION: Synthetic

<400> SEQUENCE: 60
ttttaaccgt tggtgtagat gggctgcggg cc                                32

<210> SEQ ID NO 61
<211> LENGTH: 40
<212> TYPE: DNA
<213> ORGANISM: Artificial Sequence
<220> FEATURE:
<223> OTHER INFORMATION: Synthetic

<400> SEQUENCE: 61 aaattttgt taaatcgaaa acaaaattga acggtaatcg                         40

<210> SEQ ID NO 62
<211> LENGTH: 32
<212> TYPE: DNA
<213> ORGANISM: Artificial Sequence
<220> FEATURE:
<223> OTHER INFORMATION: Synthetic

<400> SEQUENCE: 62
taatatttgc atgtcaatca tatgtcattg cc                                32

<210> SEQ ID NO 63
<211> LENGTH: 40
<212> TYPE: DNA
<213> ORGANISM: Artificial Sequence
<220> FEATURE:
<223> OTHER INFORMATION: Synthetic

<400> SEQUENCE: 63
ttttacagga agattgtata cagaaaagcc ccaaaatttt                        40

<210> SEQ ID NO 64
<211> LENGTH: 40
<212> TYPE: DNA
<213> ORGANISM: Artificial Sequence
<220> FEATURE:
<223> OTHER INFORMATION: Synthetic

<400> SEQUENCE: 64
ttttaattat ttgcacgtaa gaacctacca tatcaattt                                40

<210> SEQ ID NO 65
<211> LENGTH: 32
<212> TYPE: DNA
<213> ORGANISM: Artificial Sequence
<220> FEATURE:
<223> OTHER INFORMATION: Synthetic

<400> SEQUENCE: 65
taacagtatg atggcaattc atcaccgaac gt                                      32

<210> SEQ ID NO 66
<211> LENGTH: 32
<212> TYPE: DNA
<213> ORGANISM: Artificial Sequence
<220> FEATURE:
<223> OTHER INFORMATION: Synthetic

<400> SEQUENCE: 66
atcgggagtc cttgaaaaca tagctttcaa at                                      32

<210> SEQ ID NO 67
<211> LENGTH: 32
<212> TYPE: DNA
<213> ORGANISM: Artificial Sequence
<220> FEATURE:
<223> OTHER INFORMATION: Synthetic

<400> SEQUENCE: 67
gctttgaaaa tcgtcgctat taatagcctt ta                                      32

<210> SEQ ID NO 68
<211> LENGTH: 32
<212> TYPE: DNA
<213> ORGANISM: Artificial Sequence
<220> FEATURE:
<223> OTHER INFORMATION: Synthetic

<400> SEQUENCE: 68
caattaccaa ataattcgc gtctaacggc gg                                       32

<210> SEQ ID NO 69
<211> LENGTH: 32
<212> TYPE: DNA
<213> ORGANISM: Artificial Sequence
<220> FEATURE:
<223> OTHER INFORMATION: Synthetic

<400> SEQUENCE: 69
agaagatgtt acctttttta atgggagtaa tg                                      32

<210> SEQ ID NO 70
<211> LENGTH: 32
<212> TYPE: DNA
<213> ORGANISM: Artificial Sequence
<220> FEATURE:
<223> OTHER INFORMATION: Synthetic

<400> SEQUENCE: 70
taaaactatg ttaaaattcg catttctgcc ag                                    32

<210> SEQ ID NO 71
<211> LENGTH: 32
<212> TYPE: DNA
<213> ORGANISM: Artificial Sequence
<220> FEATURE:
<223> OTHER INFORMATION: Synthetic

<400> SEQUENCE: 71
ttgataatag caaatattta aattgcctca gg                                    32

<210> SEQ ID NO 72
<211> LENGTH: 32
<212> TYPE: DNA
<213> ORGANISM: Artificial Sequence
<220> FEATURE:
<223> OTHER INFORMATION: Synthetic

<400> SEQUENCE: 72
gtctgagatt atataactat atgtataaac ac                                    32

<210> SEQ ID NO 73
<211> LENGTH: 32
<212> TYPE: DNA
<213> ORGANISM: Artificial Sequence
<220> FEATURE:
<223> OTHER INFORMATION: Synthetic

<400> SEQUENCE: 73
tttatcaatt gcgtagattt tcagttggat ta                                    32

<210> SEQ ID NO 74
<211> LENGTH: 32
<212> TYPE: DNA
<213> ORGANISM: Artificial Sequence
<220> FEATURE:
<223> OTHER INFORMATION: Synthetic

<400> SEQUENCE: 74
aagagtcacc aatcgcaaga caaacgaccg tg                                    32

<210> SEQ ID NO 75
<211> LENGTH: 32
<212> TYPE: DNA
<213> ORGANISM: Artificial Sequence
<220> FEATURE:
<223> OTHER INFORMATION: Synthetic

<400> SEQUENCE: 75
ccttagaaaa acaataacgg attcgcggaa tt                                    32

<210> SEQ ID NO 76
<211> LENGTH: 32
<212> TYPE: DNA
<213> ORGANISM: Artificial Sequence
<220> FEATURE:
<223> OTHER INFORMATION: Synthetic

<400> SEQUENCE: 76
cttctgtata ccaagttaca aaatgctttc at                                    32

<210> SEQ ID NO 77

```
<211> LENGTH: 32
<212> TYPE: DNA
<213> ORGANISM: Artificial Sequence
<220> FEATURE:
<223> OTHER INFORMATION: Synthetic

<400> SEQUENCE: 77
tgagtgaata gaaccctcat ataagcct ca                                     32

<210> SEQ ID NO 78
<211> LENGTH: 32
<212> TYPE: DNA
<213> ORGANISM: Artificial Sequence
<220> FEATURE:
<223> OTHER INFORMATION: Synthetic

<400> SEQUENCE: 78
catttgaaat gaaacaaaca tcaaagctca tt                                   32

<210> SEQ ID NO 79
<211> LENGTH: 32
<212> TYPE: DNA
<213> ORGANISM: Artificial Sequence
<220> FEATURE:
<223> OTHER INFORMATION: Synthetic

<400> SEQUENCE: 79
acaagagaat cgataattac atttagaaag gc                                   32

<210> SEQ ID NO 80
<211> LENGTH: 32
<212> TYPE: DNA
<213> ORGANISM: Artificial Sequence
<220> FEATURE:
<223> OTHER INFORMATION: Synthetic

<400> SEQUENCE: 80
tgagagtcta tgatattcaa ccgtgagctg aa                                   32

<210> SEQ ID NO 81
<211> LENGTH: 40
<212> TYPE: DNA
<213> ORGANISM: Artificial Sequence
<220> FEATURE:
<223> OTHER INFORMATION: Synthetic

<400> SEQUENCE: 81
ttttctattt ttgagagatc atgccggaga gggtagtttt                           40

<210> SEQ ID NO 82
<211> LENGTH: 40
<212> TYPE: DNA
<213> ORGANISM: Artificial Sequence
<220> FEATURE:
<223> OTHER INFORMATION: Synthetic

<400> SEQUENCE: 82
tttttccggc ttaggttggg gactaccttt ttaacctttt                           40

<210> SEQ ID NO 83
<211> LENGTH: 32
<212> TYPE: DNA
<213> ORGANISM: Artificial Sequence
<220> FEATURE:
<223> OTHER INFORMATION: Synthetic

<400> SEQUENCE: 83
```
gaaaacttga tagcttagat taagatatac ag                         32

<210> SEQ ID NO 84
<211> LENGTH: 32
<212> TYPE: DNA
<213> ORGANISM: Artificial Sequence
<220> FEATURE:
<223> OTHER INFORMATION: Synthetic

<400> SEQUENCE: 84
atattttagt taatttgcgg gagataattt tc                         32

<210> SEQ ID NO 85
<211> LENGTH: 32
<212> TYPE: DNA
<213> ORGANISM: Artificial Sequence
<220> FEATURE:
<223> OTHER INFORMATION: Synthetic

<400> SEQUENCE: 85
tttcaacgcc aaaaacatta tgaccagagg ca                         32

<210> SEQ ID NO 86
<211> LENGTH: 32
<212> TYPE: DNA
<213> ORGANISM: Artificial Sequence
<220> FEATURE:
<223> OTHER INFORMATION: Synthetic

<400> SEQUENCE: 86
caatgcctaa acagtacata aatcattcat tt                         32

<210> SEQ ID NO 87
<211> LENGTH: 32
<212> TYPE: DNA
<213> ORGANISM: Artificial Sequence
<220> FEATURE:
<223> OTHER INFORMATION: Synthetic

<400> SEQUENCE: 87
tgtaggtagc aaggcaaaga attatccaga cg                         32

<210> SEQ ID NO 88
<211> LENGTH: 32
<212> TYPE: DNA
<213> ORGANISM: Artificial Sequence
<220> FEATURE:
<223> OTHER INFORMATION: Synthetic

<400> SEQUENCE: 88
cggagacagt agtagcatta acatttccat at                         32

<210> SEQ ID NO 89
<211> LENGTH: 32
<212> TYPE: DNA
<213> ORGANISM: Artificial Sequence
<220> FEATURE:
<223> OTHER INFORMATION: Synthetic

<400> SEQUENCE: 89
ataaattata caaaggctat caggtaccccc gg                        32

<210> SEQ ID NO 90
<211> LENGTH: 40
<212> TYPE: DNA

<213> ORGANISM: Artificial Sequence
<220> FEATURE:
<223> OTHER INFORMATION: Synthetic

<400> SEQUENCE: 90
cggaatcatg cgttatacaa attctatttt catcgtagga                        40

<210> SEQ ID NO 91
<211> LENGTH: 32
<212> TYPE: DNA
<213> ORGANISM: Artificial Sequence
<220> FEATURE:
<223> OTHER INFORMATION: Synthetic

<400> SEQUENCE: 91
aaataagaaa atgctgatgc aaatatagtg aa                                32

<210> SEQ ID NO 92
<211> LENGTH: 32
<212> TYPE: DNA
<213> ORGANISM: Artificial Sequence
<220> FEATURE:
<223> OTHER INFORMATION: Synthetic

<400> SEQUENCE: 92
tgataaataa cgctcaacag taggaccgca ct                                32

<210> SEQ ID NO 93
<211> LENGTH: 32
<212> TYPE: DNA
<213> ORGANISM: Artificial Sequence
<220> FEATURE:
<223> OTHER INFORMATION: Synthetic

<400> SEQUENCE: 93
cctaaattcc atatttaaca acgcttatca tt                                32

<210> SEQ ID NO 94
<211> LENGTH: 32
<212> TYPE: DNA
<213> ORGANISM: Artificial Sequence
<220> FEATURE:
<223> OTHER INFORMATION: Synthetic

<400> SEQUENCE: 94
cggttgtaca aggataaaaa tttttaacct tg                                32

<210> SEQ ID NO 95
<211> LENGTH: 32
<212> TYPE: DNA
<213> ORGANISM: Artificial Sequence
<220> FEATURE:
<223> OTHER INFORMATION: Synthetic

<400> SEQUENCE: 95
gagcataaat aaagtaccga caaaaaaat aa                                 32

<210> SEQ ID NO 96
<211> LENGTH: 32
<212> TYPE: DNA
<213> ORGANISM: Artificial Sequence
<220> FEATURE:
<223> OTHER INFORMATION: Synthetic

<400> SEQUENCE: 96
tcatacagaa gattcaaaag ggtgaacaat tt                                32

<210> SEQ ID NO 97
<211> LENGTH: 32
<212> TYPE: DNA
<213> ORGANISM: Artificial Sequence
<220> FEATURE:
<223> OTHER INFORMATION: Synthetic

<400> SEQUENCE: 97
tactaatagt caaatcacca tcaatggagc aa                                    32

<210> SEQ ID NO 98
<211> LENGTH: 32
<212> TYPE: DNA
<213> ORGANISM: Artificial Sequence
<220> FEATURE:
<223> OTHER INFORMATION: Synthetic

<400> SEQUENCE: 98
aaggtggcac gagtagattt agtttcaaca tg                                    32

<210> SEQ ID NO 99
<211> LENGTH: 40
<212> TYPE: DNA
<213> ORGANISM: Artificial Sequence
<220> FEATURE:
<223> OTHER INFORMATION: Synthetic

<400> SEQUENCE: 99
ttttaacctg tttagctata ttcgcaaatg gtcaattttt                            40

<210> SEQ ID NO 100
<211> LENGTH: 40
<212> TYPE: DNA
<213> ORGANISM: Artificial Sequence
<220> FEATURE:
<223> OTHER INFORMATION: Synthetic

<400> SEQUENCE: 100
ttttcctgtt tagtatcata taattactag aaaaagtttt                            40

<210> SEQ ID NO 101
<211> LENGTH: 32
<212> TYPE: DNA
<213> ORGANISM: Artificial Sequence
<220> FEATURE:
<223> OTHER INFORMATION: Synthetic

<400> SEQUENCE: 101
gagaatcgta atggtttgaa atacgaacgc ga                                    32

<210> SEQ ID NO 102
<211> LENGTH: 32
<212> TYPE: DNA
<213> ORGANISM: Artificial Sequence
<220> FEATURE:
<223> OTHER INFORMATION: Synthetic

<400> SEQUENCE: 102
aatttaggcc tgtaatactt ttcatcttct ga                                    32

<210> SEQ ID NO 103
<211> LENGTH: 32
<212> TYPE: DNA
<213> ORGANISM: Artificial Sequence
<220> FEATURE:

<223> OTHER INFORMATION: Synthetic

<400> SEQUENCE: 103
ttttcgaggt agaaaccaat caatgtcaga ag    32

<210> SEQ ID NO 104
<211> LENGTH: 32
<212> TYPE: DNA
<213> ORGANISM: Artificial Sequence
<220> FEATURE:
<223> OTHER INFORMATION: Synthetic

<400> SEQUENCE: 104
taattctggc aaaattaagc aatatttaaa tg    32

<210> SEQ ID NO 105
<211> LENGTH: 32
<212> TYPE: DNA
<213> ORGANISM: Artificial Sequence
<220> FEATURE:
<223> OTHER INFORMATION: Synthetic

<400> SEQUENCE: 105
acgacaattg tttatcaaca ataggtttta at    32

<210> SEQ ID NO 106
<211> LENGTH: 32
<212> TYPE: DNA
<213> ORGANISM: Artificial Sequence
<220> FEATURE:
<223> OTHER INFORMATION: Synthetic

<400> SEQUENCE: 106
aacagttggt gtctggaagt ttcaggaagc aa    32

<210> SEQ ID NO 107
<211> LENGTH: 32
<212> TYPE: DNA
<213> ORGANISM: Artificial Sequence
<220> FEATURE:
<223> OTHER INFORMATION: Synthetic

<400> SEQUENCE: 107
agatacattt ttcatttggg gcgctctagc tg    32

<210> SEQ ID NO 108
<211> LENGTH: 32
<212> TYPE: DNA
<213> ORGANISM: Artificial Sequence
<220> FEATURE:
<223> OTHER INFORMATION: Synthetic

<400> SEQUENCE: 108
gccgtttttt accagtataa agccaaggcg tt    32

<210> SEQ ID NO 109
<211> LENGTH: 32
<212> TYPE: DNA
<213> ORGANISM: Artificial Sequence
<220> FEATURE:
<223> OTHER INFORMATION: Synthetic

<400> SEQUENCE: 109
catcgagata aacagttcag aaaaatcgtc at    32

```
<210> SEQ ID NO 110
<211> LENGTH: 32
<212> TYPE: DNA
<213> ORGANISM: Artificial Sequence
<220> FEATURE:
<223> OTHER INFORMATION: Synthetic

<400> SEQUENCE: 110
ccaagaactc aaaaatcagg tctttgttta ga                              32

<210> SEQ ID NO 111
<211> LENGTH: 32
<212> TYPE: DNA
<213> ORGANISM: Artificial Sequence
<220> FEATURE:
<223> OTHER INFORMATION: Synthetic

<400> SEQUENCE: 111
acgagcatcc agtaataaga gaatagctaa at                              32

<210> SEQ ID NO 112
<211> LENGTH: 32
<212> TYPE: DNA
<213> ORGANISM: Artificial Sequence
<220> FEATURE:
<223> OTHER INFORMATION: Synthetic

<400> SEQUENCE: 112
tatcccatta agaggaagcc cgaaataaaa ac                              32

<210> SEQ ID NO 113
<211> LENGTH: 32
<212> TYPE: DNA
<213> ORGANISM: Artificial Sequence
<220> FEATURE:
<223> OTHER INFORMATION: Synthetic

<400> SEQUENCE: 113
aacgcgccaa acaacatgtt cagcccaata aa                              32

<210> SEQ ID NO 114
<211> LENGTH: 32
<212> TYPE: DNA
<213> ORGANISM: Artificial Sequence
<220> FEATURE:
<223> OTHER INFORMATION: Synthetic

<400> SEQUENCE: 114
aaagtacgat tcccaattct gcgaatcaat tc                              32

<210> SEQ ID NO 115
<211> LENGTH: 32
<212> TYPE: DNA
<213> ORGANISM: Artificial Sequence
<220> FEATURE:
<223> OTHER INFORMATION: Synthetic

<400> SEQUENCE: 115
ttttaaatgt acctttaatt gctcaatacc ac                              32

<210> SEQ ID NO 116
<211> LENGTH: 40
<212> TYPE: DNA
<213> ORGANISM: Artificial Sequence
<220> FEATURE:
<223> OTHER INFORMATION: Synthetic
```

<400> SEQUENCE: 116
tttttagagc ttaattgctg attttttgcgg atggcttttt        40

<210> SEQ ID NO 117
<211> LENGTH: 40
<212> TYPE: DNA
<213> ORGANISM: Artificial Sequence
<220> FEATURE:
<223> OTHER INFORMATION: Synthetic

<400> SEQUENCE: 117
ttttatagca agcaaatcag atcattaccg cgcccatttt        40

<210> SEQ ID NO 118
<211> LENGTH: 40
<212> TYPE: DNA
<213> ORGANISM: Artificial Sequence
<220> FEATURE:
<223> OTHER INFORMATION: Synthetic

<400> SEQUENCE: 118
atatagaagg cttatccggt actcaaatgc ttacaagcaa        40

<210> SEQ ID NO 119
<211> LENGTH: 32
<212> TYPE: DNA
<213> ORGANISM: Artificial Sequence
<220> FEATURE:
<223> OTHER INFORMATION: Synthetic

<400> SEQUENCE: 119
accataaagg gtattaaacc aagtgcttaa tt        32

<210> SEQ ID NO 120
<211> LENGTH: 32
<212> TYPE: DNA
<213> ORGANISM: Artificial Sequence
<220> FEATURE:
<223> OTHER INFORMATION: Synthetic

<400> SEQUENCE: 120
ctattataaa tcggctgtct ttcccaacat gt        32

<210> SEQ ID NO 121
<211> LENGTH: 32
<212> TYPE: DNA
<213> ORGANISM: Artificial Sequence
<220> FEATURE:
<223> OTHER INFORMATION: Synthetic

<400> SEQUENCE: 121
caaagcggaa gaagttttgc cagaccagtt ac        32

<210> SEQ ID NO 122
<211> LENGTH: 32
<212> TYPE: DNA
<213> ORGANISM: Artificial Sequence
<220> FEATURE:
<223> OTHER INFORMATION: Synthetic

<400> SEQUENCE: 122
aatatcgcat aagtcctgaa caagaggtaa ag        32

<210> SEQ ID NO 123
<211> LENGTH: 32

```
<212> TYPE: DNA
<213> ORGANISM: Artificial Sequence
<220> FEATURE:
<223> OTHER INFORMATION: Synthetic

<400> SEQUENCE: 123
tcgagcttac actatcataa cccttaatca tt                                       32

<210> SEQ ID NO 124
<211> LENGTH: 32
<212> TYPE: DNA
<213> ORGANISM: Artificial Sequence
<220> FEATURE:
<223> OTHER INFORMATION: Synthetic

<400> SEQUENCE: 124
actccaacgc caaaaggaat tacggaactg gc                                       32

<210> SEQ ID NO 125
<211> LENGTH: 32
<212> TYPE: DNA
<213> ORGANISM: Artificial Sequence
<220> FEATURE:
<223> OTHER INFORMATION: Synthetic

<400> SEQUENCE: 125
aagaggtcaa tataatgctg tagctgacca tt                                       32

<210> SEQ ID NO 126
<211> LENGTH: 32
<212> TYPE: DNA
<213> ORGANISM: Artificial Sequence
<220> FEATURE:
<223> OTHER INFORMATION: Synthetic

<400> SEQUENCE: 126
aggcgtttag ccttaaatca agatggtaat tg                                       32

<210> SEQ ID NO 127
<211> LENGTH: 32
<212> TYPE: DNA
<213> ORGANISM: Artificial Sequence
<220> FEATURE:
<223> OTHER INFORMATION: Synthetic

<400> SEQUENCE: 127
aaatattccc cagctacaat tttagaatta ac                                       32

<210> SEQ ID NO 128
<211> LENGTH: 32
<212> TYPE: DNA
<213> ORGANISM: Artificial Sequence
<220> FEATURE:
<223> OTHER INFORMATION: Synthetic

<400> SEQUENCE: 128
ctggatagcg ctaacgagcg tcttaacata aa                                       32

<210> SEQ ID NO 129
<211> LENGTH: 32
<212> TYPE: DNA
<213> ORGANISM: Artificial Sequence
<220> FEATURE:
<223> OTHER INFORMATION: Synthetic

<400> SEQUENCE: 129
```
ttttgcaaat tgcatcaaaa agatcctaat tt                          32

<210> SEQ ID NO 130
<211> LENGTH: 32
<212> TYPE: DNA
<213> ORGANISM: Artificial Sequence
<220> FEATURE:
<223> OTHER INFORMATION: Synthetic

<400> SEQUENCE: 130
caaaatagcc caatccaaag agatggttta at                          32

<210> SEQ ID NO 131
<211> LENGTH: 32
<212> TYPE: DNA
<213> ORGANISM: Artificial Sequence
<220> FEATURE:
<223> OTHER INFORMATION: Synthetic

<400> SEQUENCE: 131
taagagcaca aagcgaacca gacctaatgc ag                          32

<210> SEQ ID NO 132
<211> LENGTH: 32
<212> TYPE: DNA
<213> ORGANISM: Artificial Sequence
<220> FEATURE:
<223> OTHER INFORMATION: Synthetic

<400> SEQUENCE: 132
tacataacag gtcaggatta gagaatgcaa ct                          32

<210> SEQ ID NO 133
<211> LENGTH: 32
<212> TYPE: DNA
<213> ORGANISM: Artificial Sequence
<220> FEATURE:
<223> OTHER INFORMATION: Synthetic

<400> SEQUENCE: 133
attcaactga agaaaaatct acgtaaccgg at                          32

<210> SEQ ID NO 134
<211> LENGTH: 40
<212> TYPE: DNA
<213> ORGANISM: Artificial Sequence
<220> FEATURE:
<223> OTHER INFORMATION: Synthetic

<400> SEQUENCE: 134
ttttcaggta gaaagattca cggaacaaca ttattatttt                  40

<210> SEQ ID NO 135
<211> LENGTH: 40
<212> TYPE: DNA
<213> ORGANISM: Artificial Sequence
<220> FEATURE:
<223> OTHER INFORMATION: Synthetic

<400> SEQUENCE: 135 tttttttgcgg gaggttttga tagcgaacct cccgactttt                 40

<210> SEQ ID NO 136
<211> LENGTH: 32
<212> TYPE: DNA
<213> ORGANISM: Artificial Sequence

```
<220> FEATURE:
<223> OTHER INFORMATION: Synthetic

<400> SEQUENCE: 136
attttgcaat tgaatcccct tctaagaacg cg                                32

<210> SEQ ID NO 137
<211> LENGTH: 32
<212> TYPE: DNA
<213> ORGANISM: Artificial Sequence
<220> FEATURE:
<223> OTHER INFORMATION: Synthetic

<400> SEQUENCE: 137
cttaccaacg tccaatactg cggacgagaa tg                                32

<210> SEQ ID NO 138
<211> LENGTH: 32
<212> TYPE: DNA
<213> ORGANISM: Artificial Sequence
<220> FEATURE:
<223> OTHER INFORMATION: Synthetic

<400> SEQUENCE: 138
ctaatttggg gggtaatagt aaaataccct ga                                32

<210> SEQ ID NO 139
<211> LENGTH: 32
<212> TYPE: DNA
<213> ORGANISM: Artificial Sequence
<220> FEATURE:
<223> OTHER INFORMATION: Synthetic

<400> SEQUENCE: 139
aaaataaaaa aatgaaaata gcagcgcgaa ac                                32

<210> SEQ ID NO 140
<211> LENGTH: 32
<212> TYPE: DNA
<213> ORGANISM: Artificial Sequence
<220> FEATURE:
<223> OTHER INFORMATION: Synthetic

<400> SEQUENCE: 140
ttcaacttcg tttaccagac gacgagactt ca                                32

<210> SEQ ID NO 141
<211> LENGTH: 32
<212> TYPE: DNA
<213> ORGANISM: Artificial Sequence
<220> FEATURE:
<223> OTHER INFORMATION: Synthetic

<400> SEQUENCE: 141
gtgaattatg acgagaaaca ccagtgctcc at                                32

<210> SEQ ID NO 142
<211> LENGTH: 32
<212> TYPE: DNA
<213> ORGANISM: Artificial Sequence
<220> FEATURE:
<223> OTHER INFORMATION: Synthetic

<400> SEQUENCE: 142
tcattataaa agctgctcat tcaggacggt ca                                32
```

```
<210> SEQ ID NO 143
<211> LENGTH: 32
<212> TYPE: DNA
<213> ORGANISM: Artificial Sequence
<220> FEATURE:
<223> OTHER INFORMATION: Synthetic

<400> SEQUENCE: 143
cgaactaatc agttgagatt taggcttttg at                                    32

<210> SEQ ID NO 144
<211> LENGTH: 32
<212> TYPE: DNA
<213> ORGANISM: Artificial Sequence
<220> FEATURE:
<223> OTHER INFORMATION: Synthetic

<400> SEQUENCE: 144
agcgctaaag cccaataata agagaacgca at                                    32

<210> SEQ ID NO 145
<211> LENGTH: 32
<212> TYPE: DNA
<213> ORGANISM: Artificial Sequence
<220> FEATURE:
<223> OTHER INFORMATION: Synthetic

<400> SEQUENCE: 145
tgaacaccag caatagctat cttagccgaa ca                                    32

<210> SEQ ID NO 146
<211> LENGTH: 32
<212> TYPE: DNA
<213> ORGANISM: Artificial Sequence
<220> FEATURE:
<223> OTHER INFORMATION: Synthetic

<400> SEQUENCE: 146
aacagggaac tcatctttga ccccaagaat ac                                    32

<210> SEQ ID NO 147
<211> LENGTH: 32
<212> TYPE: DNA
<213> ORGANISM: Artificial Sequence
<220> FEATURE:
<223> OTHER INFORMATION: Synthetic

<400> SEQUENCE: 147
taacgtcaca gccatattat ttatcgagag gc                                    32

<210> SEQ ID NO 148
<211> LENGTH: 32
<212> TYPE: DNA
<213> ORGANISM: Artificial Sequence
<220> FEATURE:
<223> OTHER INFORMATION: Synthetic

<400> SEQUENCE: 148
gtaaattggg ctttaagaaa cgattcgcct ga                                    32

<210> SEQ ID NO 149
<211> LENGTH: 32
<212> TYPE: DNA
<213> ORGANISM: Artificial Sequence
<220> FEATURE:
<223> OTHER INFORMATION: Synthetic
```

<400> SEQUENCE: 149
gcttgccccc ttatgcgatt ttaaaggcat ag                                    32

<210> SEQ ID NO 150
<211> LENGTH: 32
<212> TYPE: DNA
<213> ORGANISM: Artificial Sequence
<220> FEATURE:
<223> OTHER INFORMATION: Synthetic

<400> SEQUENCE: 150
aacgtaaccc agtcaggacg ttggaatgca ga                                    32

<210> SEQ ID NO 151
<211> LENGTH: 32
<212> TYPE: DNA
<213> ORGANISM: Artificial Sequence
<220> FEATURE:
<223> OTHER INFORMATION: Synthetic

<400> SEQUENCE: 151
attcattaac tttgaaagag gacagggatc gt                                    32

<210> SEQ ID NO 152
<211> LENGTH: 40
<212> TYPE: DNA
<213> ORGANISM: Artificial Sequence
<220> FEATURE:
<223> OTHER INFORMATION: Synthetic

<400> SEQUENCE: 152
ttttggctga ccttcatcaa accaggcgca taggcttttt                            40

<210> SEQ ID NO 153
<211> LENGTH: 40
<212> TYPE: DNA
<213> ORGANISM: Artificial Sequence
<220> FEATURE:
<223> OTHER INFORMATION: Synthetic

<400> SEQUENCE: 153
ttttcacaag aattgagtta tatcagagag ataacctttt                            40

<210> SEQ ID NO 154
<211> LENGTH: 32
<212> TYPE: DNA
<213> ORGANISM: Artificial Sequence
<220> FEATURE:
<223> OTHER INFORMATION: Synthetic

<400> SEQUENCE: 154
aatgaaatct gaacaaagtc agagtagttg ct                                    32

<210> SEQ ID NO 155
<211> LENGTH: 32
<212> TYPE: DNA
<213> ORGANISM: Artificial Sequence
<220> FEATURE:
<223> OTHER INFORMATION: Synthetic

<400> SEQUENCE: 155 cttttttaaag cgcattagac gggatcctga at                                   32

<210> SEQ ID NO 156

```
<211> LENGTH: 32
<212> TYPE: DNA
<213> ORGANISM: Artificial Sequence
<220> FEATURE:
<223> OTHER INFORMATION: Synthetic

<400> SEQUENCE: 156
ataccaagcc tttacagaga gaattccaga gc                                    32

<210> SEQ ID NO 157
<211> LENGTH: 32
<212> TYPE: DNA
<213> ORGANISM: Artificial Sequence
<220> FEATURE:
<223> OTHER INFORMATION: Synthetic

<400> SEQUENCE: 157
aaagtacaac gaaggcacca acctgtcaca at                                    32

<210> SEQ ID NO 158
<211> LENGTH: 32
<212> TYPE: DNA
<213> ORGANISM: Artificial Sequence
<220> FEATURE:
<223> OTHER INFORMATION: Synthetic

<400> SEQUENCE: 158
taaattgttc cattaaacgg gtaacagcgc ca                                    32

<210> SEQ ID NO 159
<211> LENGTH: 32
<212> TYPE: DNA
<213> ORGANISM: Artificial Sequence
<220> FEATURE:
<223> OTHER INFORMATION: Synthetic

<400> SEQUENCE: 159
gttacttatt gaggactaaa gactgattga gg                                    32

<210> SEQ ID NO 160
<211> LENGTH: 32
<212> TYPE: DNA
<213> ORGANISM: Artificial Sequence
<220> FEATURE:
<223> OTHER INFORMATION: Synthetic

<400> SEQUENCE: 160
atcataagtc ggaacgaggg tagcattatt ca                                    32

<210> SEQ ID NO 161
<211> LENGTH: 32
<212> TYPE: DNA
<213> ORGANISM: Artificial Sequence
<220> FEATURE:
<223> OTHER INFORMATION: Synthetic

<400> SEQUENCE: 161
gtgtacagga gtaatcttga caagtaataa aa                                    32

<210> SEQ ID NO 162
<211> LENGTH: 32
<212> TYPE: DNA
<213> ORGANISM: Artificial Sequence
<220> FEATURE:
<223> OTHER INFORMATION: Synthetic

<400> SEQUENCE: 162
```

```
aataacggct tattacgcag tatggagcca cc                                32

<210> SEQ ID NO 163
<211> LENGTH: 32
<212> TYPE: DNA
<213> ORGANISM: Artificial Sequence
<220> FEATURE:
<223> OTHER INFORMATION: Synthetic

<400> SEQUENCE: 163
aagttaccat acatacataa aggtccatct tt                                32

<210> SEQ ID NO 164
<211> LENGTH: 32
<212> TYPE: DNA
<213> ORGANISM: Artificial Sequence
<220> FEATURE:
<223> OTHER INFORMATION: Synthetic

<400> SEQUENCE: 164
actaaaacaa cgcaaagaca ccacattttc gg                                32

<210> SEQ ID NO 165
<211> LENGTH: 32
<212> TYPE: DNA
<213> ORGANISM: Artificial Sequence
<220> FEATURE:
<223> OTHER INFORMATION: Synthetic

<400> SEQUENCE: 165
atgccactac ggagatttgt atcatttttg tt                                32

<210> SEQ ID NO 166
<211> LENGTH: 32
<212> TYPE: DNA
<213> ORGANISM: Artificial Sequence
<220> FEATURE:
<223> OTHER INFORMATION: Synthetic

<400> SEQUENCE: 166
aggaagttgt cgaaatccgc gaccaacgag ta                                32

<210> SEQ ID NO 167
<211> LENGTH: 32
<212> TYPE: DNA
<213> ORGANISM: Artificial Sequence
<220> FEATURE:
<223> OTHER INFORMATION: Synthetic

<400> SEQUENCE: 167
cagaggctgc cggaacgagg cgcatgaata ag                                32

<210> SEQ ID NO 168
<211> LENGTH: 32
<212> TYPE: DNA
<213> ORGANISM: Artificial Sequence
<220> FEATURE:
<223> OTHER INFORMATION: Synthetic

<400> SEQUENCE: 168
agacagcagg aaccgaactg accacccaaa tc                                32

<210> SEQ ID NO 169
<211> LENGTH: 32
<212> TYPE: DNA
```

<213> ORGANISM: Artificial Sequence
<220> FEATURE:
<223> OTHER INFORMATION: Synthetic

<400> SEQUENCE: 169
caccctcacg acttgagcca accatcgccc ac                                    32

<210> SEQ ID NO 170
<211> LENGTH: 40
<212> TYPE: DNA
<213> ORGANISM: Artificial Sequence
<220> FEATURE:
<223> OTHER INFORMATION: Synthetic

<400> SEQUENCE: 170
ttttgaggct tgcagggagt gatatattcg gtcgcttttt                            40

<210> SEQ ID NO 171
<211> LENGTH: 40
<212> TYPE: DNA
<213> ORGANISM: Artificial Sequence
<220> FEATURE:
<223> OTHER INFORMATION: Synthetic

<400> SEQUENCE: 171
ttttggcatg attaagactc aatacccaaa agaactttt                             40

<210> SEQ ID NO 172
<211> LENGTH: 32
<212> TYPE: DNA
<213> ORGANISM: Artificial Sequence
<220> FEATURE:
<223> OTHER INFORMATION: Synthetic

<400> SEQUENCE: 172
cgtagaaaag aaggaaaccg aggacaagaa ac                                    32

<210> SEQ ID NO 173
<211> LENGTH: 32
<212> TYPE: DNA
<213> ORGANISM: Artificial Sequence
<220> FEATURE:
<223> OTHER INFORMATION: Synthetic

<400> SEQUENCE: 173
ataaaagaga aaagtaagca gataccgaag cc                                    32

<210> SEQ ID NO 174
<211> LENGTH: 32
<212> TYPE: DNA
<213> ORGANISM: Artificial Sequence
<220> FEATURE:
<223> OTHER INFORMATION: Synthetic

<400> SEQUENCE: 174
tttattttaa aacgaaagag gcaacagcga tt                                    32

<210> SEQ ID NO 175
<211> LENGTH: 32
<212> TYPE: DNA
<213> ORGANISM: Artificial Sequence
<220> FEATURE:
<223> OTHER INFORMATION: Synthetic

<400> SEQUENCE: 175
caatagaatt agcgtcagac tgtagtatgg ga                                    32

<210> SEQ ID NO 176
<211> LENGTH: 32
<212> TYPE: DNA
<213> ORGANISM: Artificial Sequence
<220> FEATURE:
<223> OTHER INFORMATION: Synthetic

<400> SEQUENCE: 176
aagacaaacg taatcagtag cgacttcagc gg                32

<210> SEQ ID NO 177
<211> LENGTH: 32
<212> TYPE: DNA
<213> ORGANISM: Artificial Sequence
<220> FEATURE:
<223> OTHER INFORMATION: Synthetic

<400> SEQUENCE: 177
gagggaagaa cgtcaccaat gaaaaggaa tt                32

<210> SEQ ID NO 178
<211> LENGTH: 32
<212> TYPE: DNA
<213> ORGANISM: Artificial Sequence
<220> FEATURE:
<223> OTHER INFORMATION: Synthetic

<400> SEQUENCE: 178
ttaaaggtcc agtagcacca ttacaaaatc tc                32

<210> SEQ ID NO 179
<211> LENGTH: 32
<212> TYPE: DNA
<213> ORGANISM: Artificial Sequence
<220> FEATURE:
<223> OTHER INFORMATION: Synthetic

<400> SEQUENCE: 179
gcataaccta aaggccgctt ttgcgatgaa cg                32

<210> SEQ ID NO 180
<211> LENGTH: 32
<212> TYPE: DNA
<213> ORGANISM: Artificial Sequence
<220> FEATURE:
<223> OTHER INFORMATION: Synthetic

<400> SEQUENCE: 180
accggaaccc accctcagag ccacgaggtt ga                32

<210> SEQ ID NO 181
<211> LENGTH: 32
<212> TYPE: DNA
<213> ORGANISM: Artificial Sequence
<220> FEATURE:
<223> OTHER INFORMATION: Synthetic

<400> SEQUENCE: 181
tcataatcac cagaaccacc gtaacgatct aa                32

<210> SEQ ID NO 182
<211> LENGTH: 40
<212> TYPE: DNA
<213> ORGANISM: Artificial Sequence
<220> FEATURE:

<223> OTHER INFORMATION: Synthetic

<400> SEQUENCE: 182
tcatagcccg tctttccaga cgttacgcct gtagcattcc                                40

<210> SEQ ID NO 183
<211> LENGTH: 32
<212> TYPE: DNA
<213> ORGANISM: Artificial Sequence
<220> FEATURE:
<223> OTHER INFORMATION: Synthetic

<400> SEQUENCE: 183
gtttgcctaa ttcatatggt ttacaatacg ta                                       32

<210> SEQ ID NO 184
<211> LENGTH: 32
<212> TYPE: DNA
<213> ORGANISM: Artificial Sequence
<220> FEATURE:
<223> OTHER INFORMATION: Synthetic

<400> SEQUENCE: 184
agcagcacag ggcgacattc aaccttttca tg                                       32

<210> SEQ ID NO 185
<211> LENGTH: 32
<212> TYPE: DNA
<213> ORGANISM: Artificial Sequence
<220> FEATURE:
<223> OTHER INFORMATION: Synthetic

<400> SEQUENCE: 185
aggccggagt aaatattgac ggaaaacggc ta                                       32

<210> SEQ ID NO 186
<211> LENGTH: 32
<212> TYPE: DNA
<213> ORGANISM: Artificial Sequence
<220> FEATURE:
<223> OTHER INFORMATION: Synthetic

<400> SEQUENCE: 186
caaaatcaga attatcaccg tcacgcagcg aa                                       32

<210> SEQ ID NO 187
<211> LENGTH: 32
<212> TYPE: DNA
<213> ORGANISM: Artificial Sequence
<220> FEATURE:
<223> OTHER INFORMATION: Synthetic

<400> SEQUENCE: 187
cgacaatgac aacatttggg aattctttaa tt                                       32

<210> SEQ ID NO 188
<211> LENGTH: 40
<212> TYPE: DNA
<213> ORGANISM: Artificial Sequence
<220> FEATURE:
<223> OTHER INFORMATION: Synthetic

<400> SEQUENCE: 188
ttttacagct tgataccgat gaggtgaatt tcttaattt                                40

```
<210> SEQ ID NO 189
<211> LENGTH: 40
<212> TYPE: DNA
<213> ORGANISM: Artificial Sequence
<220> FEATURE:
<223> OTHER INFORMATION: Synthetic

<400> SEQUENCE: 189
ttttgccacc ctcagaaccg cgcctccctc agagccttttt                              40

<210> SEQ ID NO 190
<211> LENGTH: 32
<212> TYPE: DNA
<213> ORGANISM: Artificial Sequence
<220> FEATURE:
<223> OTHER INFORMATION: Synthetic

<400> SEQUENCE: 190
gagccgccaa aatcaccgga accattagca aa                                      32

<210> SEQ ID NO 191
<211> LENGTH: 32
<212> TYPE: DNA
<213> ORGANISM: Artificial Sequence
<220> FEATURE:
<223> OTHER INFORMATION: Synthetic

<400> SEQUENCE: 191
agttttgtcc cttattagcg tttgggcaac at                                      32

<210> SEQ ID NO 192
<211> LENGTH: 32
<212> TYPE: DNA
<213> ORGANISM: Artificial Sequence
<220> FEATURE:
<223> OTHER INFORMATION: Synthetic

<400> SEQUENCE: 192
aattttctgc gcgttttcat cggcggaata ag                                      32

<210> SEQ ID NO 193
<211> LENGTH: 32
<212> TYPE: DNA
<213> ORGANISM: Artificial Sequence
<220> FEATURE:
<223> OTHER INFORMATION: Synthetic

<400> SEQUENCE: 193
ttttgctaaa cactgagttt cgtcaataag tt                                      32

<210> SEQ ID NO 194
<211> LENGTH: 32
<212> TYPE: DNA
<213> ORGANISM: Artificial Sequence
<220> FEATURE:
<223> OTHER INFORMATION: Synthetic

<400> SEQUENCE: 194
agtgagaaga tagcaagccc aataacagtg cc                                      32

<210> SEQ ID NO 195
<211> LENGTH: 40
<212> TYPE: DNA
<213> ORGANISM: Artificial Sequence
<220> FEATURE:
<223> OTHER INFORMATION: Synthetic
```

<400> SEQUENCE: 195
gcgaataacc accctcagag ccaccctatt tcggaaccta                    40

<210> SEQ ID NO 196
<211> LENGTH: 32
<212> TYPE: DNA
<213> ORGANISM: Artificial Sequence
<220> FEATURE:
<223> OTHER INFORMATION: Synthetic

<400> SEQUENCE: 196
caaaaaaacg ccaccctcag aaccgccacc ct                            32

<210> SEQ ID NO 197
<211> LENGTH: 32
<212> TYPE: DNA
<213> ORGANISM: Artificial Sequence
<220> FEATURE:
<223> OTHER INFORMATION: Synthetic

<400> SEQUENCE: 197
gtatcggtag gtgtatcacc gtacggatta gg                            32

<210> SEQ ID NO 198
<211> LENGTH: 32
<212> TYPE: DNA
<213> ORGANISM: Artificial Sequence
<220> FEATURE:
<223> OTHER INFORMATION: Synthetic

<400> SEQUENCE: 198
ggcaggtcaa tcctcattaa agccagaatg ga                            32

<210> SEQ ID NO 199
<211> LENGTH: 48
<212> TYPE: DNA
<213> ORGANISM: Artificial Sequence
<220> FEATURE:
<223> OTHER INFORMATION: Synthetic

<400> SEQUENCE: 199
acagacagcc ctcatagtta gcaccagagc cgtctctgaa tttaccgt           48

<210> SEQ ID NO 200
<211> LENGTH: 32
<212> TYPE: DNA
<213> ORGANISM: Artificial Sequence
<220> FEATURE:
<223> OTHER INFORMATION: Synthetic

<400> SEQUENCE: 200
tgtaccgtaa caactttcaa cagtagaatc aa                            32

<210> SEQ ID NO 201
<211> LENGTH: 32
<212> TYPE: DNA
<213> ORGANISM: Artificial Sequence
<220> FEATURE:
<223> OTHER INFORMATION: Synthetic

<400> SEQUENCE: 201
ttttcaggta gaaaggaaca actaccatcg at                            32

<210> SEQ ID NO 202
<211> LENGTH: 32

```
<212> TYPE: DNA
<213> ORGANISM: Artificial Sequence
<220> FEATURE:
<223> OTHER INFORMATION: Synthetic

<400> SEQUENCE: 202
cagaaccgta atttttcac gttgcattag ca                              32

<210> SEQ ID NO 203
<211> LENGTH: 32
<212> TYPE: DNA
<213> ORGANISM: Artificial Sequence
<220> FEATURE:
<223> OTHER INFORMATION: Synthetic

<400> SEQUENCE: 203
tttagtacag gctccaaaag gagcagagcc ag                             32

<210> SEQ ID NO 204
<211> LENGTH: 32
<212> TYPE: DNA
<213> ORGANISM: Artificial Sequence
<220> FEATURE:
<223> OTHER INFORMATION: Synthetic

<400> SEQUENCE: 204
cccggaattt atcagcttgc tttcagttgc gc                             32

<210> SEQ ID NO 205
<211> LENGTH: 40
<212> TYPE: DNA
<213> ORGANISM: Artificial Sequence
<220> FEATURE:
<223> OTHER INFORMATION: Synthetic

<400> SEQUENCE: 205
tttttcgaga gggttgatat aggcggataa gtgccgtttt                     40

<210> SEQ ID NO 206
<211> LENGTH: 40
<212> TYPE: DNA
<213> ORGANISM: Artificial Sequence
<220> FEATURE:
<223> OTHER INFORMATION: Synthetic

<400> SEQUENCE: 206
tttttattca caaacaaata agacgattgg ccttgatttt                     40

<210> SEQ ID NO 207
<211> LENGTH: 32
<212> TYPE: DNA
<213> ORGANISM: Artificial Sequence
<220> FEATURE:
<223> OTHER INFORMATION: Synthetic

<400> SEQUENCE: 207
aagcgcagcc gccagcattg acagcaccct ca                             32

<210> SEQ ID NO 208
<211> LENGTH: 16
<212> TYPE: DNA
<213> ORGANISM: Artificial Sequence
<220> FEATURE:
<223> OTHER INFORMATION: Synthetic

<400> SEQUENCE: 208
```

-continued

```
tccagtaagc gtcata                                              16

<210> SEQ ID NO 209
<211> LENGTH: 16
<212> TYPE: DNA
<213> ORGANISM: Artificial Sequence
<220> FEATURE:
<223> OTHER INFORMATION: Synthetic

<400> SEQUENCE: 209
catggctttt gatgat                                              16

<210> SEQ ID NO 210
<211> LENGTH: 40
<212> TYPE: DNA
<213> ORGANISM: Artificial Sequence
<220> FEATURE:
<223> OTHER INFORMATION: Synthetic

<400> SEQUENCE: 210
acaggagtgt actggtacca gtacaaacta caagtaaatg                    40

<210> SEQ ID NO 211
<211> LENGTH: 32
<212> TYPE: DNA
<213> ORGANISM: Artificial Sequence
<220> FEATURE:
<223> OTHER INFORMATION: Synthetic

<400> SEQUENCE: 211
ttaacggggt cagtgccttg agtaggaacc ca                            32

<210> SEQ ID NO 212
<211> LENGTH: 32
<212> TYPE: DNA
<213> ORGANISM: Artificial Sequence
<220> FEATURE:
<223> OTHER INFORMATION: Synthetic

<400> SEQUENCE: 212
cgtataaaca gttaatgccc cctgcaccct ca                            32

<210> SEQ ID NO 213
<211> LENGTH: 16
<212> TYPE: DNA
<213> ORGANISM: Artificial Sequence
<220> FEATURE:
<223> OTHER INFORMATION: Synthetic

<400> SEQUENCE: 213
ttattctgaa acatga                                              16

<210> SEQ ID NO 214
<211> LENGTH: 16
<212> TYPE: DNA
<213> ORGANISM: Artificial Sequence
<220> FEATURE:
<223> OTHER INFORMATION: Synthetic

<400> SEQUENCE: 214
aagtattaag aggctg                                              16

<210> SEQ ID NO 215
<211> LENGTH: 24
<212> TYPE: DNA
<213> ORGANISM: Artificial Sequence
```

```
<220> FEATURE:
<223> OTHER INFORMATION: Synthetic

<400> SEQUENCE: 215
agactcctca agagaatcag gagg                                              24

<210> SEQ ID NO 216
<211> LENGTH: 32
<212> TYPE: DNA
<213> ORGANISM: Artificial Sequence
<220> FEATURE:
<223> OTHER INFORMATION: Synthetic

<400> SEQUENCE: 216
attagcgggg ttttgctcag taccaagtat ag                                     32

<210> SEQ ID NO 217
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-039

<400> SEQUENCE: 217
atgaatcctt ttggattcat caagtgcttt ttagcacttg tcgagattct ggtcagccct       60
aaaacatcgc cattgcgttg                                                   80

<210> SEQ ID NO 218
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-040-1

<400> SEQUENCE: 218
aaccctcaaa caaaga                                                       16

<210> SEQ ID NO 219
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-040

<400> SEQUENCE: 219
atgaatcctt ttggattcat caagtgcttt ttagcacttg tcgagattaa cgagcgagta       60
acaa                                                                    64

<210> SEQ ID NO 220
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-041-1
```

```
<400> SEQUENCE: 220
taaagcatat tctccg                                              16

<210> SEQ ID NO 221
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-041

<400> SEQUENCE: 221
atgaatcctt ttggattcat caagtgcttt ttagcacttg tcgagatttg ggaacaggcc   60
ttcctgtagc cacgcgcaga                                              80

<210> SEQ ID NO 222
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-042

<400> SEQUENCE: 222
atgaatcctt ttggattcat caagtgcttt ttagcacttg tcgagatttc ttcgctatta   60
cgtgccacgc tgtaatggga                                              80

<210> SEQ ID NO 223
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-049-1

<400> SEQUENCE: 223
cccgtcggca ccttgc                                              16

<210> SEQ ID NO 224
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-049

<400> SEQUENCE: 224
atgaatcctt ttggattcat caagtgcttt ttagcacttg tcgagatttg aacctcaacc   60
acca                                                               64

<210> SEQ ID NO 225
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

<223> OTHER INFORMATION: T-050-1

<400> SEQUENCE: 225
attgaccgag agccag                                              16

<210> SEQ ID NO 226
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-050

<400> SEQUENCE: 226
atgaatcctt ttggattcat caagtgcttt ttagcacttg tcgagattca gcaaatcggt     60
cagt                                                           64

<210> SEQ ID NO 227
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-051

<400> SEQUENCE: 227
atgaatcctt ttggattcat caagtgcttt ttagcacttg tcgagattta ggtcacaata     60
ggaacgccat catgagcaaa                                          80

<210> SEQ ID NO 228
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-059

<400> SEQUENCE: 228
atgaatcctt ttggattcat caagtgcttt ttagcacttg tcgagattgg cgaattaata     60
tatgtgagtg aatagaaccc                                          80

<210> SEQ ID NO 229
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-077

<400> SEQUENCE: 229
atgaatcctt ttggattcat caagtgcttt ttagcacttg tcgagatttc atatataagc     60
ctcagagcat aaataaagta                                          80

<210> SEQ ID NO 230
<211> LENGTH: 80
<212> TYPE: DNA
<213> ORGANISM: Artificial Sequence

```
<220> FEATURE:
<223> OTHER INFORMATION: Synthetic
<220> FEATURE:
<221> NAME/KEY: misc_feature
<223> OTHER INFORMATION: T-095

<400> SEQUENCE: 230
atgaatcctt ttggattcat caagtgcttt ttagcacttg tcgagattcc gacaaaaaaa      60
ataatatccc attaagagga                                                  80

<210> SEQ ID NO 231
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-112

<400> SEQUENCE: 231
atgaatcctt ttggattcat caagtgcttt ttagcacttg tcgagattag cccgaaataa      60
aaaccaaaat agcccaatcc                                                  80

<210> SEQ ID NO 232
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-130

<400> SEQUENCE: 232
atgaatcctt ttggattcat caagtgcttt ttagcacttg tcgagattaa agagatggtt      60
taat                                                                   64

<210> SEQ ID NO 233
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-158

<400> SEQUENCE: 233
atgaatcctt ttggattcat caagtgcttt ttagcacttg tcgagattta aattgttcca      60
ttaaacgggt aacagcgcca                                                  80

<210> SEQ ID NO 234
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: T-176

<400> SEQUENCE: 234
atgaatcctt ttggattcat caagtgcttt ttagcacttg tcgagattaa gacaaacgta      60
atcagtagcg acttcagcgg                                                  80
```

```
<210> SEQ ID NO 235
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-023-1

<400> SEQUENCE: 235
aaagcctgta aaacag                                                      16

<210> SEQ ID NO 236
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-023

<400> SEQUENCE: 236
atgaatcctt ttggattcat caagtgcttt ttagcacttg tcgagattag gtgagggaaa      60
aatc                                                                   64

<210> SEQ ID NO 237
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-040-1

<400> SEQUENCE: 237
aaccctcaaa caaaga                                                      16

<210> SEQ ID NO 238
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-040

<400> SEQUENCE: 238
atgaatcctt ttggattcat caagtgcttt ttagcacttg tcgagattaa cgagcgagta      60
acaa                                                                   64

<210> SEQ ID NO 239
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-049-1

<400> SEQUENCE: 239
cccgtcggca ccttgc                                                      16
```

```
<210> SEQ ID NO 240
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-049

<400> SEQUENCE: 240
atgaatcctt ttggattcat caagtgcttt ttagcacttg tcgagatttg aacctcaacc      60
acca                                                                  64

<210> SEQ ID NO 241
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-050-1

<400> SEQUENCE: 241
attgaccgag agccag                                                     16

<210> SEQ ID NO 242
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-050

<400> SEQUENCE: 242
atgaatcctt ttggattcat caagtgcttt ttagcacttg tcgagattca gcaaatcggt      60
cagt                                                                  64

<210> SEQ ID NO 243
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-051

<400> SEQUENCE: 243
atgaatcctt ttggattcat caagtgcttt ttagcacttg tcgagattta ggtcacaata      60
ggaacgccat catgagcaaa                                                 80

<210> SEQ ID NO 244
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-057

<400> SEQUENCE: 244
```

```
atgaatcctt tggattcat caagtgcttt ttagcacttg tcgagattat catcatcatt    60
atcattttgc ggatcaatat                                               80
```

<210> SEQ ID NO 245
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-060

<400> SEQUENCE: 245

```
atgaatcctt tggattcat caagtgcttt ttagcacttg tcgagatttt ttaaccgttg    60
gtgtagatgg gctgcgggcc                                               80
```

<210> SEQ ID NO 246
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-075

<400> SEQUENCE: 246

```
atgaatcctt tggattcat caagtgcttt ttagcacttg tcgagattcc ttagaaaaac    60
aataacggat tcgcggaatt                                               80
```

<210> SEQ ID NO 247
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-078

<400> SEQUENCE: 247

```
atgaatcctt tggattcat caagtgcttt ttagcacttg tcgagattca tttgaaatga    60
aacaaacatc aaagctcatt                                               80
```

<210> SEQ ID NO 248
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-096

<400> SEQUENCE: 248

```
atgaatcctt tggattcat caagtgcttt ttagcacttg tcgagatttc atacagaaga    60
ttcaaagggg tgaacaattt                                               80
```

<210> SEQ ID NO 249
<211> LENGTH: 64
<212> TYPE: DNA
<213> ORGANISM: Artificial Sequence
<220> FEATURE:

<223> OTHER INFORMATION: Synthetic
<220> FEATURE:
<221> NAME/KEY: misc_feature
<223> OTHER INFORMATION: A-102

<400> SEQUENCE: 249
atgaatcctt ttggattcat caagtgcttt ttagcacttg tcgagattac ttttcatctt    60
ctga                                                                 64

<210> SEQ ID NO 250
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-111

<400> SEQUENCE: 250
atgaatcctt ttggattcat caagtgcttt ttagcacttg tcgagattac gagcatccag    60
taataagaga atagctaaat                                                80

<210> SEQ ID NO 251
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-112-1

<400> SEQUENCE: 251
tatcccatta agagga                                                    16

<210> SEQ ID NO 252
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-112

<400> SEQUENCE: 252
atgaatcctt ttggattcat caagtgcttt ttagcacttg tcgagattag cccgaaataa    60
aaac                                                                 64

<210> SEQ ID NO 253
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-113

<400> SEQUENCE: 253
atgaatcctt ttggattcat caagtgcttt ttagcacttg tcgagattaa cgcgccaaac    60
aacatgttca gcccaataaa                                                80

<210> SEQ ID NO 254

```
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-120

<400> SEQUENCE: 254
atgaatcctt ttggattcat caagtgcttt ttagcacttg tcgagattgt ctttcccaac    60
atgtaattta ggcctgtaat                                                80

<210> SEQ ID NO 255
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-121

<400> SEQUENCE: 255
atgaatcctt ttggattcat caagtgcttt ttagcacttg tcgagattca aagcggaaga    60
agttttgcca gaccagttac                                                80

<210> SEQ ID NO 256
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-122-1

<400> SEQUENCE: 256
aatatcgcat aagtcc                                                    16

<210> SEQ ID NO 257
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-122

<400> SEQUENCE: 257
atgaatcctt ttggattcat caagtgcttt ttagcacttg tcgagatttg aacaagaggt    60
aaag                                                                 64

<210> SEQ ID NO 258
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-123

<400> SEQUENCE: 258
atgaatcctt ttggattcat caagtgcttt ttagcacttg tcgagatttc gagcttacac    60
```
tatcataacc cttaatcatt                                                    80

<210> SEQ ID NO 259
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-131

<400> SEQUENCE: 259
atgaatcctt ttggattcat caagtgcttt ttagcacttg tcgagattta agagcacaaa       60
gcgaaccaga cctaatgcag                                                   80

<210> SEQ ID NO 260
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-138

<400> SEQUENCE: 260
atgaatcctt ttggattcat caagtgcttt ttagcacttg tcgagattta gtaaaatacc       60
ctgactatta taaatcggct                                                   80

<210> SEQ ID NO 261
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-149

<400> SEQUENCE: 261
atgaatcctt ttggattcat caagtgcttt ttagcacttg tcgagattgc ttgccccctt       60
atgcgatttt aaaggcatag                                                   80

<210> SEQ ID NO 262
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-156-1

<400> SEQUENCE: 262
ataccaagcc tttaca                                                       16

<210> SEQ ID NO 263
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: A-156

<400> SEQUENCE: 263
atgaatcctt ttggattcat caagtgcttt ttagcacttg tcgagattga gagaattcca    60
gagcctaatt tgggggggtaa                                                80

<210> SEQ ID NO 264
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Dimer-R-045

<400> SEQUENCE: 264
ttttcggcac cgcttctggt actccagcca gctttctgtc gtggtca                  47

<210> SEQ ID NO 265
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Dimer-R-063

<400> SEQUENCE: 265
ttttacagga agattgtata cagaaaagcc ccaaaagcgc ttcaata                  47

<210> SEQ ID NO 266
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Dimer-R-081

<400> SEQUENCE: 266
ttttctattt ttgagagatc atgccggaga gggtagcgca ttcactt                  47

<210> SEQ ID NO 267
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Dimer-R-099

<400> SEQUENCE: 267
ttttaacctg tttagctata ttcgcaaatg gtcaattggg tcttcct                  47

<210> SEQ ID NO 268
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Dimer-R-116

<400> SEQUENCE: 268
tttttagagc ttaattgctg attttttgcgg atggctttat tggcgtt                     47

<210> SEQ ID NO 269
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Dimer-R-134

<400> SEQUENCE: 269
ttttcaggta gaaagattca cggaacaaca ttattaggct tgttcga                      47

<210> SEQ ID NO 270
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Dimer-R-152

<400> SEQUENCE: 270
ttttggctga ccttcatcaa accaggcgca taggctagtt ccgtgc                       47

<210> SEQ ID NO 271
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Dimer-R-170

<400> SEQUENCE: 271
ttttgaggct tgcagggagt gatatattcg gtcgctaacc gagtatc                      47

<210> SEQ ID NO 272
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Dimer-L-046

<400> SEQUENCE: 272
ttttcatttg aggatttaga ccgtcaatag ataatatgac cacgaca                      47

<210> SEQ ID NO 273
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Dimer-L-064

<400> SEQUENCE: 273
ttttaattat ttgcacgtaa gaacctacca tatcaatatt gaagcgc                      47

<210> SEQ ID NO 274

```
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Dimer-L-082

<400> SEQUENCE: 274
tttttccggc ttaggttggg gactaccttt ttaaccaagt gaatgcg          47

<210> SEQ ID NO 275
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Dimer-L-100

<400> SEQUENCE: 275
ttttcctgtt tagtatcata taattactag aaaagagga agaccca          47

<210> SEQ ID NO 276
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Dimer-L-117

<400> SEQUENCE: 276
ttttatagca agcaaatcag atcattaccg cgcccaaacg ccaataa          47

<210> SEQ ID NO 277
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Dimer-L-135

<400> SEQUENCE: 277 tttttttgcgg gaggttttga tagcgaacct cccgactcga acaagcc          47

<210> SEQ ID NO 278
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Dimer-L-153

<400> SEQUENCE: 278
ttttcacaag aattgagtta tatcagagag ataaccgcac ggaaact          47

<210> SEQ ID NO 279
<211> LENGTH: 47
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<223> OTHER INFORMATION: Dimer-L-171

<400> SEQUENCE: 279
ttttggcatg attaagactc aatacccaaa agaactgata ctcggtt            47

<210> SEQ ID NO 280
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 9A-056

<400> SEQUENCE: 280
aaaaaaaaac tgattgtgtt taacgtcaga tgaacgctga g                  41

<210> SEQ ID NO 281
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 9A-092

<400> SEQUENCE: 281
aaaaaaaaat gataaataac gctcaacagt aggaccgcac t                  41

<210> SEQ ID NO 282
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 9A-127

<400> SEQUENCE: 282
aaaaaaaaaa aatattcccc agctacaatt ttagaattaa c                  41

<210> SEQ ID NO 283
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 9A-163

<400> SEQUENCE: 283
aaaaaaaaaa agttaccata catacataaa ggtccatctt t                  41

<210> SEQ ID NO 284
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 9A-062
```

<400> SEQUENCE: 284
aaaaaaaaat aatatttgca tgtcaatcat atgtcattgc c            41

<210> SEQ ID NO 285
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 9A-098

<400> SEQUENCE: 285
aaaaaaaaaa aggtggcacg agtagattta gtttcaacat g            41

<210> SEQ ID NO 286
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 9A-133

<400> SEQUENCE: 286
aaaaaaaaaa ttcaactgaa gaaaatcta cgtaaccgga t             41

<210> SEQ ID NO 287
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 9A-169

<400> SEQUENCE: 287
aaaaaaaaac accctcacga cttgagccaa ccatcgccca c            41

<210> SEQ ID NO 288
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1-Seed-038

<400> SEQUENCE: 288
taaaatatgt attaaatcct ttgcatataa tctttttttt tatgagacgg   50

<210> SEQ ID NO 289
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1-Seed-044

<400> SEQUENCE: 289
tcgccattga cgacgacagt atcggtaaac gttttttttt tgtaggcagt   50

<210> SEQ ID NO 290
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1-Seed-074

<400> SEQUENCE: 290
aagagtcacc aatcgcaaga caaacgaccg tgttttttt tcgtgttcag        50

<210> SEQ ID NO 291
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1-Seed-080

<400> SEQUENCE: 291
tgagagtcta tgatattcaa ccgtgagctg aattttttt tcgtatgtgc        50

<210> SEQ ID NO 292
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1-Seed-109

<400> SEQUENCE: 292
catcgagata aacagttcag aaaaatcgtc atttttttt tcagcgttag        50

<210> SEQ ID NO 293
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1-Seed-115

<400> SEQUENCE: 293
ttttaaatgt acctttaatt gctcaatacc acttttttt tcttggttcg        50

<210> SEQ ID NO 294
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1-Seed-145

<400> SEQUENCE: 294
tgaacaccag caatagctat cttagccgaa cattttttt tccattccga        50

<210> SEQ ID NO 295
<211> LENGTH: 50

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1-Seed-151

<400> SEQUENCE: 295
attcattaac tttgaaagag gacagggatc gtttttttt tggagagtcc                50

<210> SEQ ID NO 296
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1-FG-038

<400> SEQUENCE: 296
taaaatatgt attaaatcct ttgcatataa tctttttttt tactgcctac                50

<210> SEQ ID NO 297
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1-FG-044

<400> SEQUENCE: 297
tcgccattga cgacgacagt atcggtaaac gtttttttt tccgtctcat                50

<210> SEQ ID NO 298
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1-FG-074

<400> SEQUENCE: 298
aagagtcacc aatcgcaaga caaacgaccg tgtttttttt tgcacatacg                50

<210> SEQ ID NO 299
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1-FG-080

<400> SEQUENCE: 299
tgagagtcta tgatattcaa ccgtgagctg aatttttttt tctgaacacg                50

<210> SEQ ID NO 300
<211> LENGTH: 50
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<223> OTHER INFORMATION: 1-FG-109

<400> SEQUENCE: 300
catcgagata aacagttcag aaaaatcgtc attttttttt tcgaaccaag                50

<210> SEQ ID NO 301
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1-FG-115

<400> SEQUENCE: 301
ttttaaatgt acctttaatt gctcaatacc acttttttttt tctaacgctg               50

<210> SEQ ID NO 302
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1-FG-145

<400> SEQUENCE: 302
tgaacaccag caatagctat cttagccgaa cattttttttt tggactctcc               50

<210> SEQ ID NO 303
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 1-FG-151

<400> SEQUENCE: 303
attcattaac tttgaaagag gacagggatc gttttttttt ttcggaatgg                50

<210> SEQ ID NO 304
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-Seed-038

<400> SEQUENCE: 304
taaaatatgt attaaatcct ttgcatataa tcttttttttt ttatgcaccc               50

<210> SEQ ID NO 305
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-Seed-044
```

<400> SEQUENCE: 305
tcgccattga cgacgacagt atcggtaaac gttttttttt tatcgagtgc    50

<210> SEQ ID NO 306
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-Seed-074

<400> SEQUENCE: 306
aagagtcacc aatcgcaaga caaacgaccg tgttttttttt tacctgggtc    50

<210> SEQ ID NO 307
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-Seed-080

<400> SEQUENCE: 307
tgagagtcta tgatattcaa ccgtgagctg aattttttttt tggaaagtcg    50

<210> SEQ ID NO 308
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-Seed-109

<400> SEQUENCE: 308
catcgagata aacagttcag aaaaatcgtc attttttttt ttgcttcacg    50

<210> SEQ ID NO 309
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-Seed-115

<400> SEQUENCE: 309
ttttaaatgt acctttaatt gctcaatacc acttttttttt tagctgttgt    50

<210> SEQ ID NO 310
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-Seed-145

<400> SEQUENCE: 310
tgaacaccag caatagctat cttagccgaa cattttttttt tcctcttgcc    50

<210> SEQ ID NO 311
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-Seed-151

<400> SEQUENCE: 311
attcattaac tttgaaagag gacagggatc gttttttttt tgagcgattc                50

<210> SEQ ID NO 312
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-FG-038

<400> SEQUENCE: 312
taaaatatgt attaaatcct ttgcatataa tctttttttt tgcactcgat                50

<210> SEQ ID NO 313
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-FG-044

<400> SEQUENCE: 313
tcgccattga cgacgacagt atcggtaaac gttttttttt tgggtgcata                50

<210> SEQ ID NO 314
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-FG-074

<400> SEQUENCE: 314
aagagtcacc aatcgcaaga caaacgaccg tgttttttttt tcgactttcc               50

<210> SEQ ID NO 315
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-FG-080

<400> SEQUENCE: 315
tgagagtcta tgatattcaa ccgtgagctg aatttttttt tgacccaggt                50

<210> SEQ ID NO 316
<211> LENGTH: 50
<212> TYPE: DNA

```
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-FG-109

<400> SEQUENCE: 316
catcgagata aacagttcag aaaaatcgtc attttttttt tacaacagct            50

<210> SEQ ID NO 317
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-FG-115

<400> SEQUENCE: 317
ttttaaatgt acctttaatt gctcaatacc acttttttttt tcgtgaagca           50

<210> SEQ ID NO 318
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-FG-145

<400> SEQUENCE: 318
tgaacaccag caatagctat cttagccgaa cattttttttt tgaatcgctc           50

<210> SEQ ID NO 319
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2-FG-151

<400> SEQUENCE: 319
attcattaac tttgaaagag gacagggatc gtttttttttt tggcaagagg          50

<210> SEQ ID NO 320
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR700-9A-092

<400> SEQUENCE: 320
aaaaaaaaat gataaataac gctcaacagt aggaccgcac t                    41

<210> SEQ ID NO 321
<211> LENGTH: 41
<212> TYPE: DNA
<213> ORGANISM: Artificial Sequence
<220> FEATURE:
<223> OTHER INFORMATION: Synthetic
<220> FEATURE:
```

<221> NAME/KEY: misc_feature
<223> OTHER INFORMATION: IR700-9A-127

<400> SEQUENCE: 321
aaaaaaaaaa aatattcccc agctacaatt ttagaattaa c                               41

<210> SEQ ID NO 322
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR700-9A-098

<400> SEQUENCE: 322
aaaaaaaaaa aggtggcacg agtagattta gtttcaacat g                               41

<210> SEQ ID NO 323
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR700-9A-133

<400> SEQUENCE: 323
aaaaaaaaaa ttcaactgaa gaaaatcta cgtaaccgga t                                41

<210> SEQ ID NO 324
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR700-063

<400> SEQUENCE: 324
taggttttac aggaagattg tatacagaaa agccccaaaa tttt                            44

<210> SEQ ID NO 325
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR700 -064

<400> SEQUENCE: 325
acctatttaa ttatttgcac gtaagaacct accatatcaa tttt                            44

<210> SEQ ID NO 326
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR700-152

<400> SEQUENCE: 326

```
agtcttttgg ctgaccttca tcaaaccagg cgcataggct tttt                44
```

<210> SEQ ID NO 327
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR700 -153

<400> SEQUENCE: 327

```
agacttttca caagaattga gttatatcag agagataacc tttt                44
```

<210> SEQ ID NO 328
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR700-9A-092

<400> SEQUENCE: 328

```
aaaaaaaaat gataaataac gctcaacagt aggaccgcac t                   41
```

<210> SEQ ID NO 329
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR700-9A-127

<400> SEQUENCE: 329

```
aaaaaaaaaa aatattcccc agctacaatt ttagaattaa c                   41
```

<210> SEQ ID NO 330
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR700-9A-098

<400> SEQUENCE: 330

```
aaaaaaaaaa aggtggcacg agtagattta gtttcaacat g                   41
```

<210> SEQ ID NO 331
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR700-9A-133

<400> SEQUENCE: 331

```
aaaaaaaaaa ttcaactgaa gaaaaatcta cgtaaccgga t                   41
```

<210> SEQ ID NO 332
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR800-9A-092

<400> SEQUENCE: 332
aaaaaaaaat gataaataac gctcaacagt aggaccgcac t                41

<210> SEQ ID NO 333
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR800-9A-127

<400> SEQUENCE: 333
aaaaaaaaaa aatattcccc agctacaatt ttagaattaa c                41

<210> SEQ ID NO 334
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR800-9A-098

<400> SEQUENCE: 334
aaaaaaaaaa aggtggcacg agtagattta gtttcaacat g                41

<210> SEQ ID NO 335
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR800-9A-133

<400> SEQUENCE: 335
aaaaaaaaaa ttcaactgaa gaaaaatcta cgtaaccgga t                41

<210> SEQ ID NO 336
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR800-063

<400> SEQUENCE: 336
taggttttac aggaagattg tatacagaaa agccccaaaa tttt             44

<210> SEQ ID NO 337
<211> LENGTH: 44
<212> TYPE: DNA
<213> ORGANISM: Artificial Sequence

```
<220> FEATURE:
<223> OTHER INFORMATION: Synthetic
<220> FEATURE:
<221> NAME/KEY: misc_feature
<223> OTHER INFORMATION: IR800-064

<400> SEQUENCE: 337
acctatttaa ttatttgcac gtaagaacct accatatcaa tttt                    44

<210> SEQ ID NO 338
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR800-152

<400> SEQUENCE: 338
agtcttttgg ctgaccttca tcaaaccagg cgcataggct tttt                    44

<210> SEQ ID NO 339
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR800 -153

<400> SEQUENCE: 339 agactttctca caagaattga gttatatcag agagataacc tttt                   44

<210> SEQ ID NO 340
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR800-9A-092

<400> SEQUENCE: 340
aaaaaaaaat gataaataac gctcaacagt aggaccgcac t                       41

<210> SEQ ID NO 341
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR800-9A-127

<400> SEQUENCE: 341
aaaaaaaaaa aatattcccc agctacaatt ttagaattaa c                       41

<210> SEQ ID NO 342
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

<223> OTHER INFORMATION: IR800-9A-098

<400> SEQUENCE: 342
aaaaaaaaaa aggtggcacg agtagattta gtttcaacat g    41

<210> SEQ ID NO 343
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IR800-9A-133

<400> SEQUENCE: 343
aaaaaaaaaa ttcaactgaa gaaaaatcta cgtaaccgga t    41

<210> SEQ ID NO 344
<211> LENGTH: 7249
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: M13mp18 Bacterial phage

<400> SEQUENCE: 344

| | | |
|---|---|---|
| aatgctacta ctattagtag aattgatgcc accttttcag ctcgcgcccc aaatgaaaat | 60 |
| atagctaaac aggttattga ccatttgcga aatgtatcta atggtcaaac taaatctact | 120 |
| cgttcgcaga attgggaatc aactgttata tggaatgaaa cttccagaca ccgtacttta | 180 |
| gttgcatatt taaaacatgt tgagctacag cattatattc agcaattaag ctctaagcca | 240 |
| tccgcaaaaa tgacctctta tcaaaaggag caattaaagg tactctctaa tcctgacctg | 300 |
| ttggagtttg cttccggtct ggttcgcttt gaagctcgaa ttaaaacgcg atatttgaag | 360 |
| tctttcgggc ttcctcttaa tcttttgat gcaatccgct ttgcttctga ctataatagt | 420 |
| cagggtaaag acctgatttt tgatttatgg tcattctcgt tttctgaact gtttaaagca | 480 |
| tttgagggg attcaatgaa tatttatgac gattccgcag tattggacgc tatccagtct | 540 |
| aaacatttta ctattacccc ctctggcaaa acttcttttg caaagcctc tcgctatttt | 600 |
| ggtttttatc gtcgtctggt aaacgagggt tatgatagtg ttgctcttac tatgcctcgt | 660 |
| aattcctttt ggcgttatgt atctgcatta gttaatgtg gtattcctaa atctcaactg | 720 |
| atgaatcttt ctacctgtaa taatgttgtt ccgttagttc gttttattaa cgtagatttt | 780 |
| tcttcccaac gtcctgactg gtataatgag ccagttctta aaatcgcata aggtaattca | 840 |
| caatgattaa agttgaaatt aaaccatctc aagcccaatt tactactcgt tctggtgttt | 900 |
| ctcgtcaggg caagccttat tcactgaatg agcagctttg ttacgttgat ttgggtaatg | 960 |
| aatatccggt tcttgtcaag attactcttg atgaaggtca gccagcctat gcgcctggtc | 1020 |
| tgtacaccgt tcatctgtcc tctttcaaag ttggtcagtt cggttccctt atgattgacc | 1080 |
| gtctgcgcct cgttccggct aagtaacatg gagcaggtcg cggatttcga cacaatttat | 1140 |
| caggcgatga tacaaatctc cgttgtactt tgtttcgcgc ttggtataat cgctggggt | 1200 |
| caaagatgag tgttttagtg tattcttttg cctctttcgt tttaggttgg tgccttcgta | 1260 |
| gtggcattac gtattttacc cgtttaatgg aaacttcctc atgaaaaagt ctttagtcct | 1320 |
| caaagcctct gtagccgttg ctaccctcgt tccgatgctg tctttcgctg ctgagggtga | 1380 |

```
cgatcccgca aaagcggcct ttaactccct gcaagcctca gcgaccgaat atatcggtta    1440
tgcgtgggcg atggttgttg tcattgtcgg cgcaactatc ggtatcaagc tgtttaagaa    1500
attcacctcg aaagcaagct gataaaccga tacaattaaa ggctcctttt ggagcctttt    1560
ttttggagat tttcaacgtg aaaaaattat tattcgcaat tcctttagtt gttccttct    1620 attctcactc cgctgaaact gttgaaagtt gtttagcaaa atcccataca gaaaattcat    1680
ttactaacgt ctggaaagac gacaaaactt tagatcgtta cgctaactat gagggctgtc    1740
tgtggaatgc tacaggcgtt gtagtttgta ctggtgacga aactcagtgt tacggtacat    1800
gggttcctat tgggcttgct atccctgaaa atgagggtgg tggctctgag ggtggcggtt    1860
ctgagggtgg cggttctgag ggtggcggta ctaaacctcc tgagtacggt gatacaccta    1920
ttccgggcta tacttatatc aaccctctcg acggcactta tccgcctggt actgagcaaa    1980
accccgctaa tcctaatcct tctcttgagg agtctcagcc tcttaatact ttcatgtttc    2040
agaataatag gttccgaaat aggcaggggg cattaactgt ttatacgggc actgttactc    2100
aaggcactga ccccgttaaa acttattacc agtacactcc tgtatcatca aaagccatgt    2160
atgacgctta ctggaacggt aaattcagag actgcgcttt ccattctggc tttaatgagg    2220
atttatttgt ttgtgaatat caaggccaat cgtctgacct gcctcaacct cctgtcaatg    2280
ctggcggcgg ctctggtggt ggttctggtg gcggctctga gggtggtggc tctgagggtg    2340
gcggttctga gggtggcggc tctgagggag gcggttccgg tggtggctct ggttccggtg    2400
attttgatta tgaaaagatg gcaaacgcta ataagggggc tatgaccgaa aatgccgatg    2460
aaaacgcgct acagtctgac gctaaaggca aacttgattc tgtcgctact gattacggtg    2520
ctgctatcga tggtttcatt ggtgacgttt ccggccttgc taatggtaat ggtgctactg    2580
gtgattttgc tggctctaat tcccaaatgg ctcaagtcgg tgacggtgat aattcacctt    2640
taatgaataa tttccgtcaa tatttacctt ccctccctca atcggttgaa tgtcgccctt    2700
ttgtctttgg cgctggtaaa ccatatgaat tttctattga ttgtgacaaa ataaacttat    2760
tccgtggtgt ctttgcgttt cttttatatg ttgccacctt tatgtatgta ttttctacgt    2820
ttgctaacat actgcgtaat aaggagtctt aatcatgcca gttcttttgg gtattccgtt    2880
attattgcgt ttcctcggtt tccttctggt aactttgttc ggctatctgc ttactttct    2940 taaaagggc ttcggtaaga tagctattgc tatttcattg tttcttgctc ttattattgg    3000
gcttaactca attcttgtgg gttatctctc tgatattagc gctcaattac cctctgactt    3060
tgttcagggt gttcagttaa ttctcccgtc taatgcgctt ccctgttttt atgttattct    3120
ctctgtaaag gctgctattt tcatttttga cgttaaacaa aaaatcgttt cttatttgga    3180
ttgggataaa taatatggct gtttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt actttacctt    3660
ttgtcggtac tttatattct cttattactg gctcgaaaat gcctctgcct aaattacatg    3720
```

```
ttggcgttgt taaatatggc gattctcaat taagccctac tgttgagcgt tggctttata    3780
ctggtaagaa tttgtataac gcatatgata ctaaacaggc ttttctagt aattatgatt     3840
ccggtgttta ttcttattta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta aatgtaatta attttgtttt cttgatgttt    4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaataattt tgatatggta ggttctaacc cttccattat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg ctctaatct attagttgtt     4740
agtgctccta aagatatttt agataaacctt cctcaattcc tttcaactgt tgatttgcca    4800
actgaccaga tattgattga gggtttgata tttgaggttc agcaaggtga tgctttagat    4860
ttttcatttg ctgctggctc tcagcgtggc actgttgcag gcggtgttaa tactgaccgc    4920
ctcacctctg tttatctctc tgctggtggt tcgttcggta tttttaatgg cgatgtttta    4980
gggctatcag ttcgcgcatt aaagactaat agccattcaa aaatattgtc tgtgccacgt    5040
attcttacgc tttcaggtca gaagggttct atctctgttg gccagaatgt ccctttttatt   5100
actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tctttttactc   5340
ggtggcctca ctgattataa aaacacttct caggattctg gcgtaccgtt cctgtctaaa    5400
atccctttaa tcggcctcct gtttagctcc cgctctgatt ctaacgagga aagcacgtta    5460
tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt ccccgtcaag ctctaaatcg    5640
ggggctccct ttagggttcc gatttagtgc tttacggcac ctcgacccca aaaaacttga    5700
tttgggtgat ggttcacgta gtgggccatc gccctgatag acggtttttc gccctttgac    5760
gttggagtcc acgttcttta atagtggact cttgttccaa actggaacaa cactcaaccc    5820
tatctcgggc tattctttg atttataagg gattttgccg atttcggaac caccatcaaa     5880
caggattttc gcctgctggg gcaaaccagc gtggaccgct tgctgcaact ctctcagggc    5940
caggcggtga agggcaatca gctgttgccc gtctcactgg tgaaaagaaa aaccaccctg    6000
gcgcccaata cgcaaaccgc ctctccccgc gcgttggccg attcattaat gcagctggca    6060
cgacaggttt cccgactgga aagcgggcag tgagcgcaac gcaattaatg tgagttagct    6120
```

```
cactcattag gcaccccagg ctttacactt tatgcttccg gctcgtatgt tgtgtggaat    6180
tgtgagcgga taacaatttc acacaggaaa cagctatgac catgattacg aattcgagct    6240
cggtacccgg ggatcctcta gagtcgacct gcaggcatgc aagcttggca ctggccgtcg    6300
ttttacaacg tcgtgactgg gaaaaccctg gcgttaccca acttaatcgc cttgcagcac    6360 atccccttt cgccagctgg cgtaatagcg aagaggcccg caccgatcgc ccttcccaac    6420
agttgcgcag cctgaatggc gaatggcgct ttgcctggtt tccggcacca gaagcggtgc    6480
cggaaagctg gctggagtgc gatcttcctg aggccgatac tgtcgtcgtc ccctcaaact    6540
ggcagatgca cggttacgat gcgcccatct acaccaacgt gacctatccc attacggtca    6600
atccgccgtt tgttcccacg gagaatccga cgggttgtta ctcgctcaca tttaatgttg    6660
atgaaagctg gctacaggaa ggccagacgc gaattatttt tgatggcgtt cctattggtt    6720
aaaaaatgag ctgatttaac aaaaatttaa tgcgaatttt aacaaaatat taacgtttac    6780
aatttaaata tttgcttata caatcttcct gttttggggg cttttctgat tatcaaccgg    6840
ggtacatatg attgacatgc tagttttacg attaccgttc atcgattctc ttgtttgctc    6900
cagactctca ggcaatgacc tgatagcctt tgtagatctc tcaaaaatag ctaccctctc    6960
cggcattaat ttatcagcta gaacggttga atatcatatt gatggtgatt tgactgtctc    7020
cggcctttct cacccttttg aatctttacc tacacattac tcaggcattg catttaaaat    7080
atatgagggt tctaaaaatt tttatccttg cgttgaaata aaggcttctc ccgcaaaagt    7140
attacagggt cataatgttt ttggtacaac cgatttagct ttatgctctg aggctttatt    7200 gcttaattt gctaattctt tgccttgcct gtatgattta ttggatgtt                 7249

<210> SEQ ID NO 345
<211> LENGTH: 48
<212> TYPE: DNA
<213> ORGANISM: Artificial Sequence
<220> FEATURE:
<223> OTHER INFORMATION: Synthetic

<400> SEQUENCE: 345
atgaatcctt ttggattcat caagtgcttt ttagcacttg tcgagatt                 48
```